United States Patent [19]

Satoh et al.

[11] Patent Number: 4,822,791
[45] Date of Patent: Apr. 18, 1989

[54] PHARMACEUTICAL COMPOSITIONS OF-2,2-1,1-[BIS-2,2'-(3,1-BENZOXAZIN-4-ONE)9 ETHYLENES

[75] Inventors: Toshio Satoh; Hitoshi Matsumoto; Hisao Kakegawa, all of Tokushima; Yoshiko Kato, Kobe; Juichi Riku, Uji; Junji Yoshinaga, Neyagawa; Yoshifumi Kanamoto, Kashihara, all of Japan

[73] Assignee: Sawai Pharmaceutical Co., Ltd., Japan

[21] Appl. No.: 162,881

[22] Filed: Mar. 2, 1988

Related U.S. Application Data

[62] Division of Ser. No. 909,468, Sep. 19, 1986, Pat. No. 4,755,506, which is a division of Ser. No. 697,573, Feb. 1, 1985, Pat. No. 4,634,777.

[30] Foreign Application Priority Data

| | | | |
|---|---|---|---|
| Feb. 8, 1984 | [JP] | Japan | 59-22360 |
| Aug. 13, 1984 | [JP] | Japan | 59-169702 |
| Aug. 27, 1984 | [JP] | Japan | 59-179064 |
| Sep. 17, 1984 | [JP] | Japan | 59-195219 |
| Sep. 20, 1984 | [JP] | Japan | 59-197836 |

[51] Int. Cl.$^4$ .................. A61K 31/535; C07D 265/36
[52] U.S. Cl. .................................. 514/212; 514/218; 514/228.2; 514/230.5; 544/58.6; 544/73
[58] Field of Search ................ 544/73, 58.6; 540/575, 540/599; 514/217, 218, 228.2, 230.5

[56] References Cited

FOREIGN PATENT DOCUMENTS

| | | |
|---|---|---|
| 1235324 | 3/1967 | Fed. Rep. of Germany . |
| 2659417 | 7/1977 | Fed. Rep. of Germany . |
| 3209486 | 9/1982 | Fed. Rep. of Germany . |
| 83431 | 7/1979 | Japan . |
| 110081 | 7/1981 | Japan . |

OTHER PUBLICATIONS

Shepel et al., "N,N'-Malonybis(Aminoterephthalic Acid)", *Chem Abstracts*, 70, 15:67926v, (1969).
Black et al., "Metal Template Reactions. XV The Scope of Macrocyclic Metal Complex Formation from Malonamido Dicarbonyl Precursors.": *Australian J. Chem.*, 36, pp. 1133–1140.
Satoh et al., "Studies on Methodology of Finding Novel Anti-Allergenic Agents with the Guidance of Anti-Hyaluronidase Activity", *VIIIth International Symposium on Medicinal Chemistry*, Aug. 27–31, 1984.

*Primary Examiner*—Richard L. Raymond
*Attorney, Agent, or Firm*—Scully, Scott, Murphy & Presser

[57] ABSTRACT

This invention relates to pharmaceutical compositions of compounds of the general formula:

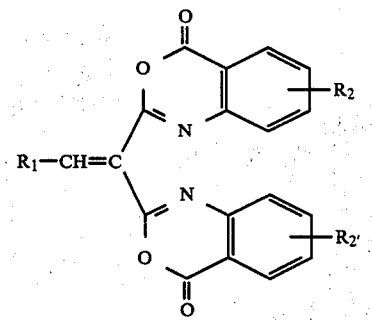

wherein $R^1$ is an aryl group or a substituted aryl group wherein the substituent is halogen, hydroxy, $C_{(1-6)}$ lower alkoxy, $C_{(1-6)}$ lower alkylenedioxy, halo $C_{(1-6)}$ lower alkyl, cyano, nitro, mono- or di-$C_{(1-6)}$ alkylamino or $C_{(1-6)}$ lower alkanoylamino; or a 5-membered or 6-membered $C_{(1-6)}$ alkyl substituted or unsubstituted heterocyclic group containing a heteroatom selected from oxygen, nitrogen, and sulfur, or a condensed heterocyclic group consisting of a heterocycle as defined above and a benzene nucleus, and $R^2$ and $R^{2'}$ are, independently, hydrogen, halogen, nitro, $C_{(1-6)}$ lower alkyl or $C_{(1-6)}$ lower alkoxy. These compounds have been found to exhibit hyaluronidase inhibiting activity, anti-allergic activity and anti-ulcerous activity. The present invention further contemplates processes for the preparation of said compounds and their pharmaceutical compositions.

3 Claims, 12 Drawing Sheets

PHARMACEUTICAL COMPOSITIONS OF-2,2-1,1-[BIS-2,2'-(3,1-BENZOXAZIN-4-ONE)9 ETHYLENES

This is a division of copending application Ser. No. 909,468 filed on Sept. 19, 1986, now U.S. Pat. No. 4,755,506 which in turn is a division of Ser. No. 697,573 filed Feb. 1, 1985, now U.S. Pat. No. 4,634,777.

BACKGROUND OF THE INVENTION

1. Field of the Invention

The present invention relates to [(1,3-dioxo-1,3-propanediyl)diimino]bisbenzoic acid derivatives which have hyaluronidase-inhibiting, anti-allergic, immunomodulating and anti-ulcerous activities, process for preparation thereof and pharmaceutical composition comprising the said derivative.

It is well known that hyaluronidase is present in various parts of living organism normally in an inactive form and act as a phlogovenic enzyme at the inflammatory site. For example, hyaluronidase has an important role in induction of I (immediate) type allergic reaction and hence the use of hyaluronidase-inhibiting drug in these pathologic conditions appears reasonable.

On the other hand, the conventional antiallergic agents such as chlorpheniramine maleate, disodium cromoglicate, tranilast etc. have a number of deficiencies such as induction of undesirable side effect, insufficiency of peroral absorption, unsatisfactoriness of therapeutic effect and so on. Also, there has been a continuous demand for the anti-ulcerous agent which has a mechanism of action approaching the causal treatment. The inventors have succeeded in developing a antiallergic and anti-ulcerous agent which has an excellent anti-hyaluronidase activity, on the basis of a conception that hyaluronidase inhibitor is useful as a causal treatment of pathologic conditions such as a allergic disease.

2. Related Disclosures

Japanese Patent Publication (Unexamined) No. 7716/1981 discloses 2,2'-[(1, omega-dioxo-1, omega-alkane (C$_{1-10}$)diyl)diimino]bisbenzoic acid as a cerebral vasospasmodic inhibitor. Japanese Patent Publication (Unexamined) No. 13660/1983 discloses [(1,3-dioxo-1,3-(propanediyl)diimino]bisbenzoic acid as an azo dyestuff. Australian Journal of Chemistry 36 (1983) 1133–1140 discloses dimethyl 2,2'-[(1,3-dioxo-2-phenylmethylene-1,3-propanediyl)diimino]bisbenzoate as an intermediate for metal-complexing agent. This dimethyl ester was prepared by a method in which phenylmethylene malonic dichloride was reacted with methyl anthranilate. The said method, however, is disadvantageous and cannot be actually carried out in the commercial production. Further, 2,2'-[(1,3-dioxo-2-arylmethylene-1,3-propanediyl)diimino]bisbenzoic acid is published by T. Satoh, H. Kakegawa, Y. Momoi, H. Matsumoto, J. Yoshinaga and J. Riku, the inventors, at VIIIth International Symposium on Medicinal Chemistry, held in Sweden on Aug. 27–31, 1984.

SUMMARY OF INVENTION

In one aspect, the present invention relates to a compound of the general formula:

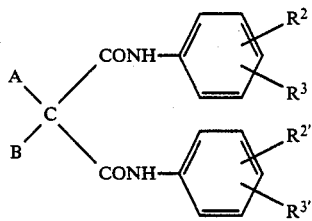

wherein A and B are both hydrogen, or one of A and B is a group (G) of the formula:

and the other is a group $R^5$ wherein $R^1$ is an aryl group or a heterocyclic group, both of them being optionally substituted, and $R^4$ and $R^5$ are both hydrogen or together form a single chemical bond, $R^2$ and $R^{2'}$ are independently hydrogen, halogen, nitro, lower alkyl or lower alkoxy, and $R^3$ and $R^{3'}$ are independently carboxy or its functional derivative, with the proviso that (a) when A and B are both hydrogen, then $R^2$ and $R^{2'}$ *cannot be both hydrogen, and*

(b) when one of A and B is the group G and the other is the group $R^5$ wherein $R^4$ and $R^5$ together form a single chemical bond, $R^1$ is unsubstituted aryl and $R^2$ and $R^{2'}$ are both hydrogen, then $R^3$ and $R^{3'}$ are independently carboxy or its functional derivative other than methyl ester, and, where applicable, pharmaceutically acceptable salts thereof.

The compound (I) of the present invention can be prepared by the following processes.

(a) Group $R^{3a}$ and $R^{3'a}$ in a compound of the general formula:

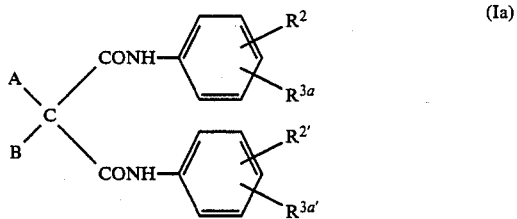

wherein $R^{3a}$ and $R^{3a'}$ are independently functional derivative of carboxy, and A, B, and $R^2$ and $R^{2'}$ are as defined above, is converted into carboxy group to give a compound of the general formula:

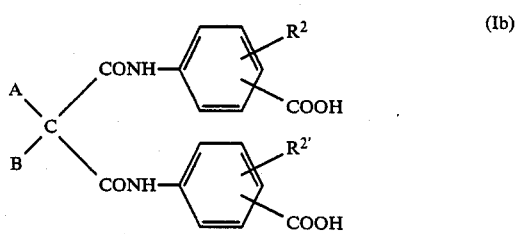

wherein A, B, $R^2$ and $R^{2'}$ are as defined above or (b) A compound of the general formula:

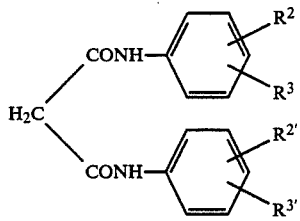 (Ic)

wherein $R^2$, $R^{2'}$, $R^3$ and $R^{3'}$ are so defined above, or a metal salt thereof is reacted with a compound of the general formula:

 (II)

wherein $R^1$ is as defined above, to give a compound of the general formula:

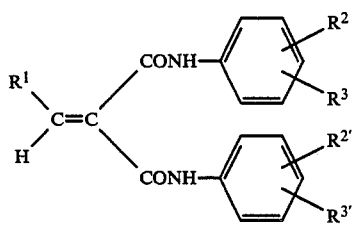 (Id)

wherein $R^1$, $R^2$, $R^{2'}$, $R^3$ and $R^{3'}$ are as defined above, or (c) A compound of the general formula:

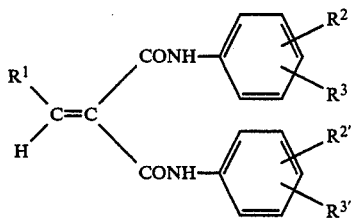 (Id)

wherein $R^1$, $R^2$, $R^{2'}$, $R^3$ and $R^{3'}$ are as defined above, is reduced to give a compound of the general formula:

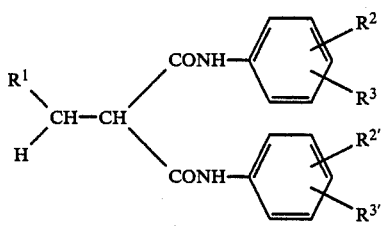 (Ie)

wherein $R^1$, $R^2$, $R^{2'}$, $R^3$ and $R^{3'}$ are as defined above, or (d) A compound of the general formula:

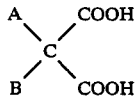 (III)

wherein A and B are defined above, or a reactive derivative at the carboxy groups thereof is reacted with a compound of the general formula:

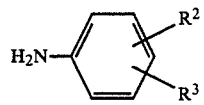 (IV)

wherein $R^2$ and $R^3$ are as defined above, and a compound of the general formula:

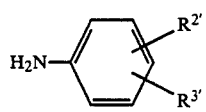 (IV')

wherein $R^{2'}$ and $R^{3'}$ are as defined above, or reactive derivatives at the amino groups in these compounds to give a compound of the general formula:

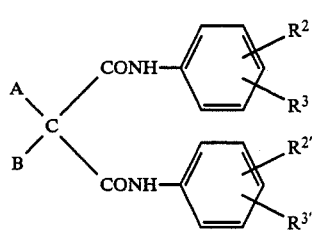 (I)

wherein A, B, $R^2$, $R^{2'}$, $R^3$ and $R^{3'}$ are as defined above, or (e) A compound of the general formula:

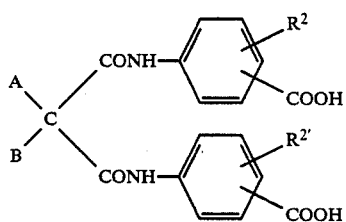 (Ib)

wherein A, B, $R^2$, and $R^{2'}$ are as defined above, is esterified to give a compound of the general formula:

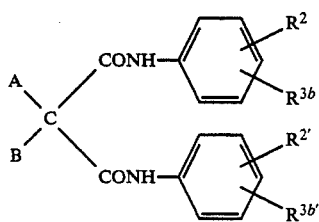 (If)

wherein $R^{3b}$ and $R^{3b'}$ are independently esterified carboxy, and A, B, $R^2$ and $R^{2'}$ are as defined above, or (f) A compound of the general formula:

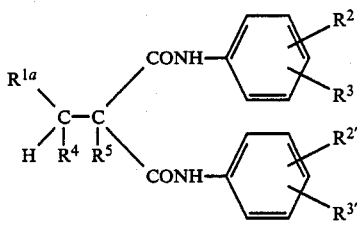

(Ig)

wherein $R^{1a}$ is aryl substituted with hydroxy, and $R^2$, $R^{2'}$, $R^3$, $R^{3'}$, $R^4$ and $R^5$ are as defined above, is lower-alkylated to give a compound of the general formula:

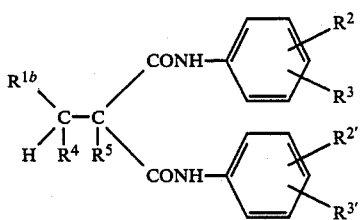

(Ih)

wherein $R^{1b}$ is aryl substituted with lower alkoxy, and $R^2$, $R^{2'}$, $R^3$, $R^{3'}$, $R^4$ and $R^5$ are as defined above, or (g) A compound of the general formula:

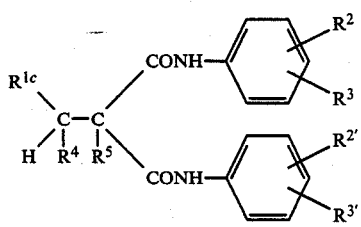

(Ii)

wherein
$R^{1c}$ is pyrrolyl or indolyl, and
$R^2$, $R^{2'}$, $R^3$, $R^{3'}$, $R^4$ and $R^5$ are as defined above,
is lower-alkylated to give a compound of the general formula:

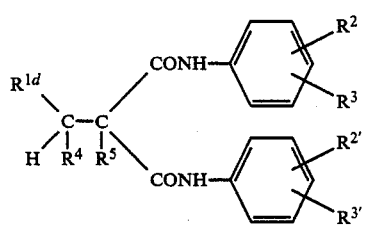

(Ij)

wherein $R^{1d}$ is N-lower alkyl pyrrolyl or N-lower alkyl indolyl, and $R^2$, $R^{2'}$, $R^3$, $R^{3'}$, $R^4$ and $R^5$ are as defined above.

In another aspect, the present invention relates to a pharmaceutical composition comprising as an active ingredient a compound of the general formula:

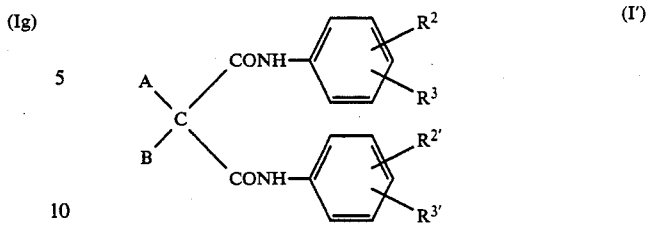

(I')

wherein A and B are both hydrogen, or one of A and B is a group (G) of the formula:

(G)

and the other is a group $R^5$
wherein $R^1$ is an aryl group or a heterocyclic group, both of them being optionally substituted, and $R^4$ and $R^5$ are both hydrogen or together form a single chemical bond,
$R^2$ and $R^{2'}$ are independently hydrogen, halogen, nitro, lower alkyl or lower alkoxy, and $R^3$ and $R^{3'}$ are independently carboxy or its functional derivative, with the proviso that
(a) when A and B are both hydrogen, then $R^2$ and $R^{2'}$ cannot be both hydrogen,
in association with a pharmaceutically acceptable carrier, diluent or excipient.

Among the compound (I'), the compound of the general formula:

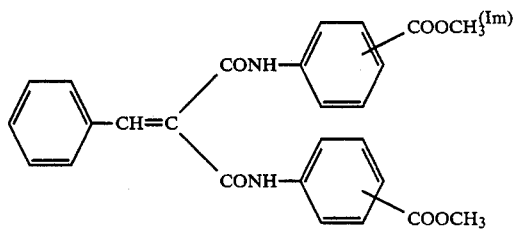

(Im)

wherein the group —COOCH$_3$ is located at any one of ortho, meta and para position to the group —CONH—, can be prepared by the following processes.

(i) A compound of the general formula:

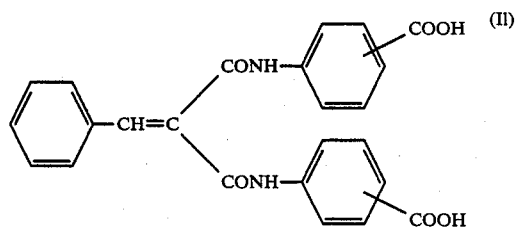

(II)

or a reactive derivative at the carboxy groups thereof is reacted with a methylating agent, or (ii) A compound of the general formula:

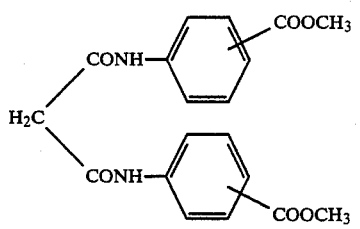

or a metal salt thereof is reacted with benzaldehyde.

Among compounds which can be used for the starting materials in the present invention, compounds represented by formula (V) infra are novel and can be prepared by the following processes.

(A) A compound of the general formula:

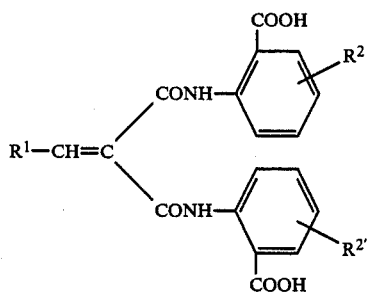

wherein $R^1$, $R^2$ and $R^{2'}$ are as defined above, is subjected to dehydrating reaction to give compound (V).

(B) A compound of the general formula:

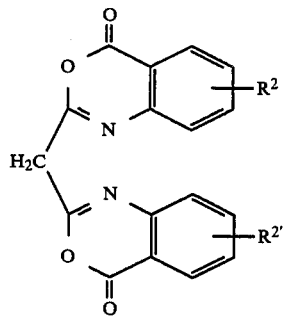

wherein $R^2$ and $R^{2'}$ are as defined above, is reacted with a compound of the general formula:

wherein $R^1$ is as defined above, to give the compound (V).

In further aspect, the present invention relates to the pharmaceutical composition comprising as an active ingredient a compound of the general formula:

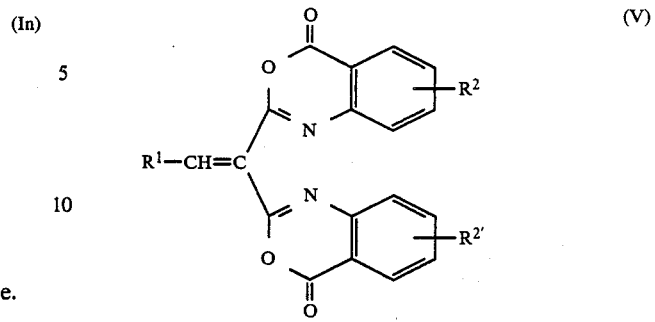

wherein
$R^1$ is an aryl group or a heterocyclic group, both of them being optionally substituted,
$R^2$ and $R^{2'}$ are independently hydrogen, halogen, nitro, lower alkyl or lower alkoxy,
with a pharmaceutically acceptable carrier, diluent or excipient.

DETAILED DESCRIPTION OF THE INVENTION

Figure 1:
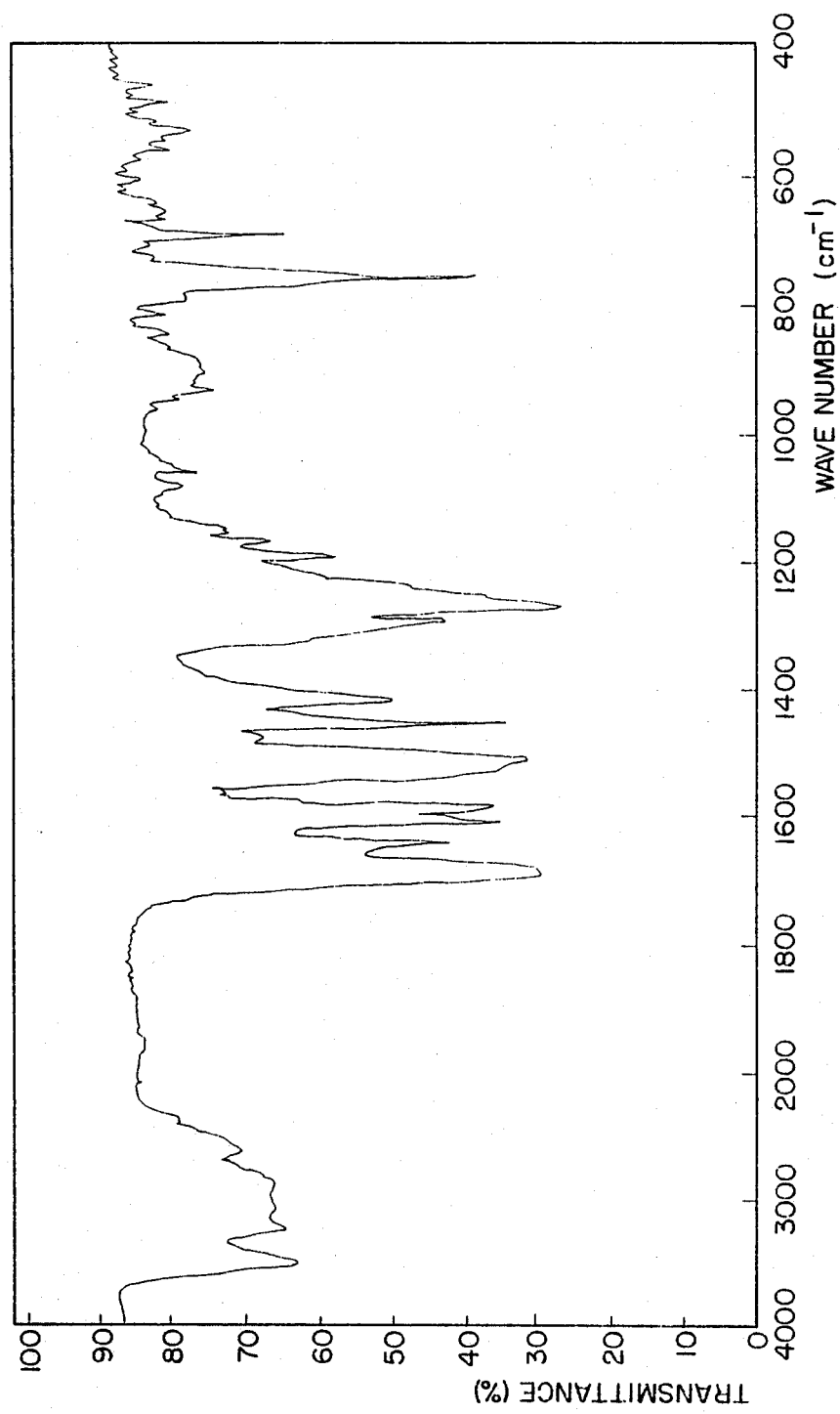

The terms and definitions described in this specification are illustrated as follows.

When both A and B are hydrogen, the formulae (I) and (I') represent the formula:

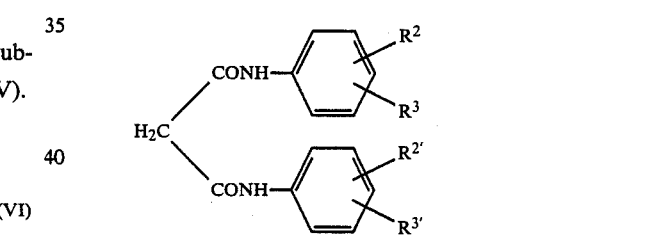

when one of A and B is the group

and the other is the group $R^5$, the formulae (I) and (I') represent the formula:

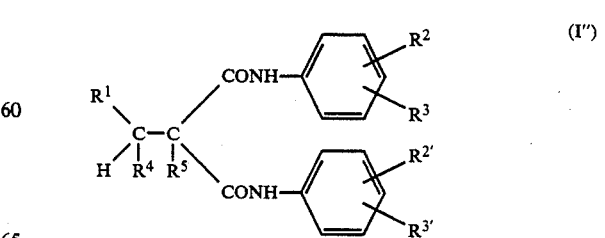

When $R^4$ and $R^5$ together form a singl chemical bond, the formula (I") represents the formula:

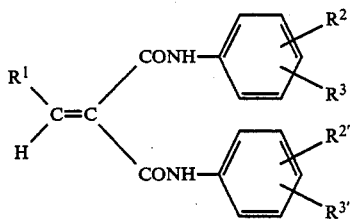

(Id)

and when $R^4$ and $R^5$ are both hydrogen, the formula (I″) represents the formula:

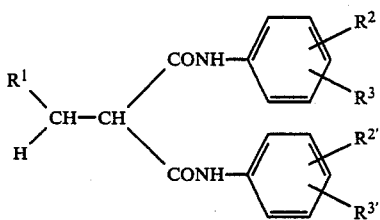

(Ie)

One group of the compound (I) is a compound of the formula:

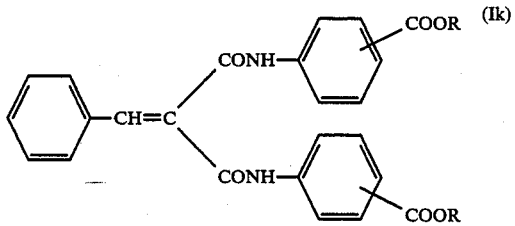

(Ik)

wherein R is a residue derived from an alcohol having two or more carbon atoms by removing hydroxy group.

The term "lower" is used to intend a group having 1 to 6 carbon atoms, unless otherwise specified.

The term "aryl" for $R^1$, $R^{1a}$ and $R^{1b}$ may include monocyclic aryl such as phenyl, tolyl, xylyl, cumenyl etc. and bicyclic aryl such as biphenylyl, naphtyl etc., preferably monocyclic aryl and naphthyl. The said aryl may optionally be substituted by one or more groups, preferably from one to three groups, selected from the group consisting of halogen such as fluorine, chlorine, bromine and iodine; hydroxy; lower alkoxy such as methoxy, ethoxy, propoxy, isopropoxy etc.; lower alkylenedioxy such as methylendioxy, ethylenedioxy; halo(-lower)alkyl such as trifluoromethyl, 2-chloroethyl; cyano; nitro; amino; mono-or di-(lower) alkylamino such as methylamino, ethylamino, dimethylamino; and acylamino, preferably lower alkanamido or lower alkoxycarbonylamino, such as acetamido, benzamido, methoxycarbonylamino etc.

The term "heteroxyclic group" for $R^1$ may include, for example, 5-membered monocyclic heterocyclic group containing 1 to 4 heteroatoms selected from oxygen, nitrogen and sulfur, such s furyl, thienyl, pyrrolyl, imidazolyl, thiazolyl, tetrazolyl etc.; 6-membered monocylic heterocyclic group containing 1 or 2 heteroatoms selected from oxygen, nitrogen and sulfur, such as pyridyl, piperidyl, piperadinyl, morpholinyl, thiomorpholinyl etc.; 7-membered monocyclic heterocyclic group such as azepinyl, diazepinyl etc.; and condensed heterocyclic group which is consisted of the monocyclic heterocycle as stated above and benzene nucleus condensed with each other, such as indolyl, indazolyl etc., preferably furyl, thienyl, pyrrolyl, pyridyl and indolyl. The said heterocyclic group may optionally, be substituted by one or more groups, preferably from one to three groups selected from lower alkyl such as methyl, ethyl, propyl, isopropyl etc. as well as halogen, hydroxy, lower alkoxy, lower alkylenedioxy, halo(lower)alkyl, cyano, nitro, amino, mono- or di-(lower) alkylamino and acylamino as stated above. The free bond of the heterocyclic group may be attached at any one of the possible positions.

When both $R^4$ and $R^5$ are hydrogen, the compound (I) represents the compound of the general formula (Ie), and when $R^4$ and $R^5$ together represent single bond, the compound (I) represents the compound of the formula (Id).

The term "halogen" for $R^2$ and $R^{2'}$ may include fluorine, chlorine, bromine and iodine.

The term "lower alkyl" for $R^2$ and $R^{2'}$ may include methyl, ethyl, propyl, isopropyl, butyl, isobutyl etc.

The term "lower alkoxy" for $R^2$ and $R^{2'}$ may include groups formed by combining lower alkyl groups as stated above with oxygen.

The term "functional derivative" of carboxy for $R^3$, $R^{3'}$, $R^{3a}$, $R^{3a'}$ may include esters and amides which are used for protection of carboxy group, as well as a compound of the general formula:

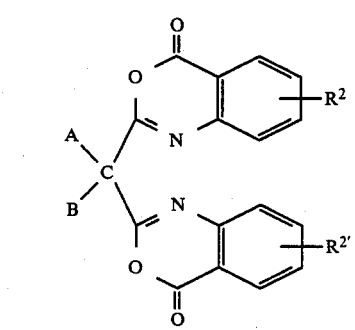

wherein $R^2$ and $R^{2'}$ are as defined above. Examples of the esters may include aliphatic esters, for example, lower alkyl ester such as methyl ester, ethyl ester, propyl ester, isopropyl ester, butyl ester, tert-butyl ester, pentyl ester, 1-cyclopropylethyl ester etc., lower alkenyl ester such as vinyl ester, allyl ester etc., lower lkynyl ester such as ethynyl ester, propynyl ester etc., lower alkoxy(lower)alkyl ester such as methyoxymethyl ester, 1-methyoxyethyl ester etc., lower alkylthio(lower)alkyl ester such as methylthiomethyl ester, ethylthiomethyl ester etc., halo(lower)alkyl ester such as 2-iodoethyl ester, 2,2,2-trichloroethyl ester etc., lower alkanesulfonyl(lower) alkyl ester such as mesylmethyl ester, mesylethyl ester etc., and aromatic esters, for example, optionally substituted aryl ester such as phenyl ester, tolyl ester, tert-butylphenyl ester, salicyl ester, 3,4-dimethyoxyphenyl ester etc., aryl(lower)alkyl ester such as benzyl ester, trityl ester, benzhydryl ester etc., as well as esters with silyl compound, for example, tri(lower)alkylsilyl esrer such as trimethylsilyl ester, triethylsilyl ester etc., di(lower)alkyl(lower)alkoxysilyl ester such as dimethylmethoxysilyl ester, and diethylmethoxysilyl ester etc.

The term "esterified carboxy" may include carboxy which is transformed into esters as stated above.

The groups $R^3$, $R^{3'}$, $R^{3a}$, $R^{3a'}$, $R^{3b}$ and $R^{3b'}$ may preferably attached at ortho-position in relation to the carbamoyl group.

The term "residue derived from alcohol having two or more carbon atoms by removing hydroxy group" may include alkyl group having two or more carbon aroms as well as alkyl group having one more carbon atoms which is substituted by non-alkyl substituent(s) having one or more carbon atoms. The said "alkyl group having two or more carbon atoms" may include lower alkyl group having two or more carbon atoms, preferably 2 to 8 carbon atoms, more preferably 2 to 6, or 2 to 5, or 2 to 4 carbon atoms, such as ethyl, propyl, isopropyl, butyl, isobutyl, sec-butyl, tert-butyl, pentyl, hexyl, heptyl, octyl etc. In the said "lower alkyl group having one or more carbon atoms which is substituted by nonalkyl substituent(s) having one or more carbon atoms", the term "non-alkyl substituent" may include groups containing heteroatoms such as oxygen, nitrogen, sulfur etc. which is combined directly or with intermediation of unsaturated group to the said alkyl group having one or more carbon atoms, and may also include aryl group. Example of preferable heteroatom is ester-oxygen e.g. cf carboxylic ester or carbonic ester). The said ncn-alkyl substituent(s) is preferably attached at the alpha-carbon atom of the said alkyl group. These no alkyl and alkyl groups preferably contain 1 to 10, especially 1 to 9, carbon atoms. Suitable examples of lower alkyl group having one or more carbon atoms which is substituted by non alkyl substituent(s) having one or more carbon atoms are acetoxymethyl, pivaloyloxymethyl, 1-(ethxycarbonyloxy)ethyl, 3-phthalidyl, 2-(3-phthalidylidene)ethyl, (5-methyl-2-oxo-1,3-dioxole-4-yl)methyl etc. and groups which form physiologically hydrolyzable esters.

It is to be understood that, when the compound (I) or (I') has the chirality, the formula (I) or (I') includes all the isomers and mixtures thereof. It is also to be understood that, in the formula (Ik), two groups R may be identical or different and, when they are different, both of two isomers formed by geometry of $-CH=C<$ double bond are included in the formula (Ik). Further, when these compounds show crystalline polymorphism or contain water or solvent of crystallization, all the crystal froms and crystals having such water or solvent are included in the scope of the present invention.

The processes for preparing the compound (I) are explained in details in the following.

Process (a)

The compound (Ib) can be obtained by converting the group $R^{3a}$ and $R^{3a'}$ in the compound (Ia) into carboxy groups according to the conventional method. Any method conventionally used for removal of carboxy-protecting group such as hydrolysis, reduction etc. can be adopted as a method for the conversion.

The hydrolysis includes acidic hydrolysis and basic hydrolysis. Examples of acids used for acidic hydrolysis include inorganic and organic acids such as hydrochloric acid, formic acid, trifluoroacetic acid, benzenesulfonic acid, cation exchanger resin etc. Examples of bases used for basic hydrolysis include inorganic and organic bases such as alkali metal hydroxide e.g. sodium hydroxide, potassium hydroxide etc., alkali metal carbonate e.g. sodium carbonate, potassium carbonate etc., picoline, 1,5-diazabicyclo[4,3,0]-5-nonene, anion exchanger resin etc. The hydrolysis may be carried out in a solvent, examples for which include water, and a mixture of water and a hydrophylic organic solvent such as methanol, ethanol, tetrahydrofuran etc. The hydrolysis may also be carried out by solvolysis.

Process (b)

The compound (Id) can be obtained by reacting the compound (Ic) or its metal salt with the compound (II). The metal salt of the compound (Ic) can be prepared by reacting the compound (Ic) with alkali metal alkoxide. When the compound (Ic) is used without converting into its metal salt, the reaction is carried out in the presence of a base or a Lewis acid. Common organic or inorganic base such as pyridine, picoline, piperidine, morpholine etc. can be used. As the Lewis acid, boron trifluoride (etherate) titanium tetrachloride, zirconium tetrachloride, aluminum trichloride, tin tetrachloride, zinc dichloride etc. are used. The reaction is usually carried out in a solvent. Examples of the solvent include xylene, toluene, dioxane, dimethylformamide, dimethylsulfoxide etc. and any liquid base can serve as the solvent. The reaction is normally effected with heating.

A preferable example of operation is as follows. The compound (Ic) and 1,5 times by mole of the compound (II) is reacted under reflux in pyridine for 16–63 hours. After removing pyridine, the residue is treated under water, alkalinized by adding 10% aqueous ammonia under ice cooling and extracted with ether to remove the compound (II). The aqueous phase is acidified and crystals which appear are purified by column chromatography, recrystallization etc. to give the compound (Id).

The compound (Ic) can be prepared by the process (d) described infra (wherein A and B represent hydrogen).

The compound (II) is either the known compound commercially available or one which can be prepared by a method similar to that for production of the known compound.

Process (c)

The compound (Ie) can be obtained by reducing the compound (Id) according to the conventional method.

The reduction may either be effected by catalytic reduction or by chemical reduction. Tne catalytic reduczion is carried out by reacting hydrogen in a solvent such as methanol, ethanol, dioxane etc. in the presence of metal catalyst for catalytic reduction such as platinum oxide, palladium on carbon, rhodium on alumina etc. The chemical reduction can be effecting using reducing agent such as sodium borohydride-nickel chloride system in a solvent such as methanol, ethanol etc.

The compound (Id) is prepared by the process (b) described supra.

Process (d)

The compound (Ia) can be obtained by reacting simultaneously or stepwisely the compound (III) or reactive derivative at the carbcxy group thereof with the compound (IV) and (IV') or reactive derivatives at the amino groups thereof.

When $R^2$ and $R^3$ in the compound (IV) are identical to $R^{2'}$ and $R^{3'}$ in the compound (IV'), respectively, formulae (IV) and (IV') represent the same compound.

The reactive derivative at the carboxy group of the compound (III) includes acid halides, acid anhydrides, activated esters and activated amides. Among the acid halides, acid chloride is the most frequently used. Examples of the acid anhydrides include dialkylphosphoric acid mixed anhydride, dialkylphosphorous acid mixed anhydride, alkylcarbonic acid mixed anhydride, aliphatic carboxylic acid (e.g. pivalic acid, trichloroacetic acid) mixed anhydride etc. Examples of the activated esters include methyl ester, ethyl ester, cyanomethyl ester, p-nitrophenyl ester, an ester with N-hydroxysuccinimide etc. Examples of the activated amides include an amide with imidazol, dimethylimidazol or triazol. When this reaction is carried out stepwisely, two groups selected from carboxy or its reactive derivative are preferably different.

The reactive derivative at the amino group of the compound (IV) or (IV') includes a Schiff's base with an aldehyde (e.g. acetaldehyde, isopentanal, benzaldehyde), a reaction product with a silyl compound (e.g. trimethylsilyl chloride, trimethylsilylacetamide), a reaction product with a phosphorus compound (e.g. phosphorus trichloride, phosphorus oxychloride).

When the compound (III) is used in the form of carboxylic acid, it is advantageous to carry out the reaction in the presence of condensing agent. Examples of the condensing agent include N,N'-dicyclohexyl carbodiimide, N-cyclohexyl-N'-morpholinoethyl carbodiimide, N,N'-diisopropyl carbodiimide, N-ethylbenzisoxazolium salts, 2-chloro-1-methylpyridinium salt, N,N'-carbonyl diimidazol, phosphorus trichloride, phosphorus oxychloride etc.

The reaction is usually carried out in a solvent. Examples of the solvent include dioxane, methylene chloride, tetrahydrofuran, dimethylformamide, pyridine, benzene, toluene, xylene etc.

A preferable example of operation is as follows. Diethylester of the compound (III) and two times by mole of the compound (IV=IV') are heated in dry oxylene under reflux for 20-48 hours. Crystals, if formed (when $R^3=R^{3'}=COOH$), are filtered and if there is no crystal formation, the solvent is distilled off. Alternatively, the compound (IV=IV') is dissolved in dry dioxane and 1/2.66 times by mole of chloride of the compound (III) is added dropwise thereto. The mixture is stirred overnight.

The compound -(III) and the compound (IV) or (IV') are either the known compound commercially available, or those which can be prepared by a method similar to that for production of the known compound.

Process (e)

The compound (If) can be obtained by esterifying the compound (Ib).

The esterification is carried out by reacting the compound (Ib) or a reactive derivative at the carboxy group thereof with an appropriate alcohol or a reactive derivative thereof. Examples of the reactive derivative at the carbcxy groups of the compound (Ib) may be derivatives similar to those exemplified for the reactive derivative of the compound (III) and intramolecular cyclic anhydride formed by imidating the amido moiety, i.e.. the compound of the formula:

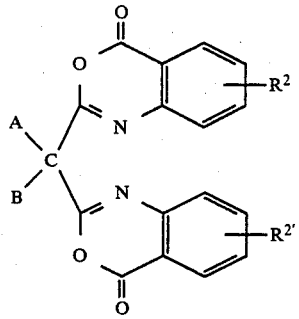

Examples of the reactive derivative of alcohol include active ester of the alcohol such as alkyl halide, alkyl sulfate etc. This reaction is carried out in a manner similar to that in the process (d). Especially desirable method is a reaction using alkyl halide in the presence of a base such as potassium carbonate and a solvent such as dimethylformamide, dioxane, hexamethylphosphoramide etc.

In a particular example, a compound of the formula:

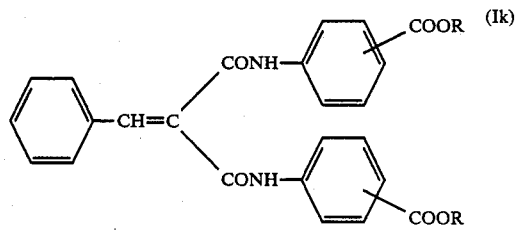

wherein R is residue derived from alcohol having two or more carbon atoms by removing hydroxy group, is prepared by reacting a compound of the formula:

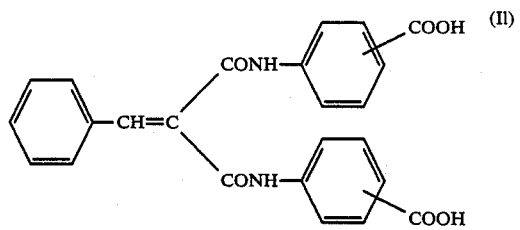

or a reactive derivative at the carboxy groups thereof wirh a hydroxy compound of the formula:

R—OH wherein R is as defined above, or a reactive derivative at the hydroxy group thereof.

Examples of the reactive derivative at the carboxy groups of the compound (II) include acid halides, acid anhydrides, activated esters and activated amides. Among the acid halides, acid chloride is the most frequently used. Examples of the acid anhydrides include symmetric anhydride, an intramolecular cyclic anhydride formed by imidating the amido moeity, i.e. the compound of the formula:

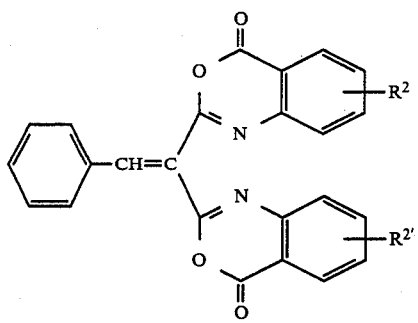
(Va)

and mixed anhydrides, examples for which are dialkylphosphoric acid mixed anhydride, dialkylphosphorous acid mixed anhydride, alkylcarbonic acid mixed anhydride, aliphatic carboxylic acid (e.g. pivalic acid, trichloroacetic acid) mixed anhydride etc. Examples of the activated esters include cyanomethyl ester, p-nitrophenyl ester, an ester with N-hydroxysuccinimide etc. Examples of the activated amides include an amide with imidazol, dimethylimidazol or triazol.

Examples of the reactive derivative at the hydroxy group of the hydroxy compound include halide, inorganic acid esters such as sulfate etc. organic acid esters such as methanesulfonic acid ester, toluenesulfonic acid ester etc., alkaline metal salzs and diazo-compounds. They can be represented by the formula:

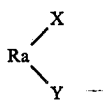

wherein Ra is a residue derived from R by removing one hydrogen attached to alpha-carbon atom, one of X and Y is hydrogen and the other is a reactive group or X and Y together form a group=$N_2$. The reactive group means a group which can be easily left by the reaction.

When the compound (II) is used in the form of carboxylic acid, it is advantageous to carry out the reaction in the presence of condensing agent. Examples of the condensing agent include N,N'-dicyclohexyl carbodiimide, N-cyclohexyl-N'-morpholinoethyl carbodiimide, N,N'-diisopropyl carbodiimide, N-ethylbenzisoxazolium salts, 2-chloro-1-methylpyridinium salt, N,N'-carbonyl diimidazol, phosphorus trichloride, phosphorus oxychloride etc.

In some cases, it is favorable to carry out the reaction in the presence of a base.

The reaction is usually carried out in solvent. Examples of the solvent include dioxane, methylene chloride, tetrahydrofuran, dimethylformamide, pyridine, benzene, toluene, xylene etc.

Suitable reactive derivative at the carboxy groups of the compound (II), reactive derivative at the hydroxy group of the hydroxy compound R—OH, condensing agent, base, solvent etc. can be selected according to R in the desired compound (Ik). For example, where the group R is ethyl, propyl, isopropyl etc., the compound (II) is preferable reacted with a compound R—$X_1$ wherein $X_1$ is halogene, preferably iodine in the presence of potassium (or sodium) carbonate as the base. Where the group R is 3-phthalidyl, 2-(3-phthalidylidene)ethyl, pivaloyloxymethyl, 1-(2-ethoxycarbonyloxy)ethyl, (5-methyl-2-oxo-1,3-dioxole-4-yl)methyl etc., the compound (II) is preferably reacted with the compound R—$X_1$ wherein $X_1$ is halogen in the presence of organic tertiary amine (e.g. triethylamine) as the base. In these cases, it is preferable to carry out the reaction in the presence of iodide (e.g. sodium iodide) when $X_1$ is chlorine. Where the group R is isopropyl, tertiary butyl etc., it is preferable to use the compound (Va) as the reactive derivative of the compound (II), which is preferably reacted with a compound R—$X_2$ wherein $X_2$ is alkali metal, preferably lithium, sodium or potassium.

Process (f)

The compound (Ih) can be obtained by lower-alkylating the compound (Ig).

The lower-alkylation is effected according to the conventional method using a lower-alkylating agent such as methyl chloride, methyl iodide, ethyl bromide etc. This reaction is preferably carried out in the presence of a base.

When the compound (Ig) has a group being easily alkylated, such as carboxy, the said group is occasionally lower-alkylated in the course of the reaction, and such case is also included in the scope of the present invention.

The compound (Ig) is prepared by the processes (a) to (e) described supra (wherein $R^1$ is aryl substituted by hydroxy).

Process (g)

The compound (Ij) can be obtained by lower-alkylating the compound (Ii).

This process is conducted in a manner similar to that for the prccess (f). Examples of preferable bases include strong bases such as sodium hydride, sodium amide, sodium alkoxide etc.

The ccmpound (Ii) is prepared by the process (a) to (e) described supra (wherein $R^1$ is pyrrolyl or indolyl).

Process (i)

The compound (Im) can be obtained by reacting the compound (II) or a reactive derivative at the carboxy groups thereof with a methylating agent.

This reaction is conducted in a manner similar to that in the process (e).

Examples of the reactive derivative at the carboxy groups of the compound (II) include acid halides, acid anhydrides, acivated esters and activated amides. Among the acid halides, acid chloride is the most frequently used. Examples of the acid anhydrides include symmetric anhydride, an intramolecular cyclic anhydride formed by imidating the amido moeity, i.e. the compound of the formula:

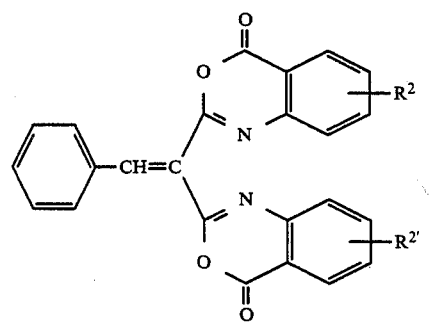
(Va)

and mixed anhydrides, examples for which are dialkylphosphoric acid mixed anhydride, dialkylphosphorous acid mixed anhydride, alkylcarbonic acid mixed anhydride, aliphatic carboxylic acid (e.g. pivalic acid, trichloroacetic acid) mixed anhydride etc. Examples of the activated esters include cyanomethyl ester, p-nitrophenyl ester, an ester with N-hydroxysuccinimide, trimethylsilylester etc. Examples of the activated amides include an amide with imidazol, dimethylimidazol or triazol.

As the methylating agent, methanol and reactive derivatives at the hydroxy group thereof can be used. Examples of the reactive derivative at the hydroxy group of methanol include halides, inorganic acid esters such as, sulfate etc., organic acid esters such as methanesulfonic acid ester, toluenesulfonic acid ester etc., alkaline metal salts and diazo-compounds. They can be represented by the formula:

wherein one of X and Y is hydrogen and the other is a reactive group or X and Y together form a group $=N_2$. The reactive group means a group which can be easily left by the reaction.

When the compound (II) is used to react with methanol in the form of carboxylic acid, it is advantageous to carry out the reaction in the presence of condensing agent. Examples of the condensing agent include N,N'-dicyclohexyl carbodiimide, N-cyclohexyl-N'-morpholinoethyl carbodiimide, N,N,-diisopropyl carbodiimide, N-ethylbenzisoxazolium salts, 2-chloro-1-methylpyridinium salt, N,N'-carbonyl diimidazol, phosphorus trichloride, phosphorus oxychloride etc.

When the compound X—CH$_2$—Y wherein X or Y is a reactive group selected from acid residue is used, it may be preferable to carry out the reaction in the presence of the base including inorganic base such as sodium carbonate, potassium carbonate etc. or organic base such as triethyl amine, pyridine etc.

The reaction is usually carried out in solvent. Examples of the solvent include dioxane, methylene chloride, tetrahydrofuran, dimethylformamide, pyridine, benzene, toluene, xylene etc.

In this reaction, suitable compound (II) or the reactive derivative at the carboxy groups thereof, methylating agent and reaction conditions can be selected according to the reactant. For example, where the compound (II) is used in the form of carboxylic acid, it is preferable to select the compound CH$_3$—X$_1$ wherein X$_1$ is halogen, preferably iodine, as the reactant. In this case, the reaction is preferably carried out in the presence of the base (e.g. alkali metal carbonate). It is also preferable to carry out the reaction in the presence of iodide (e.g. sodium iodide) when X$_1$ is chlorine. Where the compound (Va) is used as the reactive derivative of the compound (II), it is preferable to select a compound CH$_3$—OX$_2$ wherein X$_2$ is alkaline metal, preferably lithium, sodium or potassium, as the methylating agent.

Process (ii)

The compound (Im) can be obtained by reacting the compound (In) or the metal salt thereof with benzaldehyde.

This reaction is conducted in a manner similar to that in the process (b).

The metal salt of the compound (In) can be obtained, for example, by reacting the compound (In) with alkali metal alkoxide. When the compound (In) is used without converting into its metal salt, the reaction is carried out in the presence of a base or a Lewis acid. Common organic or inorganic base such as pyridine, picoline, piperidine, morpholine etc. can be used. As the Lewis acid, boron trifluoride (etherate) titanium tetrachloride, zirconium tetrachloride, aluminum trichloride, tin tetrachloride, zinc dichloride etc. are used. The reaction is usually carried out in a solvent. Examples of the slovent include xylene, toluene, dioxane, dimethylformamide, dimethylsulfoxide etc. and any liquid base can serve as the solvent. The reaction is normally effected with heating.

Process (A)

The compound (V) can be obtained by subjecting the compound (Ip) to dehydrating reaction.

The dehydrating reaction may be carried out by heating in a non-aqueous solvent preferably with distilling-out of water, or by treating with dehydrating agent. Examples of the dehydrating agent include organic and inorganic acid halides such as oxalyl chloride, benzoyl chloride, phosphorus trichloride, phosphorus oxychloride, thionyl chloride etc., organic and inorganic acid anhydrides such as trifluoroacetic anhydride, phosphorus pentoxide, polyphosphoric acid etc., dehydrating condensing agent such as N,N,-dicyclohexylcarbodiimide, N-cyclohexyl-N'-morpholinoethylcarbodiimide, N,N'-diisopropylcarbodiimide, N-ethylbenzoisoxazolium salt, 2-chloro-1-methylpyridimium salt, N,N'-carbonyldiimidazol, N,N'-thionyldiimidazol etc. and drying agent such as molecular sieve. The reaction is normally carried out in a solvent such as benzene, toluene, dimethylformamide, methylene chloride etc. Reaction temperature varies depending on the dehydrating agent and is normally between from room temperature to boiling point of the solvent.

Process (B)

The compound (V) can be obtained by reacting the compound (VI) with the compound R$^1$—CHO.

This reaction is conducted in a manner similar to that in the process (b).

The reaction may be carried out in the presence of Lewis acid. As the Lewis acid, boron trifluoride (etherate), titanium tetrachloride, zirconium tetrachloride, aluminum trichloride, tin tetrachloride, zinc dichloride etc. are used. The reaction is usually carried out in a solvent. Examples of the solvent include xylene, toluene, dioxane, dimethylsulfoxide etc. The reaction is normally effected with heating. The starting compound (VI) is prepared by a process similar to the process (A) from 2,2'-[(1,3-dioxo-1,3-propanediyl)diimino]bis benzoic acid.

It has been discovered by the inventors that some of the compound (I) or (I'), i.e. the compounds (Io)

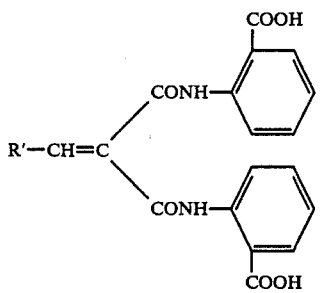

(Io)

wherein R' is phenyl, 2-thienyl, 3-thienyl or 1-methyl-2-pyrrolyl, show a violent variation in melting point even if they are crystals obtained after a sufficient purification. Since this variation does not accompany a variation in purity, it is clear that the variation is not based on degradation of the compounds in question. Such variation in melting point is extremely inconvenient because it has adverse effects on slability and unity of formulations when the said compounds are formed into solid formulation such as tablets, powders, granules etc.

After extensive study on the case for the variation in melting point and method for preventing the same, the inventors discovered that the compounds showing such variation may be present in a lower melting point form (unstable form) and a higher melting point form (stable form), and the lower melting form can be converted into the higher melting form by subjecting to the treatment in which frictional forces act upon the lower melting point form. Such treatment includes crushing in a porcelein mortar or on a clay plate, pressing through a sieve, pressing in a vessel such as a filter, pressing into tablets, shaking in a mixer and grinding. The obtained higher melting point form does not change of itself into the lower melting point form. The higher melting point form does not cause problem on preparing solid formulations such as powders, granules, tablets etc. and can provide stable formulatins.

The lower melting point form of the compound (Io) is specified as follows.

The compound (Io) wherein R' is phenyl [(herein after referred to as the compound $(I_o{}^a)$] in lower melting point form can be obtained by recrystallizing the compound $(I_o{}^a)$ in an arbitrary form from methanol-water system and has the following physico-chemical properties.

melting point: 195°–196° C. (monohydrate)
IR(KBr, cm$^{-1}$): 3500, 2300–3300, 1680
NMR(DMSO-d$_6$,delta): 12.00 (1H, s, —CON$\underline{H}$—), 11.7 (1H, s, —CONH—), 8.7–7.1 (m, aromatic $\underline{H}$)

The compound (Io) wherein R' is 2-thienyl [(herein after referred to as the compound $(I_o{}^b)$] in lower melting point form can be obtained by recrystallizing the compound $(I_o{}^b)$ in an arbitrary form from methanol-water system and has the following physico-chemical properties.

melting point: 213°–215° C. (monohydrate)
IR(KBr, cm$^{-1}$): 3450, 2300–3300, 1680
NMR(DMSO-d$_6$, delta): 12.0 (2H, s, —CONH—), 8.7–7.0 (m, aromatic H)

The compound (Io) wherein R' is 3-thienyl [(herein after referred to as the compound $(I_o{}^c)$] in lower melting point form can be obtained by recrystallizing the compound $(I_o{}^c)$ in an arbitrary form from methanol-water system and has following physico-chemical properties.

melting point: 210°–212° C. (monohydrate)
IR(KBr, cm$^{-1}$): 3450, 2300–3300, 1680
NMR(DMSO-d$_6$, delta): 12.0 (1H, s, —CON$\underline{H}$—), 11.8(1H, s, —CON$\underline{H}$), 8.7–7.1 (m, aromatic H)

The compound (Io) wherein R' is 1-methyl-2-pyrrolyl [(herein after referred to as the compound $(I_o{}^d)$] in lower melting point form can be obtained by recrystallizing compound $(I_o{}^dd)$ in an arbitrary form from methanol-water system and has the following physico-chemical properties.

melting point: 206°–209° C. (monohydrate)
IR(KBr, cm$^{-1}$): 2300–3300, 1680
NMR(DMSO— d$_6$, delta): 11.9 (1H, s, —CON$\underline{H}$—), 11.8 (1H, s, —CONH—), 8.8–6.0 (m, aromatic H), 3.8(1H, s, —NC$\underline{H}_3$)

The compound (Io) can be prepared by the following process.

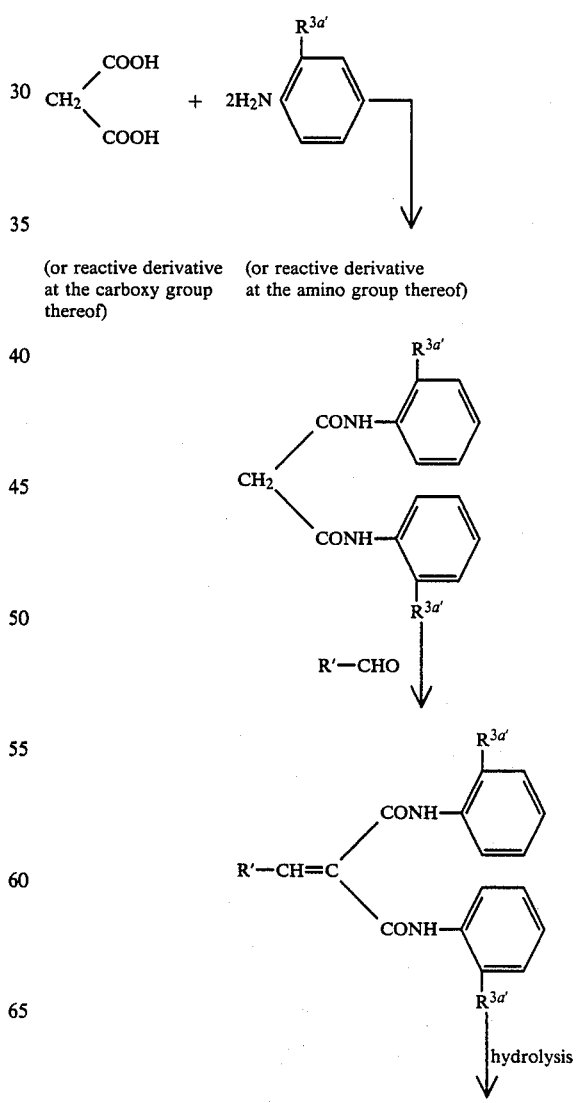

-continued

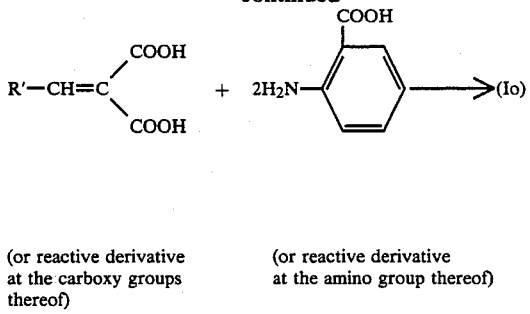

(or reactive derivative at the carboxy groups thereof)    (or reactive derivative at the amino group thereof)

When the groups R³ and/or R³' in the compound (I) or (I') is carboxy, any salts of such compound are also included within the scope of the invention. Examples of the salts include those with alkali metals such as sodium, potassium etc., alkali earth metals such as calucium, magnesium etc., other metals such as aluminum, organic amines such as ethanolamine, diethanolamine, pyrrolidine, piperidine, morpholine, N-methylpiperazine, N-hydroxyethylpiperazine, and amino acids such as lysine, arginine, ornitine, histidine, etc. These salts can be obtained by reacting the appropriate free carboxylic acid with the appropriate base.

In the compound (I) or (I') having carboxy group as R³ and/or R³', when said compound is not satisfactory in property such as solubility, stability, absorbability etc., a modified compound having improved properties may be obtained by converting the carboxy group in the original compound into a pharmaceutically acceptable derivative (i.e. bioprecursor). Such improved compound, when administered, is converted into the original carboxy compound in the body. Examples of these compound include those having pharmaceutically acceptable, physiologically hydrolyzable ester as R³ and R³'. The esters include methyl ester, ethyl ester, isopropyl ester, tert-butyl ester, acetoxymethyl ester, 1-(ethoxycarbonyloxy)ethyl ester, pivaloyloxymethyl ester, phthalidyl ester, 5-indanyl ester, 2-(3-phthalidylidene)ethyl ester, (5-methyl-2-oxo-1,3-dioxole-4yl)methyl ester etc.

The compounds of the formula (I') have been shown to have anti-hyaluronidase, antiallergic and antiulcerous activities and accordingly are useful as medicine. Preferable compounds are those wherein both A and B are other than hydrogen. Also, preferable compounds are those wherein groups R³ and R³' are attached at ortho-position to the carbamoyl (—CONH—) groups. In addition, the compounds (I) have an advantage that they are less toxic.

For example, the compounds (Ik), (Im) and (V) have the allergic activity. It is considered that these compounds are converted in the body to the parent compounds having free carboxyl groups, however, in some cases the compounds (Ik), (Im) and (V) are superior to the parent compounds in solubility, stability, absorbability etc. and accordingly show an excellent effect.

For the above usages, the required dose will, of course, vary depending on the compound actually used, the mode of administration and treatment desired. In general, however, satisfactory results are obtained in administration at a dosage from 1 to 6 mg/kg conveniently administered in 2 to 4 divided dosages a day or in sustained release form.

For prophylactic and/or therapeutic administration, the compound according to the invention can be used in a form of conventicnal pharmaceutical preparation which contains the said compound, as an active ingredient, in admixture with pharmaceutically acceptable carriers such as organic or inorganic, solid or liquid excipient which is suitable for oral, parenteral or external administration. The pharmaceutical preparation may be in solid forms such as capsule, tablet, sugar coated tablet, ointment, suppository etc. or in liquid forms such as solution, suspension, emulsion etc. These preparations also may contain auxiliary substance, stabilizer, humectant, emulsifier, buffer and other conventional additives.

Practical and preferred embodiments of the present invention are illustrated in further detail by the following Examples and Test Examples. In the following experiments, there were used Art 5735 made by Merck as silica gel for TLC and Art 7734 made by Merck as silica gel for column chromatography.

EXAMPLE 1

Preparation of 2,2'-[(1,3-dioxo-1.3-propanediyl)diimino]bisbenzoic acid (Compound 01) (Process d)

Diethyl malonate (3.48 g, 21.7 mmol) and anthranilic acid (6.0 g, 43.7 mmol) were heated under reflux in dry xylene (120 ml)for 40 hours. The precipitated crystals were filtered while hot and washed with acetone to give white crystals of the title compound (6.19 g, 83.2%). m.p., 254°–258° C.

EXAMPLE 2

Preparation of 4,4'-dinitro-2,2'-[(1,3-dioxo-1,3-propanediyl)diimino]-bisbenzoic acid (Compound 06) (Process d)

4-Nitroanthranilic acid (5.0 g, 26.6 mmol) was dissolved in dry dioxane (130 ml). To this solution, a solution of malonyl dichloride (1.45 g)in dry dioxane (5 ml)was added dropwise at room temperature. After stirring the mixture overnight, the precipitated crystals were collected by filtration, and washed with water and ether to give a pale yellow crystals of the title compound (2.58 g, 89.8%). m.p., 269°–270.5° C.

EXAMPLE 3

Preparation of 4-chloro-2,2'-[(1,3-dioxo-1,3propanediyl)diimino]bis-benzoic acid (Compound 09) (Process d)

To the solution of anthranilic acid (1.824 g, 13.3 mmol) in dry dioxane (65 ml), ethyl malonyl chloride (1.001 g, 0.851 ml, 6.65 mmol) in dry dioxane (2.5 ml) was added dropwise at room temperature and the mixture was stirred at room temperature for 3 hours, then at 50° C. for 1 hour. After the reaction, the precipitated solid matter was filtered, and the solvent was removed from the filtrate under reduced pressure. The residue was dissolved by the addition of ethyl acetate and washed with 1 N.HCl to remove anthranilic acid. Then the organic layer was washed with water and dried. Ethyl acetate was evaporated under reduced pressure to give a yellow oil. The obtained oil was purified by applying on a silica gel column [(developing solvent: ethyl acetate:benzene =1:1 (containing 1% acetic acid)], from which the third, colorless fraction was collected to give O-ethyl malonyl aminobenzoic acid in pale yellow oil. The oil was treated with ethyl acetate, washed and dried. The solvent was evaporated to give an intermediate product of O-ethyl malonyl aminobenzoic acid in pale yellow solid (721 mg, 43%). m.p., 103°–104° C.

The thus obtained intermediate (500 mg, 1.99 mmol) and 4-chloro-anthranilic acid (341 mg, 1.99 mmol) were refluxed in dry xylene (13 ml) for 14 hours. The precipitated crystals were filtered while hot and washed with acetone to give the title compound as white crystals (483 mg, yield, 64.5%). m.p., 259°–261° C.

EXAMPLE 4

Preparation of
2,2'-[(1,3-dioxo-2-phenylmethylene-1,3-propanediyl)-diimino]bisbenzoic acid (Compound 11) (Process b)

2,2'-[(1,3-Dioxo-1,3-propanediyl)diimino]bisbenzoic acid (1.0 g) and benzaldehyde (0.46 g, 1.5 mol equivalent) were heated under reflux in dry pyridine (8 l) for 16 hours. After removing pyridine, the mixture was treated with water, made alkaline with 10% aqueous ammonia under ice cooling, and the aqueous layer was washed with ether. The aqueous layer was made acidic (pH=2) with 1N HCl, and the precipitated crystals were collected by filtration. After washing with water, the resulting solid was purified by dissolving in tetrahydrofuran, adsorbing on the silica gel column and separating the desired compound using a developing solvent [ethyl acetate:benzene=1:1 (containing 1% acetic acid)]. After removing the initially eluted impurities, the solvent was removed from the effluent out liquid containing the desired compound. The residue was crystallized by adding water, collected on a filter, washed with water, and dried to give the title compound (0.686 g, yield, 51%), which was recrystallized from the mixed solvent of $CH_3OH$—$H_2O$ system to obtain pale yellow crystals of monohydrate (Crystal a, 0.507 g) (Drying: 1 mm Hg, 100° C., 15 hours), m.p., 195°–196° C.

Elementary analysis: Calcd. for $C_{24}H_{18}N_2O_6 \cdot H_2O$: C64.28, H4.50, N6.25. Found: C64.23, H4.50, N6.25.

Rf=0.53 [Ethyl acetate:benzene=1:1 (containing 1% acetic acid)

IR(KBr, cm$^{-1}$):3500 (—CON$\underline{H}$—), 2300–3300(—COOH), 1680(—$\underline{C}$ONH—) (FIG. 1)

Figure 2:
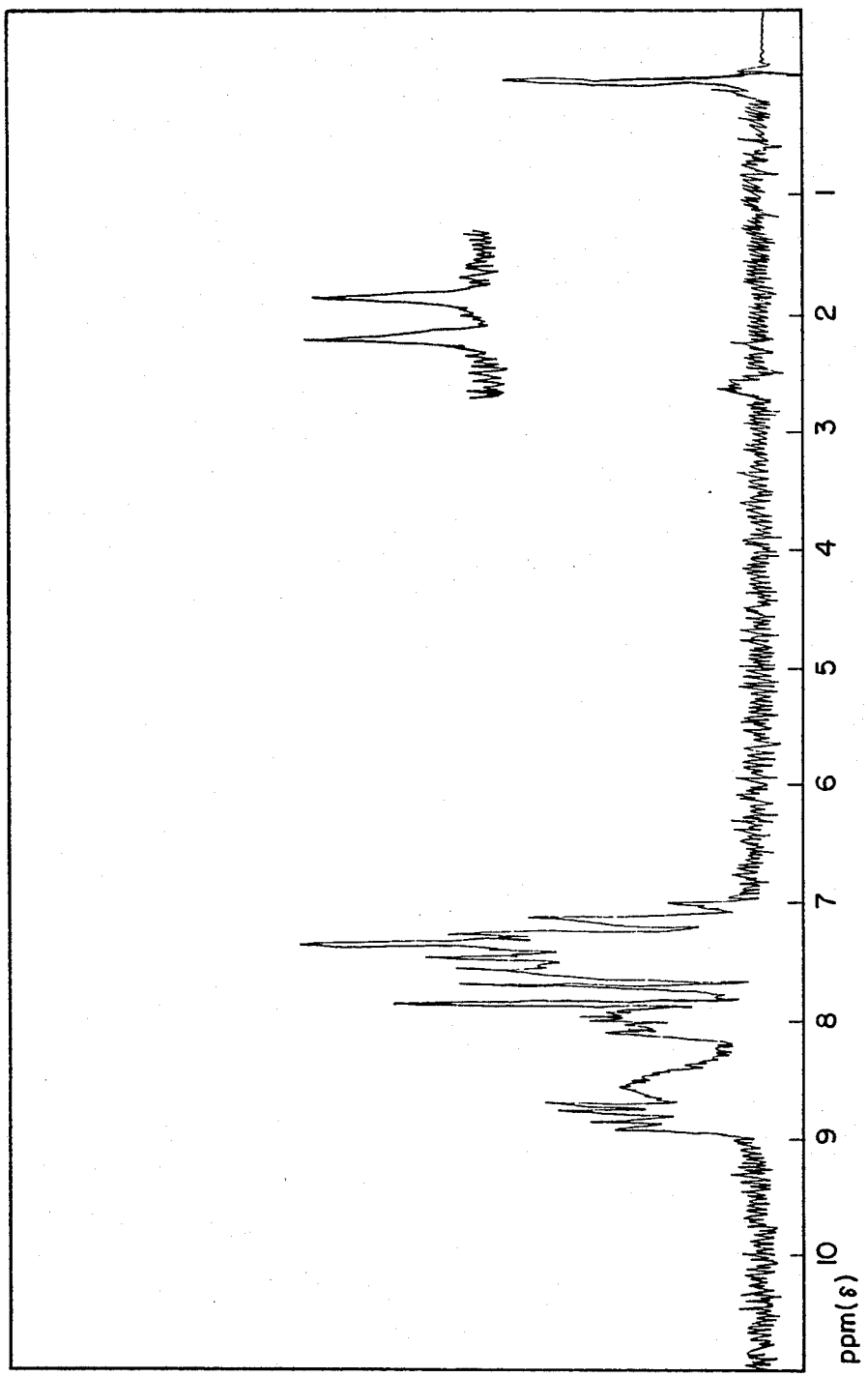

$^1$H-NMR(DMSO-d$_6$, δ): 12.00 (s,1H, —CON$\underline{H}$—), 11.7 (s, 1H, —CON$\underline{H}$—), 8.7–7.1 (m, aromatic hydrogen) (FIG. 2; solvent is CDCl$_3$: DMSO-d$_6$=3:1)

MS (m/e):412 (M+-18)

Recrystallization by the use of $CH_3OH$ in place of $CH_3OH$—$H_2O$ system gave crystals of ½ hydrate (Crystal b), m.p., 195°–196° C.

Elementary analysis: Calcd. for $C_{24}H_{18}N_2O_6 \cdot \frac{1}{2}H_2O$: C65.60, H4.32, N6.38. Found: C65.44, H4.47, N6.39.

In another run, the eluent from the column gave, on removal of solvent and addition of water, crystals, which were re-crystallized from $CH_3OH$, followed by re-crystallization from $CH_3OH$—$H_2O$ giving the crystals of m.p., 247°–249° C. (Crystal c).

Elementary analysis: Calcd. for $C_{24}H_{18}N_2O_6 \cdot H_2O$: C64.28, H4.50, N6.25. Found: C64.28, H4.36, N6.45.

Figure 3:
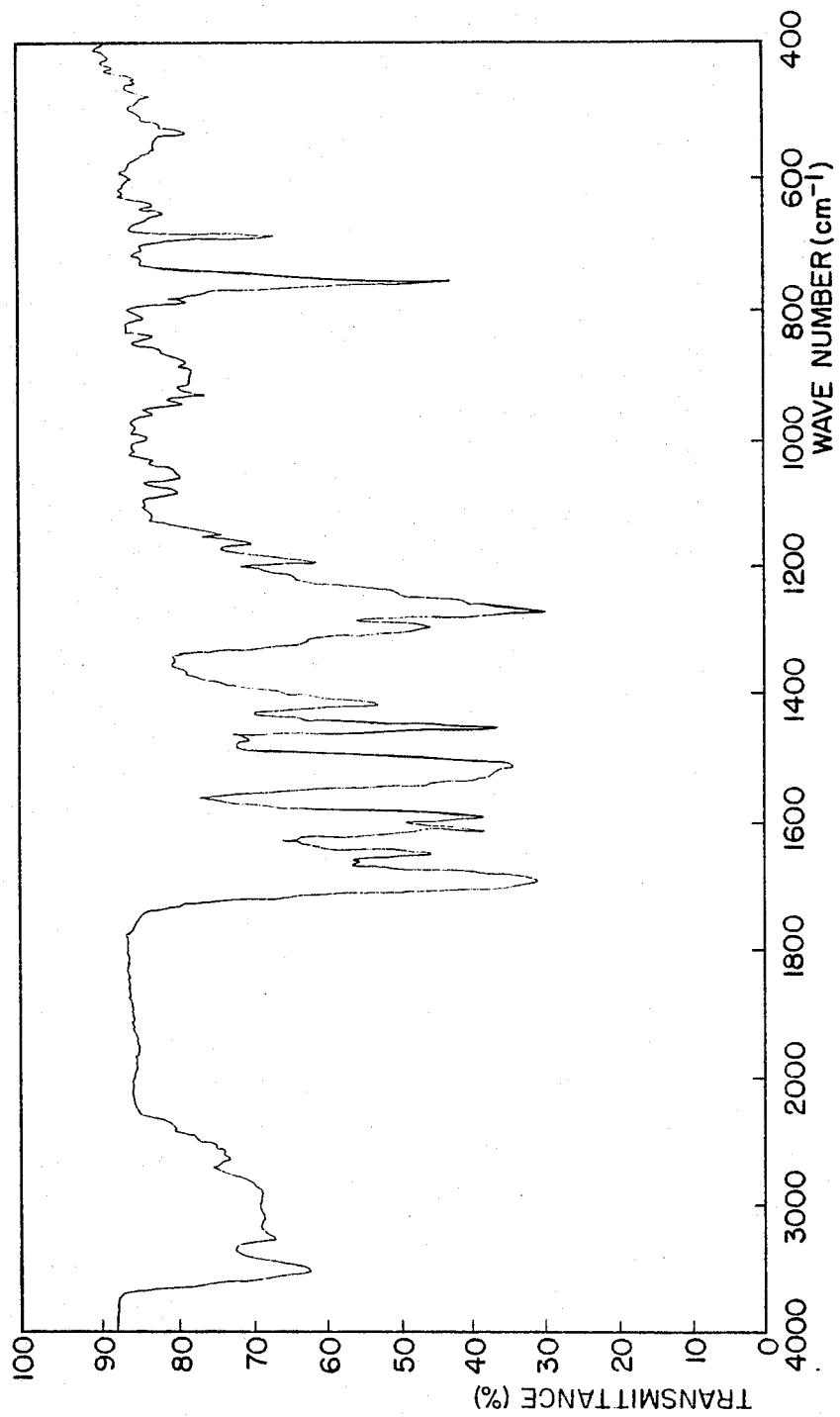

IR(KBr, cm$^{-1}$) 3500(—CON$\underline{H}$—), 2300–3300-(COOH), 1680(—$\underline{C}$ONH—) (FIG. 3)

Figure 4:
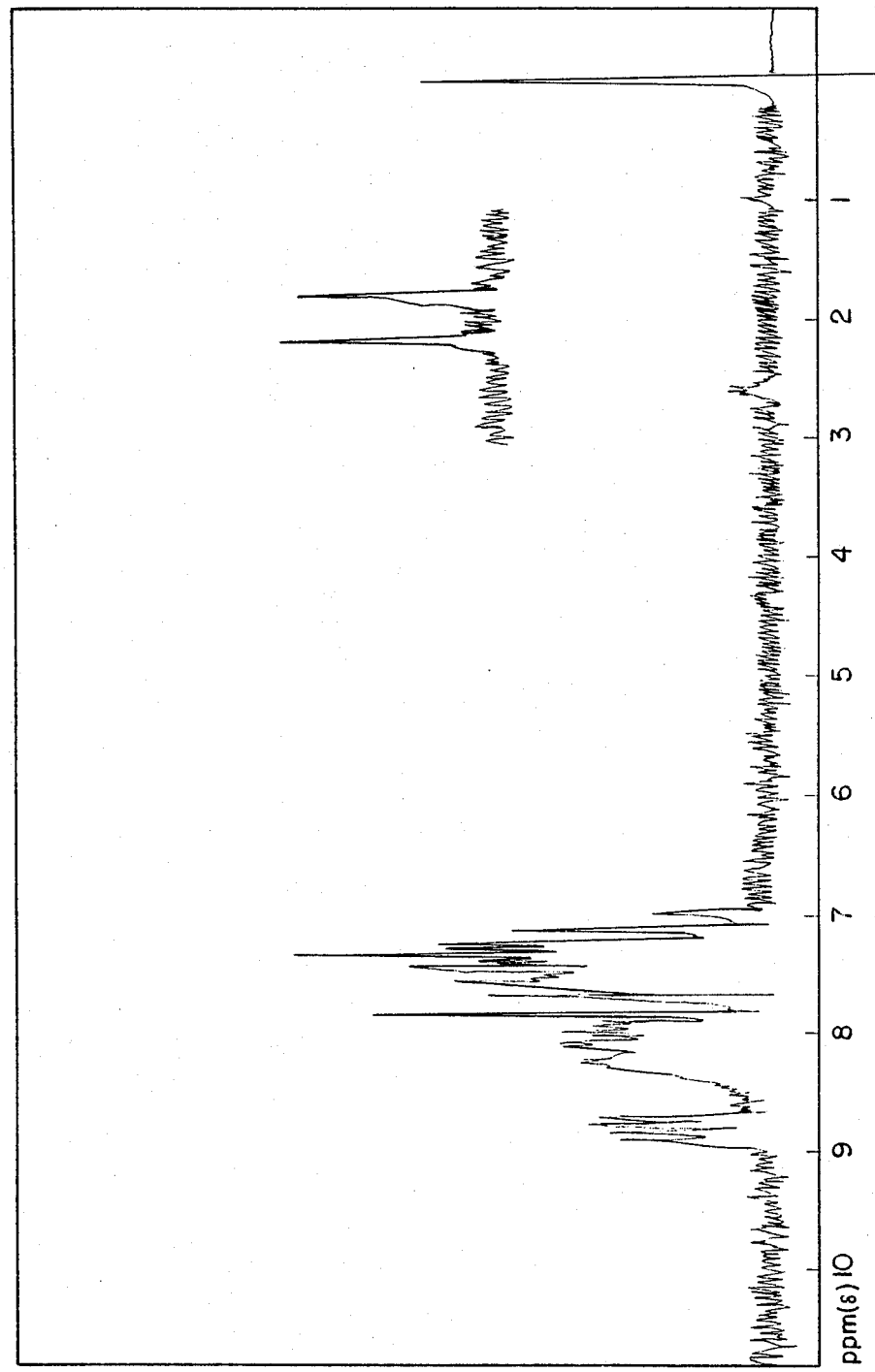

$^1$H-NMR(DMSO-d$_6$, δ): 12.00 (s, 1H, CON$\underline{H}$—), 11.7 (s, 1H, —CON$\underline{H}$—) 8.7–7.1 (m, aromatic hydrogen) (FIG. 4; solvent: CDCl$_3$:DMSO-d$_6$=3:1)

EXAMPLE 5

Preparation of Diethyl
2,2'-[(1,3-dioxo-2-phenylmethylene-1,3-propanediyl)-diimino]bisbenzoate (Compound 14) (Process b)

Diethyl 2,2'-[(1,3-dioxo-1,3-propanediyl)diimino]bisbenzoate (1.0 g, 2.51 mmol) and benzaldehyde (400 mg, 3.76 mmol) were heated under reflux in dry pyridine (8 ml) for 24 hours. After removal of pyridine, the residue was treated with water (20 ml), which was made acidic with 10% HCl under ice cooling. The resulting acidic solution was extracted with chloroform. The organic layer was washed with water, dried, concentrated to give brown oil (1.332 g), which was purified by silica gel column chromatography (firstly benzene, followed by benzene:ether=97:3). After removing the solvent from the eluent of the desired compound, the residue was crystallized by the use of n-hexane to give the title compound (384 mg, yield, 31%) in white solid. Recrystallization from the mixed solvent of $CH_3OH$—$H_2O$ gave a solid (280 mg). m.p., 139°–140° C.

Rf=0.39 [benzene:ether=95:5]

IR(KBr, cm$^{-1}$): 3250 (—CON$\underline{H}$—), 1700 (—COOEt), 1680 (—$\underline{C}$ONH—), $^1$H-NMR (DMSO-d$_6$, δ): 11.91 (s, 1H, CON$\underline{H}$), 11.38 (s, 1H, CON$\underline{H}$) 3.94–4.54 (qq, 4H, C$\underline{H_2}$CH$_3$), 1.13–1.48 (tt, 6H, —CH$_2$C$\underline{H_3}$), 6.9014 8.90 (m, aromatic hydrogen)

MS (m/e): 486 (M+)

EXAMPLE 6

Preparation of
2,2'-[[2-(3,4-dimethoxy)phenylmethylene-1,3-dioxo-1,3-propanediyl]diimino]bisbenzoic acid (Compound 20) (Process b)

2,2'-[(1,3-Dioxo-1,3-propanediyl)dimino]bisbenzoic acid (1.0 g, 2.92 mmol) and 3,4-dimethoxybenzaldehyde (0.73 g, 4.38 mmol) were heated under reflux in dry pyridine (8 ml) for 16 hours. After removal of pyridine, the mixture was treated with water, made alkaline with 10% aqueous ammonia under ice cooling, and extracted with ether. The aqueous layer was made acidic with 1N HCl under ice cooling to form solid, which was collected by filtration and washed with water. The resulting crude product was dissolved in THF, and purified by silica gel column chromatography [developing solvent: benzene:ethyl acetate =1:1 (containing 1% acetic acid)]. After removal of the eluted impurities, the effluent containing the desired compound is collected. The solvent was evaporated and the residue was treated with water to form crystals, which were collected on filter and washed with water to give a pale yellow solid of the title compound (0.614 g, yield, 43%). Recrystallization from the mixed solvent of MeOH-H$_2$O system gave a solid (0.462 g). m.p., 213°–214° C.

Rf=0.19 [ethyl acetate:benzene=1:1 (containing 1% acetic acid).

IR (KBr, cm$^{-1}$): 3500 (—CON$\underline{H}$—), 2300–3200 (—COOH), 1680 (—$\underline{C}$ONH—)

$^1$H-NMR (DMSO-d$_6$, δ): 12.0 (s, 1H, CON$\underline{H}$), 11.80 (s, 1H, CON$\underline{H}$)8.7–6.9 (m, aromatic hydrogen)

MS (m/e): 472 (M+-18)

EXAMPLE 7

Preparation of
2,2'-[[1,3-dioxo-2-(4-methyl)phenylmethylene-1,3-propanediyl]diimino]bisbenzoic acid (Compound 26)
(Process b)

2,2'-[(1,3-Dioxo-1,3-propanediyl)diimino]bisbenzoic acid (1.0 g, 2.92 mmol) and 4-methylbenzaldehyde (0.54 g, 4.38 mmol) were heated under reflux in dry pyridine (12 ml) for 16 hours. After removing pyridine, the mixture was treated with water (30 ml) and made alkaline with 10% aqueous ammonia under ice cooling. After washing with ether, the aqueous layer was made acidic with 1N HCl under ice cooling, and the precipitated solid was collected on filter and washed with water. Recrystallization of this solid from MeOH-$H_2O$ system gave the title compound (539 mg, yield, 42%) in white solid. m.p., 230°–233° C.

Rf=0.25 [ethyl acetate:benzene=1:1 (containing 1% acetic acid)]

IR (KBr, cm$^{-1}$) 3450 (CON$\underline{H}$), 3300–2200 (COOH), 1680 (CON$\underline{H}$)

$^1$H-NM$\overline{R}$(DMSO-d$_6$, δ): 12.0 (s, 1H,CON$\underline{H}$), 11.7 (s, 1H, CON$\underline{H}$), 2.3 (s, 3H, C$\underline{H}_3$), 8.7–7.0 (m, aromatic hydrogen). MS (m/e): 426 ($\overline{M}$+-18).

EXAMPLE 8

Preparation of
2,2'-[[1,3-dioxo-2-(4-nitro)phenylmethylene-1,3-propanediyl]diimino]bisbenzoic acid (Compound 36)
(Process b)

2,2'-[(1,3-dioxo-1,3-propanediyl)diimino]bisbenzoic acid (1.0 g, 2.92 mmol) and 4-nitrobenzaldehyde (0.66 g, 4.38 mmol) were heated under reflux in dry pyridine (12 ml) for 16 hours. After distilling off pyridine, the mixture was treated with water (30 ml) and with 10% aqueous ammonia under ice cooling to make alkaline, and washed with ether. The aqueous layer was made acidic with 1N.HCl, and the precipitated crystals were collected by filtration and washed with water. As the resulting solid was soluble only partly in THF, it was first subjected to separation between the soluble and the insoluble portions. As the insoluble solid gave one spot on TLC, the soluble portion was subjected to column purification [developing solvent:ethyl acetate:benzene=1:1 (containing 1% acetic acid)]. After removing the first eluting impurities, the effluent containing the desired compound was collected, and the solvent was evaporated. The residue was treated with water to give crystals, which were collected on filter, and then washed with water. The previous insoluble solid and the cystals were combined to give the title compound in white solid (884 mg, yield, 64%). The resulting product was recrystallized from the mixed solution of CH$_3$O—H—THF—H$_2$O system to give a solid (642 mg) . m.p., 275°–276° C.

Rf =0.23 [ethyl acetate:benzene =1:1 (containing 1% acetic acid)]

IR (KBr, cm$^{-1}$) 3540 (—CON$\underline{H}$—), 3300–2200 (COOH), 1680 (—CON$\underline{H}$—)

$^1$H-NMR(DMSO-d$_6$, δ): 12.1 (s, 1H, CON$\underline{H}$), 11.6 (s, 1H, CON$\underline{H}$), 8.8–7.1 (m, aromatic hydrogen). MS(m/e): 457 ($\overline{M}$+-18).

EXAMPLE 9

Preparation of
2,2'-[[1,3-dioxo-2-{2-thienyl)methylene-1,3-propanediyl]diimino]bisbenzoic acid (Compound 40)
(Process b)

2,2'-[(1,3-Dioxo-1,3-propanediyl)diimino]bisbenzoic acid (1.0 g, 2.92 mmol) and 2-thiophenealdehyde (0.49 g, 4.38 mmol) were heated under reflux in dry pyridine (8 ml) for 16 hours. After removing pyridine, the mixture was treated with water, made alkaline with 10% aqueous ammonia under ice cooling, and washed with ether. The aqueous layer was made acidic with 1N.HCl under ice cooling, and the precipitated crystals were collected on filter and washed with water. The resulting solid was purified by silica gel column chromatography and the effluent containing the desired compound was collected. After removing solvent, the residue was crystallized by treating water, collected by filtration, washed with water, and dried to give the title compound (0.730 g, yield, 57%), which was recrystallized from the mixed solvent of CH$_3$OH—H$_2$O to give the pale yellow crystals (0.602 g). m.p.: 213°–215° C.

Rf=0.35 [ethyl acetate:benzene=1:1 (containing 1% acetic acid).

IR (KBr, cm$^{-1}$): 3450 (—CON$\underline{H}$—), 3300–2300 (COOH), 1680 (—CON$\underline{H}$—)

$^1$H-NMR (DMS$\overline{O}$-d$_6$, δ): 12.0 (s, 2H, CON$\underline{H}$), 8.7–7.0 (m, aromatic hydrogen). MS (m/e): 418 (M+-18)

EXAMPLE 10

Preparation of
4-chloro-2,2'-[(1,3-dioxo-2-phenylmethylene-1,3-propanediyl)diimimo]bisbenzoic acid (Compound 46)
(Process b)

Benzaldehyde (168.7 mg, 0.162 ml, 1.59 mmol) and the compound (09) prepared in Example 3 (400 mg, 1.06 mmol) were refluxed in dry pyridine (4 ml) for 17.5 hours. Afrer removing pyridine under reduced pressure, water was added, and the mixture was made alkaline with 10% aqueous ammonia under ice cooling, which was treated with NaCl and washed with ether (30 ml×5).

The aqueous layer was made acidic with 1N.HCl (pH=2) under ice cooling, and the precipitated solid was collected on filter and washed with water. The resulting solid was dissolved in THF, and purified using silica gel column [developing solvent, ethyl acetate:benzene=1:1 (containing 1% acetic acid)]. After removing the solvent from the colorless third effluent solution, the resulting solid was sufficiently washed with water to give the title compound (226.7 mg, yield, 46%). The obtained product was recrystallized from CH$_3$OH-H$_2$O system to give a purified product. The obtained compound was found ro be a mixture of two kinds of E-form and Z-form at the rate of 1:1 from the following data.

White crystals, m.p., 153°–156° C.

Rf=0.27 and 0.23 [ethyl acetate:benzene=1:1 (containing 1% acetic acid)]

IR (KBr, cm$^{-1}$): 3700–2200 (—CO$\underline{NH}$, —COOH), 1685 (CON$\underline{H}$)

$^1$H-N$\overline{M}$R (DMSO-d$_6$, δ): 12.08 and 11.80 (CONH of E or Z form), 11.98 and 11.68 (CON$\underline{H}$ of E or Z form), 8.86–7.00 (m, aromatic hydrogen).

MS (m/e): 446 (M+-18)

EXAMPLE 11

Preparation of disodium 2,2'-[(1,3-dioxo-2-phenylmethylene-1,3-propanediyl)-diimino]bisbenzoate (Compound 49)

To methanol (2 ml), 2,2'-[(1,3-dioxo-2-phenylmethylene-1,3-propanediyl)diimino]bisbenzoic acid (500 mg) and 1N.NaOH (2.32 ml) were added, and the mixture was stirred at room temperature for 1 hour. Solvent was removed from the reaction mixture, and the residue was treated with acetone and crystallized to give the title compound (478 mg, 87%) in white solid. m.p. 283° C. (dec.)

Rf=0.26 [ethyl acetate:benzene=1:1 (containing 1% acetic acid)]

EXAMPLE 12

Preparation of 2,2'-[(1,3-dioxo-2-phenylmethyl-1,3-propanediyl)-diimino]bisbenzoic acid (Compound 50) (Process c)

(a) The compound (11) (0.5 g, 1.16 mmol) prepared in Example 4 was subjected to catalytic hydrogenation by hydrogen gas over 10% Pd/C (0.1 g), at room temperature for 24 hours. After filtering off Pd/C, and washing the catalyst with THF, the solvent was evaporated to give the title compound in pale brown crystals. The product was recrystallized from the mixed solvent of $CH_3OH$—$H_2O$ system (amount, 0.384 g, yield, 76%). m.p., 234-236° C.

Rf=0.12 [ethyl acetate:benzene=1:1 (containing 1% acetic acid)

IR(Kbr, $cm^{-1}$): : 3300-2300 (—CO$\underline{NH}$, COOH), 1680 (—$\underline{C}$ONH—)

$^1$H-N$\overline{MR}$(DMSO-$d_6$, δ): 11.6 (s, 2H, —CON$\underline{H}$—), 8.5-7.0 (m, aromatic hydrogen), 3.9 (t, 1H, —C$\underline{H}$<) 3.3 (d, 2H, —C$\underline{H}$2—)

MS (m/e): 414 (M+-18)

(b) Compound (11)(500 mg, 1.16 m mol) and $NiCl_2.6H_2O$ (551 mg, 2.32 m mole) were dissolved in methanol (25 ml). On adding $NaBH_4$ (438.8 mg, 11.6 m mole) in small portions to the solution while attention being paid to the generation of hydrogen gas under ice cooling, the reaction mixture turned black. After addition of $NaBH_4$ (about 1 hour), the solution was further stirred at room temperature for 30 minutes. The black solid was collected on filter, and sufficiently washed with methanol. The filtrate was combined from which the solvent was removed under reduced pressure. The residue was treated with water, made acidic (pH 2) with 10% HCl, and the precipitated solid was collected on filter, washed with water, and dried to give white solid. This solid was dissolved in THF and purified by silica gel column chromatography [developing solvent: ethyl acetate : benzene=1:1 (containing 1% acetic acid)]. After the purification, the resulting solid was sufficiently washed with water and dried to give the title compound (280 mg, yield, 56%) as a white solid.

The compound obtained here showed full agreements in TLC and spectral data with the reduced product obtained in (a) above.

EXAMPLE 13

Preparation of 2,2'-[(1,3-dioxo-2-phenylmethylene--1,3-propanediyl)diimino]bisbenzoic acid (Compound 11) (Process a)

The compound (14) (100 mg, 0.205 mmol) and 1N.NaOH (0.61 ml, 0.61 mmol) were refluxed in methanol (0.61 ml) for 45 minutes. After removing the solvent under reduced pressure, the mixture was treated with 10% hydrochloric acid under ice cooling to make acidic (pH 2) to precipitate solid, which was collected on filter. The resulting product was washed with water and dried to give a white solid (81.5 mg), which was dissolved in THF and purified by silica gel column chromatography [developing solvent: ethyl acetate: benzene, 1:1 (containing 1% acetic acid)]. After removal of the solvent from the first eluent, the obtained solid was sufficiently washed with water to give the title compound (37.1 mg, yield, 42%).

The obtained product showed full agreement in its TLC, melting point, and spectral data with the compound obtained in Example 4.

EXAMPLE 14

Preparation of diethyl 2,2'-[(1,3-dioxo-2-phenylmethylene-1,3-propanediyl)-diimino]bisbenzoate (Compound 14) (Process e)

The compound (11) prepared in Example 4 (430 mg, 1 mmol) was dissolved in dry acetone (10 ml) and dry DMF (1 ml). To the solution $K_2CO_3$ (276 mg, 2 mmol) was added, to which $C_2H_5I$ (0.191 ml, 374 mg, 2.4 mmol) was added dropwise. After addition of DMF (6 ml), the mixture was stirred at 60° C. for 2 hours. The reaction solution was poured into ice water (70 ml) and extracted three times with ethyl acetate. The extract was washed with water and dried. The solvent was evaporated under reduced pressure to give the title compound (480 mg, yield, 98%) as pale yellow solid. m.p., 139°–141° C.

The resulting product fully agreed with the compound (14) prepared in Example 5 in IR and NMR spectra.

EXAMPLE 15

Preparation of 2,2'-[(1,3-dioxo-2-phenylmethyl-1,3-propanediyl)-diimino]bisbenzoic acid (Compound 50) (Process d)

Diethylbenzyl malonate (2.0 g, 1.85 ml, 7.99 mmol) and anthranilic acid (2.19 g, 15.98 mmol) were refluxed in dry xylene (44 ml) for 22.5 hours. After removing the solvent from the reaction solution under reduced pressure, the residue was dissolved in THF, and the solution was subjected to column purification [developing solvent, ethyl acetate:benzene=1:1 (containing 1% acetic acid)]. The initially flowing out several kinds of impurities were discarded the title compound was eluted as a colorless solution. After removal of the solvent, the resulting solid was sufficiently washed with water to give the title compound (250 mg, yield, 7%), which was recrystallized from the mixed solvent of $CH_3OH$—$H_2O$ system. Yield, 190 mg.

Rf=0.12 [ethyl acetate:benzene=1:1 (containing 1% acetic acid)]

The product obtained showed full agreement with that prepared by hydrogenation in Example 12 in IR and NMR spectra.

EXAMPLE 16

Preparation of dimethyl 2,2'-[[2-(3,4-dimethoxy)phenylmethylene-1,3-dioxo-1,3-propanediyl]diimino]bisbenzoate (Compound 47) (Process f)

The compound (24) 0.5 g, 1.05 nmol) was dissolved in dry acetone (13 ml), $K_2CO_3$ (0.435 g, 3.15 mmol) and methyl iodide (0.52 g, 0.229 ml, 3.68 mmol) were added in this order. The mixture was heated to 60° C., and the precipitated potassium salt was dissolved by adding dry DMF (5 ml) thereto to form a yellow-brown solution. The resultant was further stirred at 60° C. for 30 minutes, whereupon the reaction solution changed to green color. The reaction mixture was poured into water, made weak acidic with 1N.HCl, and extracted three times with ethyl acetate. The organic layer was washed with water, then with saturated brine, dried, and evaporated. The residual yellow oil was crystallized from isopropyl ether to give the title compound (0.458 g, yield, 84%) as pale yellow crystals, which was recrystallized from the mixed solvent of THF—CH$_3$OH—H$_2$O system. Yield, 0.391 g. m.p., 157°-158° C.

Rf=0.44 (ethyl acetate:benzene=4:1)

IR (KBr, cm$^{-1}$), 3250 (CON$\underline{H}$), 1700 ($\underline{C}$OOCH3), 1680 (CON$\underline{H}$)

$^1$H-$\overline{\text{NMR}}$ (DMSO-d$_6$, δ): 11.4 (s, 1H, CON$\underline{H}$), 11.1 (s, 1H, CON$\underline{H}$), 8.7-7.0 (m, aromatic hydrogen), 3.85 (s, 3H, COO$\overline{C}H_3$), 3.80 (s, 3H, 4—$\overline{C}H_3$O—), 3.65 (s, 3H, COO$\underline{C}H_3$), 3.55 (s, 3H, 3—$\underline{C}H_3$O—)

MS (m/e): 587 (M+)

EXAMPLE 17

Preparation of dimethyl 2,2'-[[1,3-dioxo-2-(1-methyl-1H-pyrol-2-yl)methylene-1,3-propanediyl]diimino]bisbenzoate (Compound 48) (Process g)

Into a mixture of NaH (57.1 mg, 1.43 mmol) and dry DMF (0.5 ml), a solution of the compound (42) (200 mg, 0.48 mmol) in dry DMF (1.5 ml) was added dropwise, and the mixture was stirred at room temperature for 10 minutes, after which the mixture was treated with methyl iodide (222.9 mg, 0.097 ml, 1.57 mmol) and stirred at room temperature for 5.5 hours. The reaction mixture was poured into ice water (50 ml), and extracted with ethyl acetate. The organic layer was washed with water and dried. The solvent was evaporated under reduced pressure to give yellow oil (359.8 mg). The obtained oil was purified by column chromatography [developing solvent, ethyl acetate: benzene=1:1 (containing 1% acetic acid)]. Solvent was removed irom the first effluent yellow solution, and the obtained yellow oil was crystallized with isopropyl ether to give the title ccmpound (50 mg, yield, 23%) as a yellow solid, which was recrystallized from the mixed solvent of CH$_3$OH—H$_2$O system. m.p., 157-158° C.

Rf=0.66 [ethyl acetate:benzene=1:1 (containing 1% acetic acid)]

IR (KBr, cm$^{-1}$): 3270. (CON$\underline{H}$, 1698 (—$\underline{C}$OOCH$_3$), 1670 (—O/ NH—)

$^1$H-NMR (DMSO-d$_6$, δ):11.30 (s, 1H, CON$\underline{H}$), 11.23 (s, 1H, CON$\underline{H}$), 8.80-6.00 (m, aromatic hydrogen), 3.78 (s, 3H, N—$\overline{C}$Hhd 3), 3.70 (s, 3H, —COO$\underline{C}H_3$) MS (m/e): 461 (M+)

The obtained product showed full agreement in TLC IR, and NMR with the product prepared by esterifying the compound (43) according to Example 16 by the use of CH$_3$I—K$_2$CO$_3$ system.

In a similar manner to the above Examples, there were obtained the compounds shown in the following Table. In the Table, the positions of the bonds attached to the groups R$^2$, R$^{2'}$, R$^3$, and R$^{3'}$, are shown, for convenience, by the position numbers based on the bonding position of —CON$\underline{H}$taken as 1, as in the illustration. (Accordingly, the position numbers in the table differ frequently from the numbers in the usual nomenclature.) Further, the processes for producing the compounds are shown by the Numbers of Examples in which the compounds were actually produced or in which similar reaction systems were used.

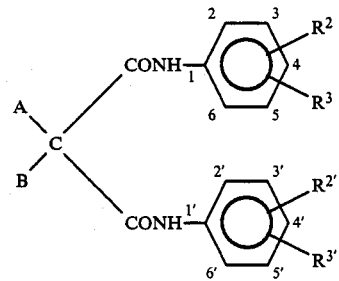

| Compound | Example | A, B | R$^2$, R$^{2'}$ | R$^3$, R$^{3'}$ | mp (°C.) | $^1$H—NMR(δ, DMSO—d$_6$) |
|---|---|---|---|---|---|---|
| 01 | 1 | H, H | H | 2,2'-COOH | 254-258 | 11.25(s, 2H, —CON$\underline{H}$—), 3.70(s. 2H, $\underline{C}H_2$—) |
| 02 | 1 | H, H | H | 3,3'-COOH | 290-297 | 10.26(s, 2H, —CON$\underline{H}$—), 3.53(s. 2H, $\underline{C}H_2$—) |
| 03 | 1 | H, H | H | 4,4'-COOH | >300 | 10.44(s, 2H, —CON$\underline{H}$—), 3.60(s. 2H, $\underline{C}H_2$—) |
| 04 | 1 | H, H | H | 2,2'-COOEt | 137-140 | 11.60(s, 2H, —CON$\underline{H}$—), 3.63(s. 2H, $\underline{C}H_2$—) |
| 05 | 1 | H, H | 5,5'-Cl | 2,2'-COOH | 292-293.5 | 11.50(s, 2H, —CON$\underline{H}$—), 3.70(s. 2H, $\underline{C}H_2$—) |

-continued

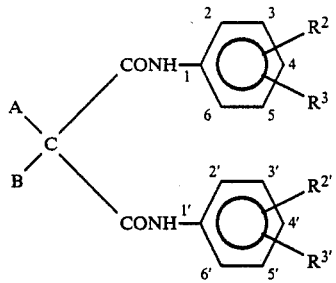

| | | | | | | | |
|---|---|---|---|---|---|---|---|
| 06 | 2 | H, H | 5,5'-NO$_2$ | 2,2'-COOH | 269–270.5 | 11.50(s, 2H, —CON$\underline{H}$—), 3.80(s. 2H, C$\underline{H_2}$—) | |
| 07 | 1 | H, H | 4,4'-CH$_3$ | 2,2'-COOH | 257–258 | 11.40(s, 2H, —CON$\underline{H}$—), 3.56(s. 2H, C$\underline{H_2}$—) | |
| 08 | 2 | H, H | 2,2'-OCH$_3$ | 5,5'-COOH | 283–287 | 9.66(s, 2H, —CON$\underline{H}$—), 3.73(s. 2H, C$\underline{H_2}$—) | |
| 09 | 3 | H, H | H, 5'-Cl | 2,2'-COOH | 259–261 | 11.56(s, 2H, —CON$\underline{H}$—), 3.66(s. 2H, C$\underline{H_2}$—) | |

| Compound | Example | A, B | R$^1$ | R$^2$, R$^{2'}$ | R$^3$, R$^{3'}$ | mp (°C.) | Yield (%) |
|---|---|---|---|---|---|---|---|
| 11 | 1, 4, 13 (*1) | | C$_6$H$_5$— | H | 2,2'-COOH | 195–196 | 51 |
| 12 | 1, 4 | R$^1$\C= | C$_6$H$_5$— | H | 3,3'-COOH | 293–294 | 30 |
| 13 | 1, 4 | | C$_6$H$_5$— | H | 4,4'-COOH | 278–280 | 30 |
| 14 | 1, 5, 14 | | C$_6$H$_5$— | H | 2,2'-CO$_2$C$_2$H$_5$ | 139–140 | 31 |
| 15 | 1, 4 | H/ | C$_6$H$_5$— | 5,5'-Cl | 2,2'-COOH | 245–246.5 | 40 |
| 16 | 2, 4 | | C$_6$H$_5$— | 5,5'-NO$_2$ | 2,2'-COOH | 272–273 | 53 |
| 17 | 1, 4 | | C$_6$H$_5$— | 4,4'-CH$_3$ | 2,2'-COOH | 240–242 | 34 |
| 18 | 2, 4 | | C$_6$H$_5$— | 2,2'-OCH$_3$ | 5,5'-COOH | 290–291 | 12 |
| 19 | 1, 4 | | 4-CH$_3$O—C$_6$H$_4$— | H | 2,2'-COOH | 216–219 | 47 |
| 20 | 1, 6 (*2) | | 3,4-(CH$_3$O)$_2$—C$_6$H$_3$— | H | 2,2'-COOH | 213–214 | 43 |
| 21 | 1, 6 | | 3,4-(CH$_3$O)$_2$—C$_6$H$_3$— | 5,5'-Cl | 2,2'-COOH | 282–286 | 52 |
| 22 | 2, 6 | | 3,4-(CH$_3$O)$_2$—C$_6$H$_3$— | 5,5'-NO$_2$ | 2,2'-COOH | 271–273 | 58 |
| 23 | 1, 6 | | 3,4,5-(CH$_3$O)$_3$—C$_6$H$_2$— | H | 2,2'-COOH | 194–196 | 48 |
| 24 | 1, 6 | | 3-CH$_3$O—4-HO—C$_6$H$_3$— | H | 2,2'-COOH | 187–189 | 30 |
| 25 | 1, 6 | | 3,4-(OCH$_2$O)—C$_6$H$_3$— | H | 2,2'-COOH | 209–210 | 42 |
| 26 | 1, 7 | | 4-H$_3$C—C$_6$H$_4$— | H | 2,2'-COOH | 230–233 | 42 |
| 27 | 1, 4 | | 4-(CH$_3$)$_2$CH—C$_6$H$_4$— | H | 2,2'-COOH | 218–221 | 44 |
| 28 | 1, 4 | | 4-(CH$_3$)$_2$N—C$_6$H$_4$— | H | 2,2'-COOH | 223–225 | 61 |
| 29 | 1, 7 | | 4-CH$_3$CONH—C$_6$H$_4$— | H | 2,2'-COOH | 288–289 | 38 |
| 30 | 1, 4 | | 4-Cl—C$_6$H$_4$— | H | 2,2'-COOH | 261–262 | 44 |
| 31 | 1, 4 | | 3-Cl—C$_6$H$_4$— | H | 2,2'-COOH | 229–230 | 73 |
| 32 | 1, 4 | | 2-Cl—C$_6$H$_4$— | H | 2,2'-COOH | 228–230 | 40 |
| 33 | 1, 4 | | 4-Br—C$_6$H$_4$— | H | 2,2'-COOH | 262–264 | 57 |
| 34 | 1, 6 | | 4-F—C$_6$H$_4$— | H | 2,2'-COOH | 238–240 | 41 |
| 35 | 1, 4 | | 4-F$_3$C—C$_6$H$_4$— | H | 2,2'-COOH | 235–237 | 46 |
| 36 | 1, 8 | | 4-O$_2$N—C$_6$H$_4$— | H | 2,2'-COOH | 275–276 | 64 |
| 37 | 1, 4 | | 4-NC—C$_6$H$_4$— | H | 2,2'-COOH | 280–282 | 47 |
| 38 | 1, 4 | | 1-naphthyl | H | 2,2'-COOH | 237–239 | 34 |
| 39 | 1, 4 | | 2-furyl | H | 2,2'-COOH | 214.5–216.5 | 41 |
| 40 | 1, 9 | | 2-thienyl | H | 2,2'-COOH | 213–215 | 57 |
| 41 | 1, 4 | | 3-thienyl | H | 2,2'-COOH | 210–212 | 46.5 |
| 42 | 1, 4 | | 2-pyrrolyl | H | 2,2'-COOH | 247–250 (dec) | 56 |
| 43 | 1, 4 (*3) | | 1-methyl-2-pyrrolyl | H | 2,2'-COOH | 205–207 (dec) | 61 |
| 44 | 1, 4 | | 3-pyridyl | H | 2,2'-COOH | 259–261 | 39 |
| 45 | 1, 4 (*3) | | 1-methyl-3-indolyl | H | 2,2'-COOH | 233–234 | 41 |
| 46 | 3, 10 | | C$_6$H$_5$— | H, 5-Cl | 2,2'-COOH | 153–156 | 46 |
| 47 | 1, 6, 16 | | 3,4-(CH$_3$O)$_2$—C$_6$H$_3$ | H | 2,2'-COOCH$_3$ | 157–158 | 84 |
| 48 | 1, 4, 17 | | 1-methyl-2-pyrrolyl | H | 2,2'-COOCH$_3$ | 157–158 | 23 |
| 49 | 1, 4, 11 | | C$_6$H$_5$— | H | 2,2'-COONa | 283 | 87 |
| 50 | 1, 4, 12, 15 | R$_1$\H—C—/H | C$_6$H$_5$— | H | 2,2'-COOH | 234–236 | 76 |

Note:
01–03 are known compounds.
*1: This compound can be also obtained by hydrolysis of Compound 14 (Process a).
*2: This compound can be obtained by methylation of Compound 24 (Process f) and hydrolysis of ester.
*3: This compound can be obtained by methylation of corresponding NH—compound (Process g) and hydrolysis of ester.

EXAMPLE 18

Preparation of corresponding dimethyl ester (Compound 51) from 2,2'-[(1,3-dioxo-2-phenylmethylene-1,3-propanediyl)diimino]bisbenzoic acid (Compound 11)

To the solution of the Compound (11) [obtained from benzaldehyde and 2,2'-[(1,3-dioxo-1,3-propanediyl)-diimino]bisbenzoic acid in a yield of 72%](3.0 g, 6.97 mmol) were added anhydrous potassium carbonate (1.92 g, 13.9 mmol) and then dry dimethylformamide (DMF) (9 ml). When the resulting solution was treated with methyl iodide (2.37 g=1.04 ml, 16.7 mmol), a white solid precipitated, which was dissolved by further addition of dry DMF (20 ml). After stirring at 60° C. for 50 minutes, the reaction solution was poured into ice water (300,ml), and the solution was extracted three times with ethyl acetate. The organic layer was washed with water and dried over $Na_2SO_4$. The solvent was evaporated and the yellow viscous residue was crystallized from isopropyl ether to give pale yellow solid of the desired compound. (2.9 g, yield, 91%). m.p., 110°–111° C.

Rf=0.62 (benzene:ether=9:1, silica gel)

IR (KBr, $cm^{-1}$): 3300, 1700, 1605

$^1$H-NMR($CDCl_3$, δ): 11.9 (S, 1H, -CON$\underline{H}$—), 11.3 (S, 1H, —CON/ —), 6.9–9.0 (m, 14H, aromatic hydrogen, vinyl hydrogen), 3.9 (S, 3H, —COOC$\underline{H}_3$), 3.6 (S, 3H, —COOC$\underline{H}_3$)

EXAMPLE 19

Preparation of Compound 51 from 2,2'-phenylethenilidenebis(3,1-benzoxazine-4-one) [Compound 52]

(a) Preparation of Compound 52:

Compound 11 (2.0 g, 4.65 mmol) was suspended in dry benzene (200 ml) and trifluoroacetic anhydride (2.59 ml, 18.60 mmol) was added. The resulting suspension, when stirred at room temperature, became pale yellow-brown solution in about 10 minutes. After one hour, the solvent was distilled off, and the residue was extracted with ethyl acetate. The organic layer was washed succesively with 1N.HCl, water, 4% $NaHCO_3$, and water and dried over magnesium sulfate. The solvent was evaporated and the residue was crystallized by adding isopropylether to give the compound 52 (1.67 g, yield, 91%) in white solid. m.p., 214°–215° C.

IR (KBr, $cm^{-1}$) 1760 (C=0)

$^1$H-NMR ($CDCl_3$, δ):8.33–7.20 (m, aromatic hydrogen, vinyl hydrogen)

Alternatively, the use of oxalyl chloride - DMF, DCC - DMAP or 2-chloro-N-methylpyridinium iodide —$N(C_2H_5)_3$ in place of trifluoroacetic anhydride in this reaction also gave the compound 52.

(b) Preparation of Compound 51:

To the solution of dry $CH_3OH$ (0.15 ml, 3.81 mmol) in dry benzene (15 ml), n-butyl lithium (1.678M n-hexane solution) (1.66 ml, 2.79 mmol) was slowly added dropwise under ice cooling. After the addition, the solution was stirred at room temperature for 15 minutes. To the resulting solution of $LiOCH_3$, the compound 52 (500 mg, 1.27 mmol) obtained as above was added, and the mixture was heated under reflux for 30 minutes. After the reaction, the solvent was removed, and the residue was dissolved in chloroform, which was acidified (pH 2) by adding 1N.HCl under ice cooling. The organic layer was separated, washed with 1N.HCl and saturated brine and dried over magnesium sulfate. The solvent was evaporated. The viscous residue was dissolved in chloroform, and purified by silica gel column chromatography (developing solvent: benzene:ether=9:1). The third eluent was collected, from which the solvent was removed, and the residue was crystallized from isopropyl ether to give the desired pale yellow solid (411 mg, yield, 70%). m.p., 110°–111° C.

The IR and NMR spectra of the solid fully agreed with those of the product in Example 18.

The use of $NaOCH_3$ (28% methanol solution) in place of $LiOCH_3$ in this reaction also gave the desired compound.

EXAMPLE 20

Preparation of Compound 51 from dimethyl 2,2'-[(1,3-dioxo-1,3-propanediyl)diimino]bisbenzoate Benzaldehyde (430 mg, 4.05 mmol) and dimethyl 2,2'-[(1,3-dioxo-1,3-propanediyl)diimino]bisbenzoate (1.0 g, 2.70 mmol) were heated under reflux in dry pyridine (8 ml) for 24 hours. After the reaction, pyridine was removed under reduced pressure from the reaction mixture, and the residue was treated with water (20 ml) to make it acidic with 10% HCl under ice cooling. The resulting solution was extracted with chloroform, organic layer was separated, washed with water and dried over magnesium sulfate. The solvent was evaporated under reduced pressure to give a yellow-brown oil. The oil was dissolved in the developing solvent and purified by silica gel column chromatography (developing solvent, benzene:ether=97:3) to give an oil, which was crystallized from n-hexane to give the desired compound of white solid (657 mg, yield, 53%). m.p., 110°–111° C.

IR and $^1$H-NMR spectra of the product fully agreed with those of the dimethyl ester obtained in Example 18.

EXAMPLE 21

Preparation of diisopropyl 2,2'-[(1,3-dioxo-2-phenylmethylene-1,3-propanediyl)-diimino]bisbenzoate(Compound 53)

(a) The compound 11 (1.0 g, 2.3 mmol) was dissolved in dry acetone (25 ml) and dry DMF (5 ml) and $K_2CO_3$ (639 mg, 4.6 mmol) and then isopropyl icdide (980 mg, 5.8 mmol) were added. By adding dry DMF (15 ml), the precipitated solid was dissolved, and the mixture was stirred at 60° C. for 5 hours. After completion of the reaction, the reaction solution was poured into ice water (500 ml) and extracted with ethyl acetate. After drying over magnesium sulfate and solvent-removal, the residue was dissolved in chloroform and purfied by silica gel column chromatography [developing solvent: benzene:ether=9:1]to give the desired compound as pale yellow solid. Recrystallization from the mixed solution of methanol-water yielded a white crystal (788 mg, yield, 67%). m.p., 132°–134° C.

IR (KBr, $cm^{-1}$): 3250, 3200, 1680

$^1$H-NMR ($CDCl_3$, δ):12.00 (S, 1H, —CON$\underline{H}$—), 11.47 (S, 1H, —CON$\underline{H}$—), 8.95–6.95 (m, —CH=C—, aromatic hydrogen), 5.18 septet×2, 2H, —C$\underline{H}$($CH_3$)$_2$×2), 1.33 (d, 6H, —CH(C$\underline{H}$3)2), 1.23 (d, 6H, —CH(C$\underline{H}_3$)$_2$)

(b) The compound 11 (4.0 g, 9.3 mmol) was mmol) was dropwise added under ice cooling. To the mixture, 8 drops of dry DMF was further added, and the mixture was stirred at room temperature for 2 hours. After completion of the reaction, the solvent was removed, and the residue was extracted with chloroform. The extract was washed with 1N.HCl, saturated aqueous NaCl solution, 4% NaHCO$_3$ aqueous solution, and saturated aqueous NaCl solution and dried over MgSO$_4$. The solvent was evaporated to give a pale yellow solid. The resultant product was dissolved in a mixed solution of benzene:ethyl acetate=1:1 and applied on a silica gel column for chromatography (developing solvent, benzene:ethyl acetate - 1:1). After removing the solvent from the eluent containing 2,2'-phenylethenilidene-bis(3,1-benzoxazine-4-one) [Compound 52], the residue was crystallized from isopropyl ether to give the Compound 52 in white solid (3.0 g, yield, 82%), which was recrystallized from the mixed solvent of benzene and n-hexane to give white crystal (2.5 g, yield, 68%). m.p., 214°-215° C.

IR (KBr, cm$^{-1}$), 3450, 1760, 1655

$^1$H-NMR (CDCl$_3$, δ); 8.33-7.20 (aromatic hydrogen)

Then, to a solution of dry isopropanol (0.29 ml, 3.80 mmol) in dry benzene (10 ml), n-butyl lithium (1.678 M, n-hexane solution) (2.12 ml 3.6 mmol) was gradually added dropwise under ice cooling. After stirring the reaction mixture at room temperature for 10 minutes, the solvent was removed to give LiOCH(CH$_3$)$_2$ in white solid, which was dissolved in dry benzene (15 ml). The above compound 52 (500 mg, 1.3 mmol) was added to the above solution and the mixture was refluxed for 30 minutes. After completion of the reaction, the solvent was removed, and the residue was dissolved in water and made weak acidic with 1N.HCl under ice cooling. After stirring the mixture for a while under ice cooling, the precipitated solid was collected on filter, washed with water, and dried. The solid was dissolved in chloroform and applied on a column for chromatography (developing solvent: benzene:ethyl acetate=4:1) to give the desired compound in white solid.

Recrystallization of the product from a mixed solvent of methanol and water gave white crystals (310 mg, yield, 47%).

The m.p., IR, and NMR spectra of the product fully agreed with those obtained in (a) above.

EXAMPLE 22

Preparation of di-tertiary butyl 2,2'-[(1,3-dioxo-2-phenylmethylene-1,3-propanediyl)-diimino]bisbenzoate (Compound 54)

The compound 52 (1.0 g, 2.5 mmol) obtained in the same manner as in Example 21 (b) was dissolved in dry benzene (80 ml), treated with KOC(CH$_3$)$_3$ (684 mg, 6.1 mmol), and heated under reflux for 1 hour. After completion of the reaction, the solvent was evaporated and the residue was dried and suspended by adding a small amount of water under ice cooling. The aqueous layer was made neutral with 0.5N.HCl, and the residue was dissolved by adding chloroform. The mixed layer was removed to a separating funnel. After the solid was completely dissolved, water was added to wash the solution so as to make the chloroform layer neutral or weak acidic. The chloroform layer was separated, washed with saturated aqueous NaCl solution and dried over magnesium sulfate. The solvent was evaporated to give a white solid. The product was dissolved in chloroform and purified by silica gel column chromatography (developing solvent: benzene:ethyl acetate=4:1) to give the desired compound as white solid (801 mg, crude yield 58%). Recrystallization from the mixed solvent of methanol and water gave white crystals (654 mg, yield, 47%). m.p., 117°-118° C.

IR (KBr, cm$^{-1}$): 3250, 1680

$^1$H-NMR (CDCl$_3$, δ): 12.03 (S 1H —CON$\underline{H}$—) 11.57 (S 1H —CON$\underline{H}$—), 9.0-7.0 (m, —C$\underline{H}$=C— aromatic hydrogen), 1.4$\overline{8}$ (S, 9H, —OC(C$\underline{H}_3$)$_3$), 1.38 (S, 9H, —OC(C$\underline{H}_3$)$_3$)

EXAMPLE 23

Preparation of di[2-(3-phthalidylidene)ethyl]-2,2'-[(1,3-dioxo-2-phenylmethylene-1,3-propanediyl)diimino]bisbenzoate (Compound 55)

The compound 11 (1.0 g, 2.3 mmol) and dry N(C$_2$H$_5$)$_3$ (0.64 ml, 4.6 mmol) were stirred in dry acetone (15 ml) at room temperature for 30 minutes. To the mixture, (Z)-3-(2-bromoethylidene)phthalide (1.1 g, 4.6 mmol) dissolved in dry acetone (10 ml) was added dropwise. After the addition, the mixture was stirred at room temperature for 72 hours. After the reaction, the precipitate was removed, and acetone was removed from the filtrate. The residue was extracted by chloroform, washed with aqueous solution of 4% NaHCO$_3$ (twice) and saturated NaCl aqueous solution (twice) and dried over magnesium sulfate. The solvent was evaporated to give a colorless viscous product. The obtained product was dissolved in the developing solvent and applied on a column for chromatography (developing solvent: benzene:ethyl acetate=4:1) to separate the desired product. Removal of solvent from the eluent gave a viscous substance, but cooling it with dry ice and acetone gave a white solid. Recrystallization from the mixed solvent of methanol and acetone gave white crystals (1.21 g, yield, 70%). m.p., 143°-146° C.

IR (KBr, cm$^{-1}$): 3250, 1790, 1685

$^1$H-NMR (CDCl$_3$, δ) ): 11.83 (S, 1H, —CON$\underline{H}$—), 11.30 (S, 1H, —CON$\underline{H}$—), 8.90-6.92 (m, C$\underline{H}$=C—, aromatic hydrogen), 5.83 (tt, 2H, —CH$_2$C$\underline{H}$=phthalidylidene×2), 5.20 (d, 2H, —C$\underline{H}_2$CH=phthalidylidene), 4.93 (d, 2H, —C$\underline{H}$2CH=phthalidylidene)

EXAMPLE 24

Preparation of di(3-phthalidyl)-2,2'-(1,3-dioxo-2-phenylmethylene-1,3-propanediyl)-diimino]bisbenzoate (Compound 56)

The compound 11 (2.0 g, 4.7 mmol) and dry triethylamine (845 mg, 8.4 mmol) were stirred in acetone (23 ml) at room temperature for 30 minutes. To the mixture 3-bromophthalide (1.79 g, 8.4 mmol) dissolved in dry acetone (6 ml) was added, and the mixture was stirred at room temperature for 17 hours. After completion of the reaction, the precipitate was removed, and the solvent was removed from the filtrate. The residue was extracted with chloroform, washed with saturated NaHCO$_3$ aqueous solution and saturated brine and dried over anhydrous magnesium sulfate. The solvent was evaporated to give a colorless viscous product. The product was dissolved in the developing solvent and applied on a silica gel column for chromatography (developing solvent: benzene:ether=9:1) to give the desired product of viscous substance.

Crystallization with isopropylether gave white solid (1.98 g, yield, 61%). As this substance shows a slight tendency of decomposition in the stage of separation and purification to produce impurities, it is difficult to obtain pure product. m.p., 131°-134° C. (methanol - THF).

IR (KBr, cm$^{-1}$): 3290, 1790, 1710, 1690

$^1$H-NMR (CDCl$_3$, δ) 11.73 (S, 1H, —CONH—), 11.13 (S 1H, —CONH—), 9.00-6.87 (m, CH=C—, aromatic hydrogen, phthalidyl)

EXAMPLE 25

Preparation of di(pivaloyloxymethyl)- 2,2'-[(1,3-dioxo-2-phenylmethylene-1,3-propanediyl)diimino]bisbenzoate (Compound 57)

The compound 11 (1.0 g, 2.3 mmol) and dry N(C$_2$H$_5$)$_3$ (470 mg, 4.6 mmol) were stirred in dry acetone (17 ml) at room temperature for 30 minutes. To the mixture chloromethyl pivalate (721 mg, 4.6 mmol) and NaI (696 mg, 4.6 mmol) were added, and the mixture was heated under reflux for 6 hours.

After the reaction, the precipitate was removed, and the filtrate was evaporated. The residue was extracted with chloroform, washed with saturated aqueous NaHCO$_3$ solution and saturated aqueous NaCl solution, dried over anhydrous Na$_2$SO$_4$ and the solvent was removed to give a viscous solid. The resulting product was dissolved in benzene and purified by silica gel column chromatography (developing solvent: isopropyl ether) to give the desired compound as white solid (1.23 g, 80%).

Recrystallization from the solution of mixture of benzene and n-hexane gave white crystals (1.04 g, 68%). m.p., 103°-104° C.

IR (KBr, cm$^{-1}$): 3275, 1750, 1705, 1685

$^1$H-NMR (CDCl$_3$, δ) 11.73 (S, 1H, —CONH—), 11.10 (S, 1H, —CONH—), 8.97-6.92 (m, CH=C, aromatic hydrogen), 5.95 (S, 2H, —OCH$_2$OCO—), 5.68 (S, 2H, —OCH$_2$OCO—), 1.19 (S, 9H, —C(CH3)3), 1.15 (S, 9H, —C(CH3)3)

EXAMPLE 26

Preparation of di[1-(ethoxycarbonyloxy)ethyl]-2,2'-[(1,3-dioxo-2-phenylmethylene-1,3-propanediyl)diimino]bisbenzoate (Compound 58)

The compound 11 (2.0 g, 4.7 mmol) and dry N(C$_2$H$_5$)$_3$ (1.13 g, 11.2 mmol) were stirred in dry acetone (60 ml) at room temperature for 30 minutes. The mixture was treated with ethyl 1-chloroethyl carbonate (1.70 g, 11.2 mmol) and NaI (1.67 g, 11.2 mmol) and heated under reflux for 23 hours. After completion of the reaction, the precipitate was removed, and the solvent was removed from the filtrate. The residue was extracted with benzene, washed with saturated aqueous solution of NaHCO$_3$ and saturated solution of NaCl and dried over anhydrous Na$_2$SO$_4$. The solvent was evaporated to give a colorless viscous product. The resultant product was dissolved in developing solvent and purified by silica gel column chromatography (developing solvent: benzene:ether=95:5) to give the desired compound as white solid (1.34 g, crude yield, 44%). The solid was dissolved in methanol at room temperature, treated with water, and cooled with a solution of dry ice in acetone. The precipitated solid was filtered by suction, followed immediately by drying under reduced pressure to give the desired compound as white crystal (970 mg, yield, 32%). m.p., 48°-51° C.

IR (KBr, cm$^{-1}$): 3350, 1760, 1685

$^1$H-NMR (CDCl$_3$, δ): 11.73 (S, 1H, —CONH—), 11.13 (S, 1H —CONH—), 8.90-6.46 (m, aromatic hydrogen, CH=C, —OCH(CH$_3$)O, 4.36-3.93 (q, 4H, —CH$_2$CH$_3$×2), 1.70-1.10 (m, 12H, —CH(CH3)×2, —CH$_2$CH$_3$×2)

EXAMPLE 27

Preparation of di[(5-methyl-2-oxo-1,3-dioxole-4-yl)methyl]-2,2'-[(1,3-dioxo-2-phenylmethylene-1,3-propanediyl)diimino]bisbenzoate (Compound 59)

(Preparation of starting compound)

4,5-Dimethyl-1,3-dioxole-2-one (2.0 g, 17.5 mmol), N-bromosuccinimide (3.12 g, 17.5 mmol), and 2,2'-azobisisobutylonitrile (30 mg) were refluxed for 30 minutes in carbon tetrachloride (80 ml). After the reaction, the reaction solution was concentrated to half the volume, the precipitated solid was filtered off, and the solvent was removed from the filtrate. The residue was purified by column chromatography (developing solvent: benzene:ethyl acetate=8:2) to give yellow liquid (3.79 g). The resulting product was analyzed by gas chromatography and the area 5-methyl-1,3-dioxole-2-one [hereinafter to be referred to as Compound 59a] was roughly calculated to be approximately 70%. Accordingly, the content of Compound 59a in the above liquid was 2.65 g, yield, 78%. The product was used as such without purification.

[The Compound 59a is a known compound listed in Liebigs Ann. Chem. 1977, pages 27-32.]

(Preparation of desired compound)

The compound 11 (2.93 g, 6.85 mmol) and dry phthalidylidene (1.88 ml, 13.7 mmol) were stirred in dry acetone (60 ml) for 30 minutes to make a solution, into which was dropwise added the mixture obtained as above (3.79 g), which contained Compound 59a was 2.65 g, 13.7 mmol, dissolved in dry acetone (10 ml). After refluxing for 17 hours, the reaction solution was filtered to remove precipitate, the filtrate was concentrated, and the residue was extracted with chloroform (200 ml). The extract solution was washed with aqueous solution of NaHCO$_3$ (twice) and saturated aqueous solution of NaCl (twice) and dried over magnesium sulfate. The solvent was evaporated. The resulting yellow oily product was separated by column chromatography to give the desired compound (2.165 g, yield, 48%). (developing solvent: benzene:ether=9:1). The resulting white solid was recrystallized from methanol - THF - water to give white crystals (2.02 g). (Total yield from 4,5-dimethyl-1,3-dioxole-2-one was 35%.) m.p., 187°-189° C.

IR (KBr, cm$^{-1}$): 3310, 1825, 1740, 1690

$^1$H-NMR (CDCl$_3$, δ): 11.67 (S, 1H, CONH), 11.12 :S, 1H, CONH), 8.95-7.00 (m, aromatic hydrogen), 5.07 (S, 2H, —CH$_2$—), 4.81 (S, 2H, —CH—), 2.16 (S, 3H, —CH$_3$), 2.08 (S, 3H, —CH$_3$)

EXAMPLE 28

Preparation of high melting point form of 2,2'--[(1,3-dioxo-2-phenylmethylene-1,3-propanediyl)-diimino]bisbenzoic acid [Compound 11]

The low melting point form of Compound 11 (0.1 g) was charged into a mortar and crushed with a pestle. By this treatment, the low melting point form was changed into the high melting point form of the following properties: Melting point: 247°-249° C.

IR and NMR: Same as those of low melting point form.

Figure 5:
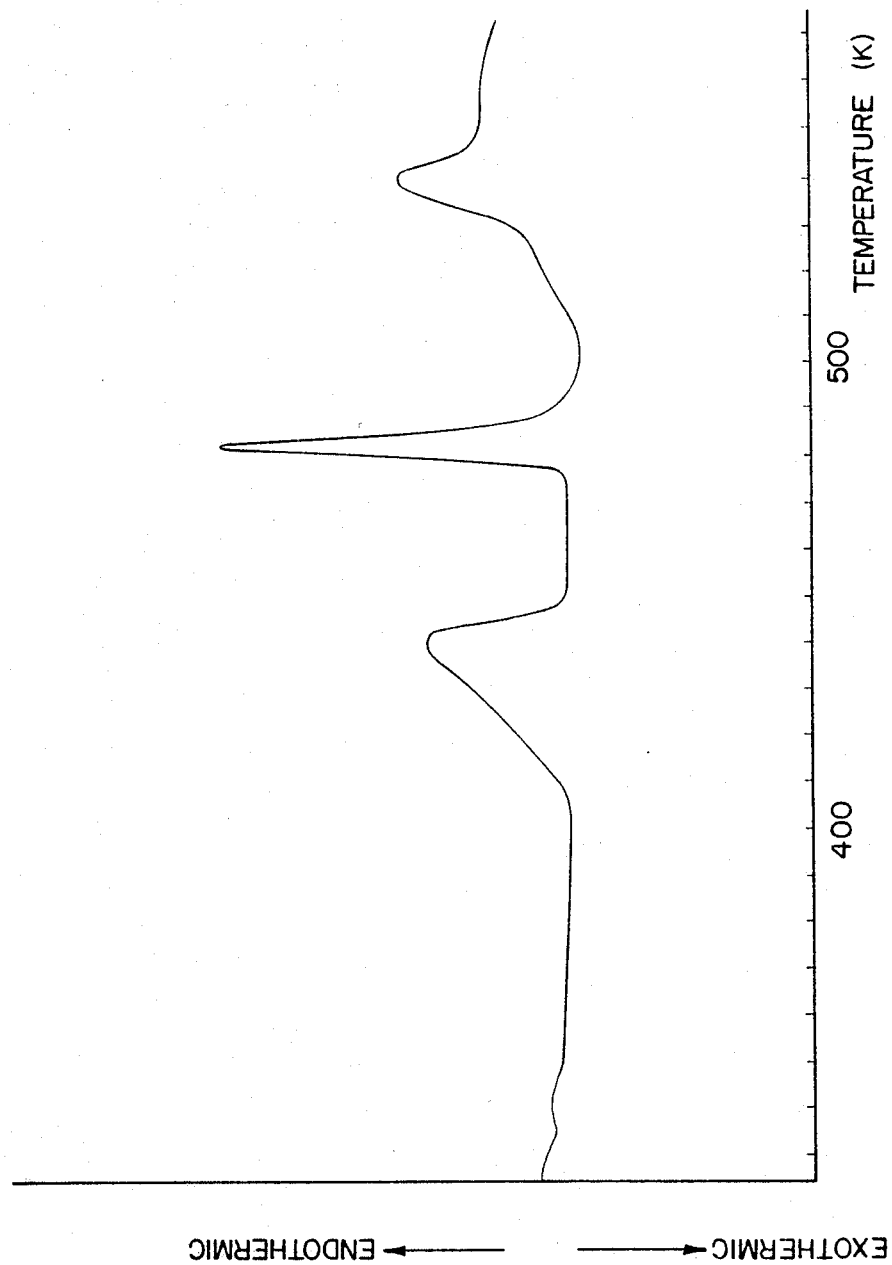
Figure 6:
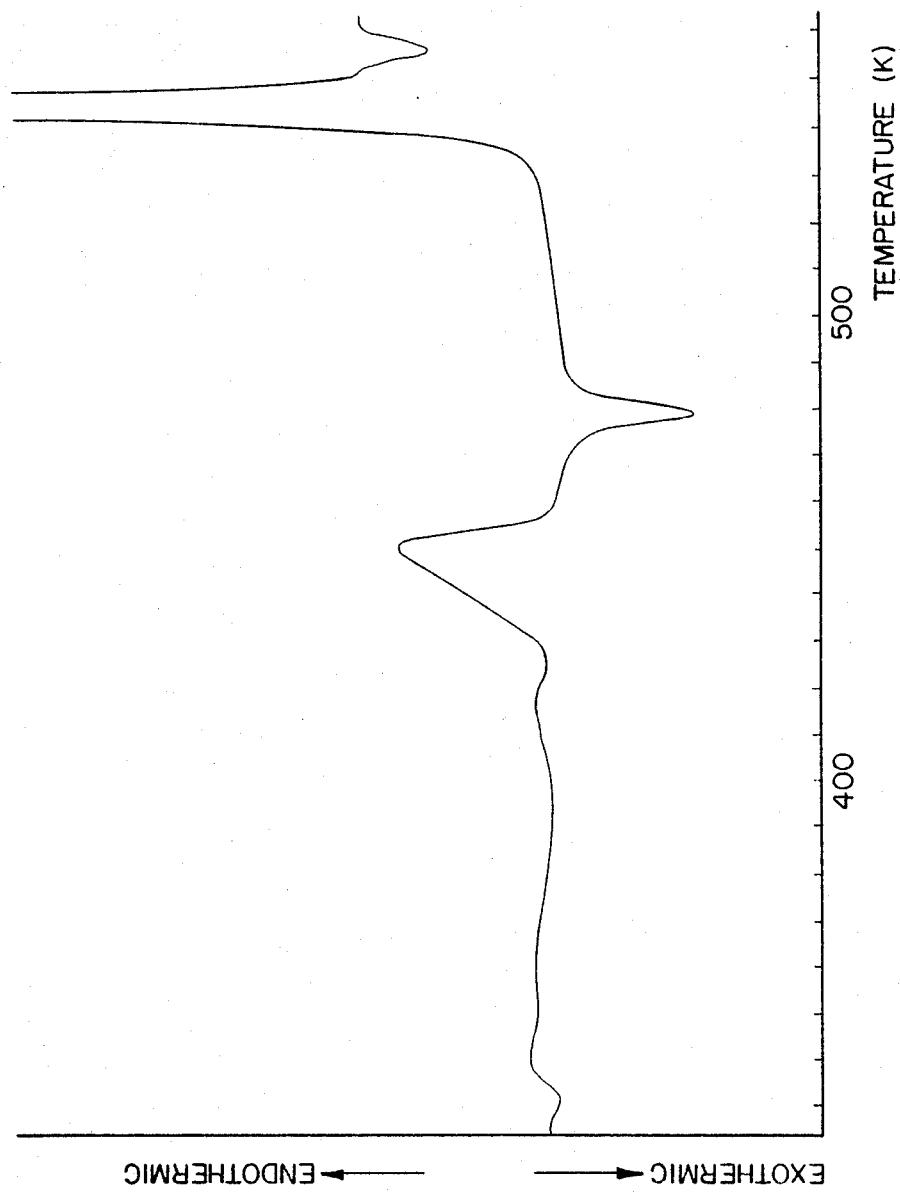

The differential thermal analysis curves of the above low melting point form and high melting point form are shown in FIG. 5 and FIG. 6.

EXAMPLE 29

Preparation of high melting point form of 2,2'-[(1,3-dioxo-2-(2-thienyl)methylene-1,3-propanediyl)diimino]bisbenzoic acid [Compound 40]

Figure 7:
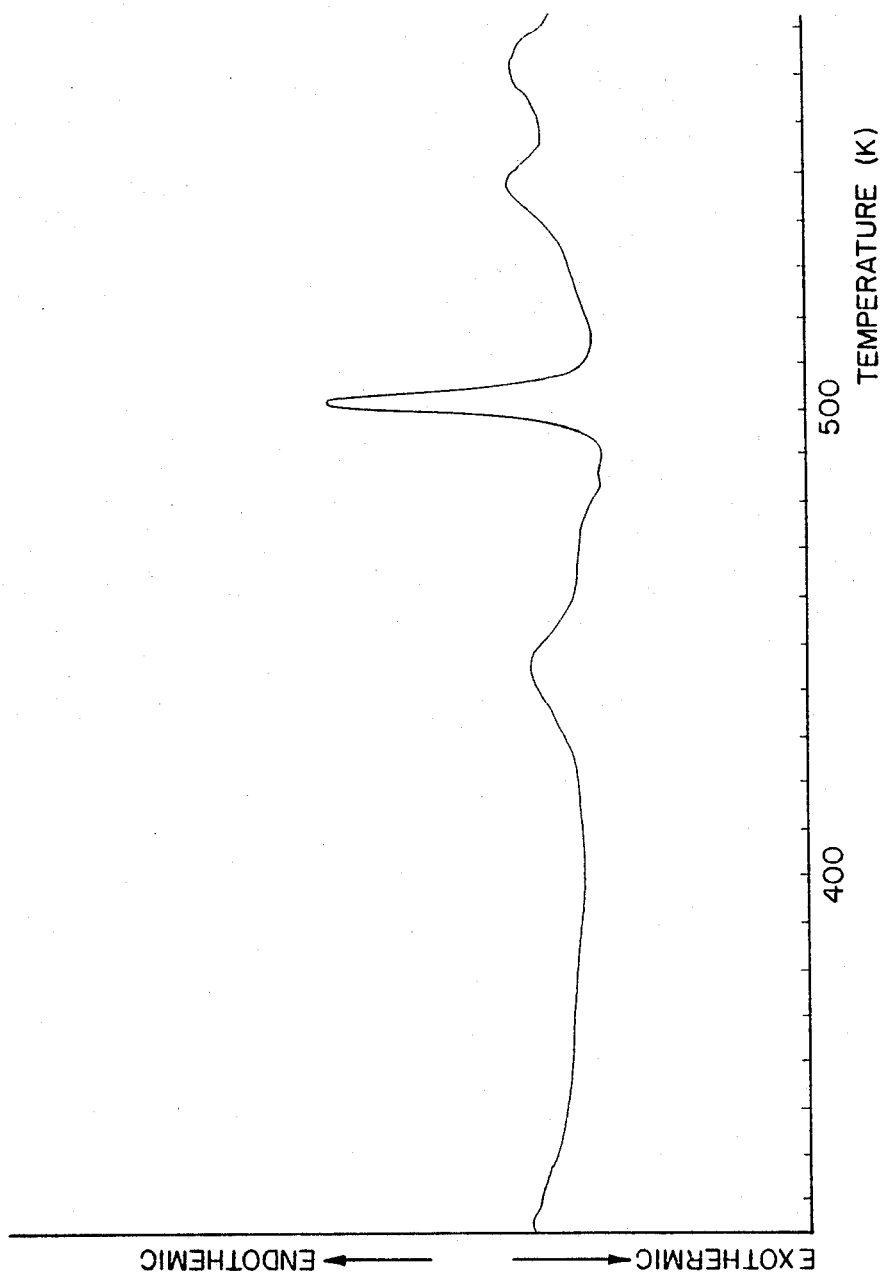
Figure 8:
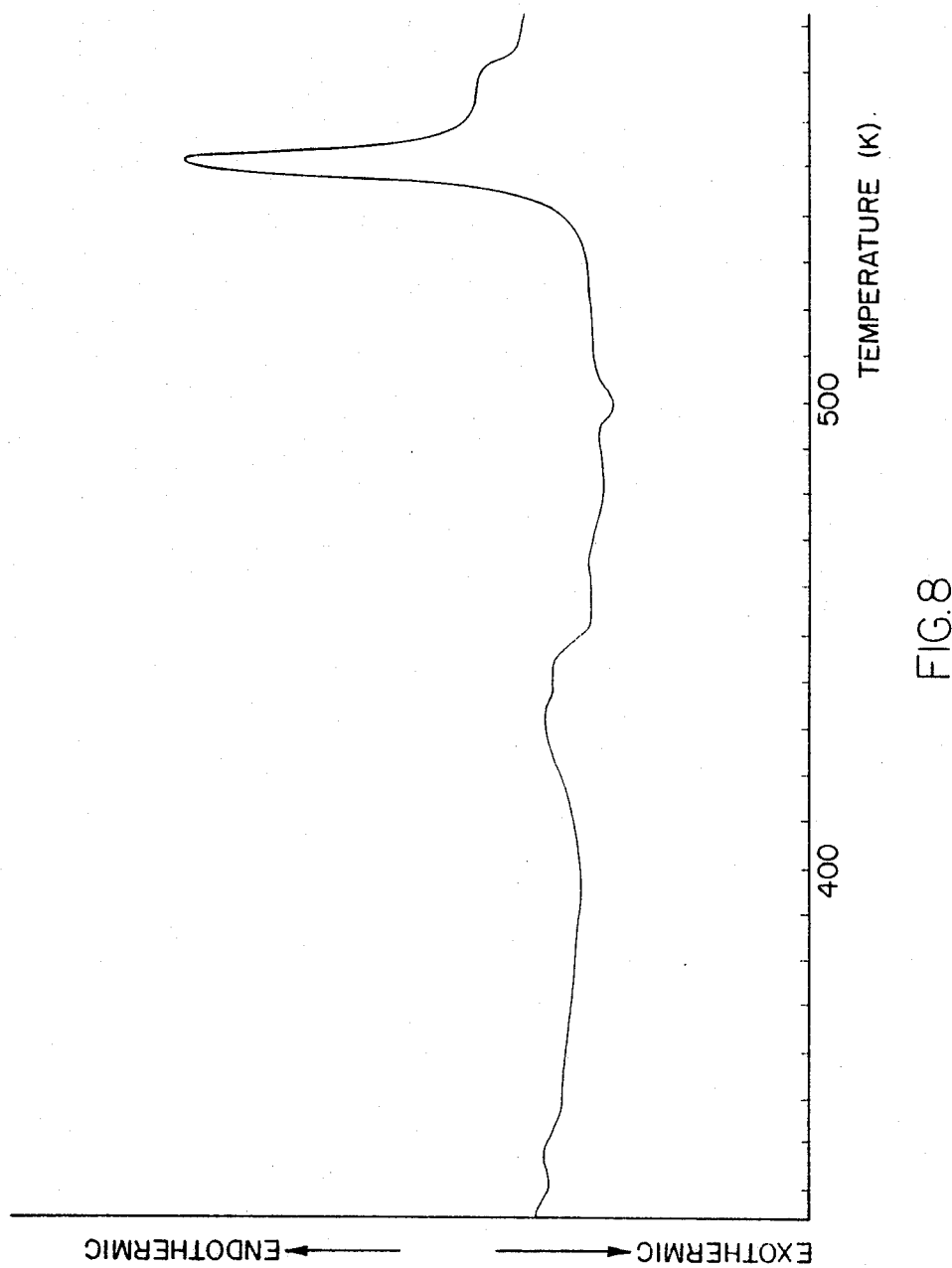

The low melting point form of Compound 40 was treated in the same manner as in Example 28 to obtain the high melting point form having the following properties:
Melting point: 243°–245° C.
IR and NMR: Same as those of low melting point form.
The differential thermal analysis curves of the above low melting point form and high melting point form are shown in FIG. 7 and FIG. 8.

EXAMPLE 30

Preparation of high melting point form of 2,2'-[(1,3-dioxo-2-(3-thienyl)methylene-1,3-propanediyl)diimino]bisbenzoic acid [Compound 41]

Figure 9:
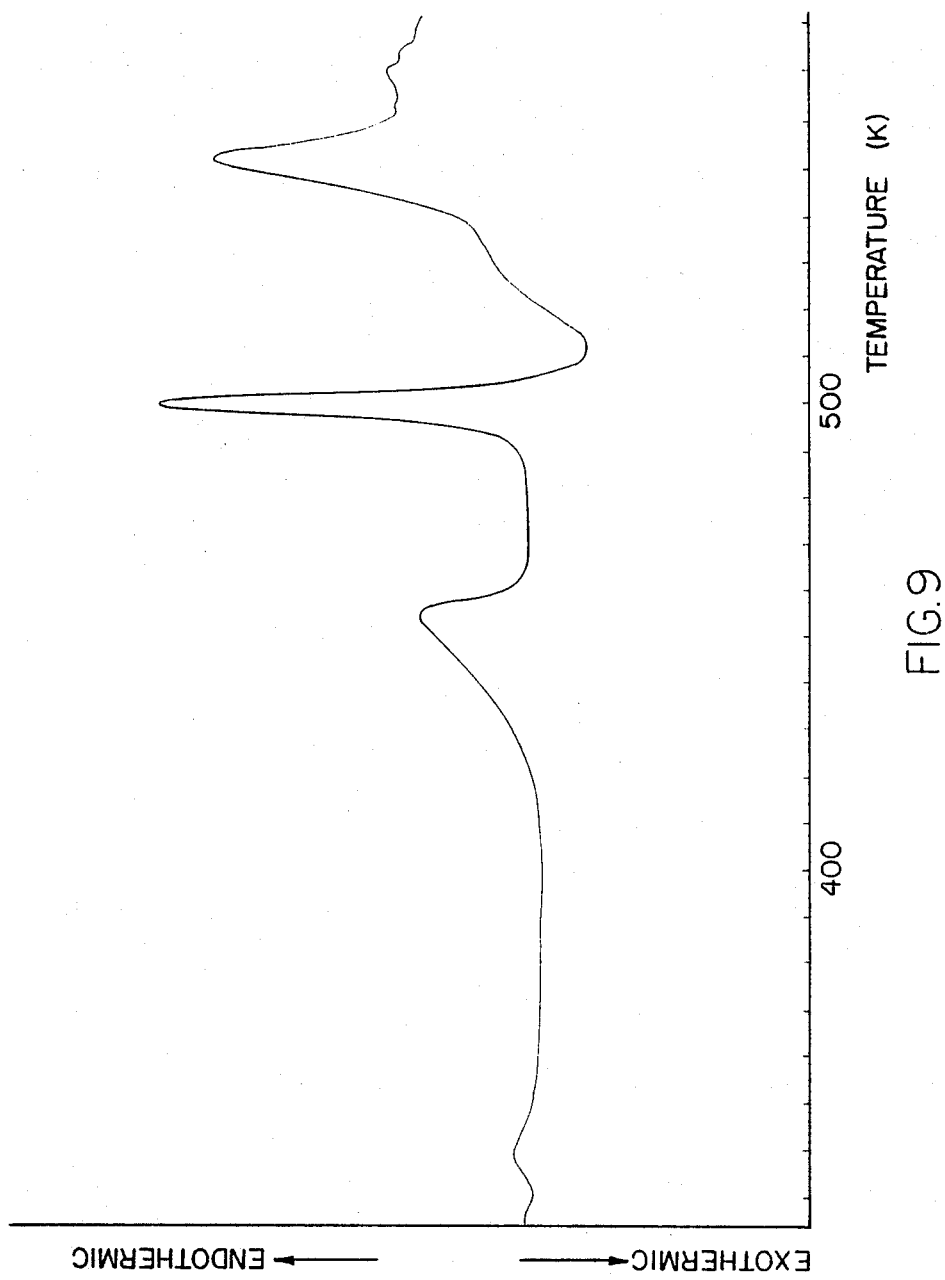
Figure 10:
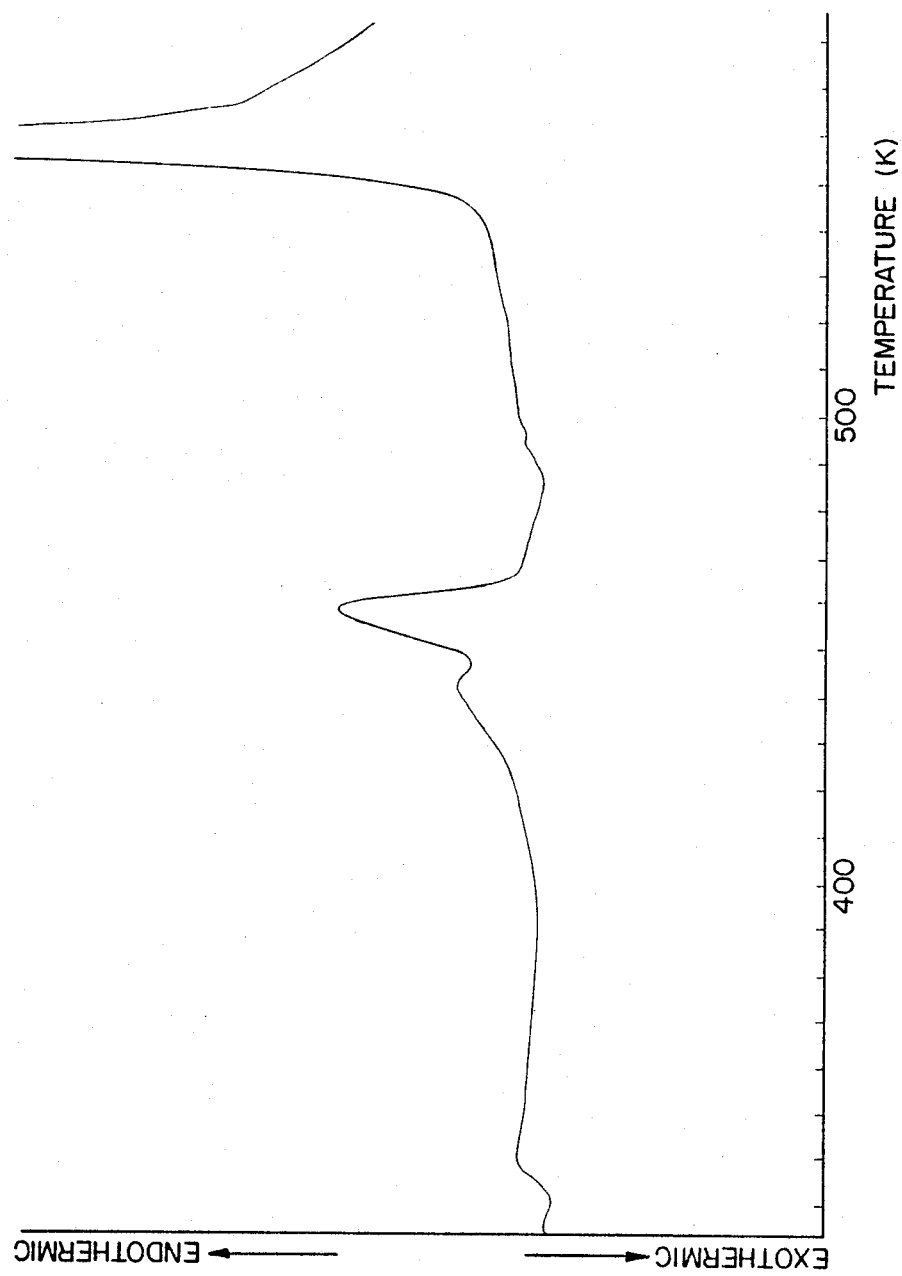

The low melting point form of Compound 41 was treated in the same manner as in Example 28 to obtain the high melting point form having the following properties:
Melting point: 245°–251° C.
IR and NMR: Same as those of low melting point form.
The differential thermal analysis curves of the above low melting point form and high melting point form are shown in FIG. 9 and FIG. 10.

EXAMPLE 31

Preparation of high melting point form of 2,2'-[(1,3-dioxo-2-(1-methyl-1H-pyrrol-2-yl)methylene-1,3-propanediyl)diimino]bisbenzoic acid [Compound 43]

Figure 11:
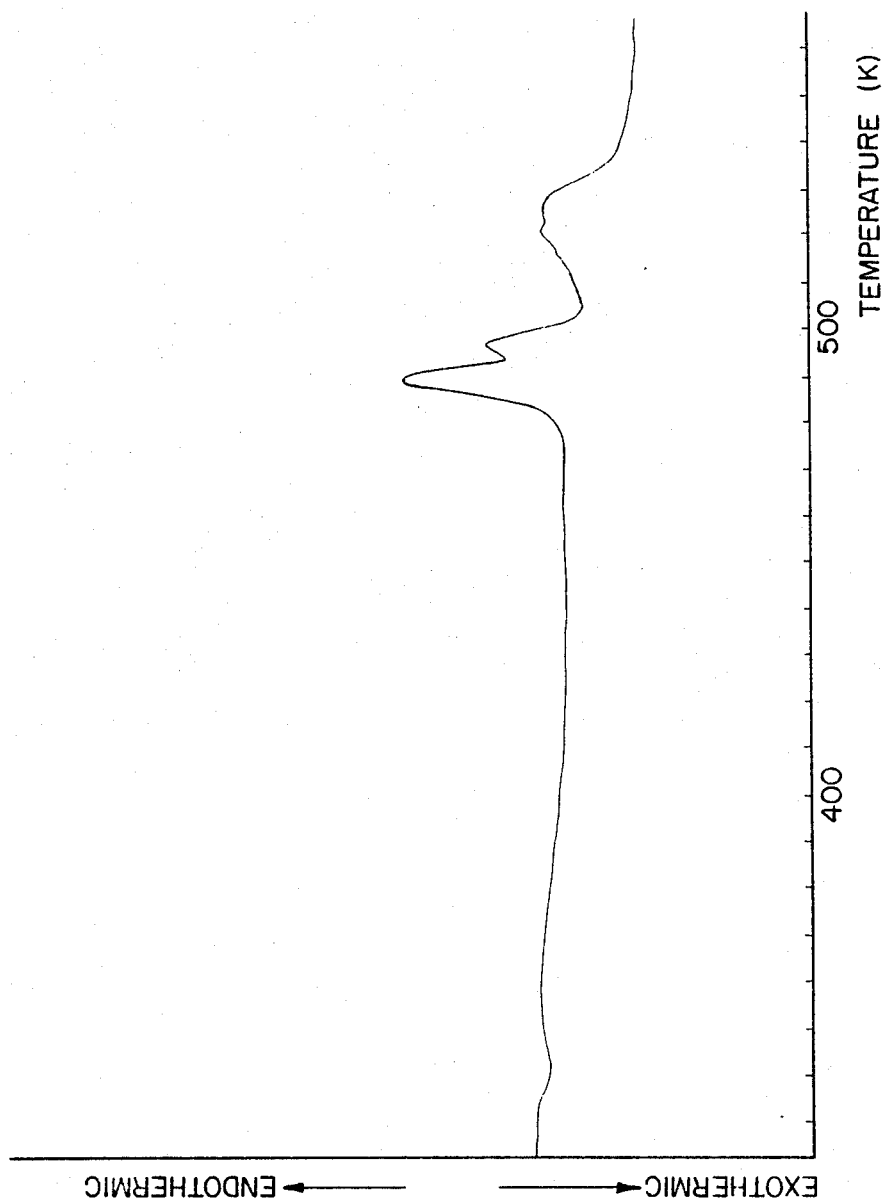
Figure 12:
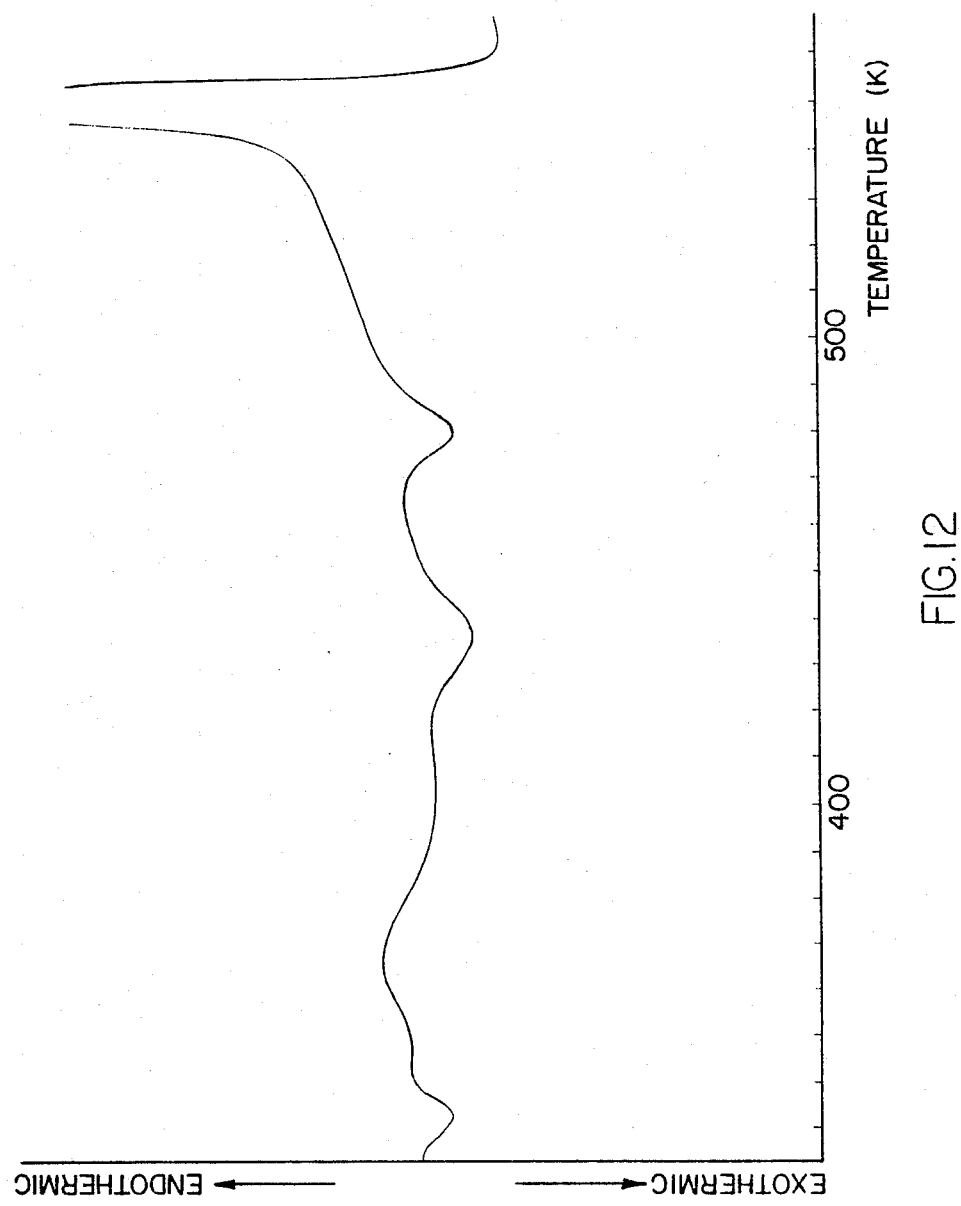

The low melting point form of compound 43 was treated in the same manner as in Example 28 to obtain the high melting point form having the following properties:
Melting point: 236°–241° C.
IR and NMR: Same as those of the low melting point one.
The differential thermal analysis curves of the above low melting point form and the high melting point form compounds are shown in FIG. 11 and FIG. 12.

EXAMPLE 32

Preparation of 2,2'-phenylethenilidenbis(3,1-benzoxazine-4-one)(Compound 52)

The Compound 11 (4 g, 9.28 mmol) was suspended in dry benzene (100 ml) and oxalyl chloride (3.2 ml, 37.18 mmol) was added dropwise under ice cooling. Then, with addition cf 8 drops of dry DMF, the mixture was stirred at room temperature for 2 hours. After the reaction, the solvent was removed and the residue was extracted with chloroform. The organic layer was washed with 1N.HCl, saturated brine, 4% NaHCO$_3$ aqueous solution, and saturated brine and dried over magnesium sulfate. The solvent was evaporated. The residue was dissolved in chlcroform and applied on silica gel column for chromatography (benzene ethyl acetate=4:1). Recrystallization from isopropyl ether gave the desired compound 52 in crystal (3.26 g, yield, 89%). m.p., IR, and NMR pectra of the product fully agreed with those of the one obtained in Example 19.

EXAMPLE 33

Preparation of 2,2'-phenylethenilidenebis(3,1-benzoxazine-4-one)(Compound 52)

Under nitrogen gas current, 2-chloro-N-methylpyridinium iodide (691 mg, 2.78 mmol) was suspensed in dry methylene chloride (5 ml) and a solution of Compound 11 (500 mg, 1.16 mmol) and dry triethylamine (0.76 ml, 5.57 mmol) in dry methylene chloride (5 ml) were added. The mixture was stirred at 40° C. for 3.5 hours. After the reaction, methylene chloride was added, and the mixture was washed with 1N.HCl, water, 4% NaHCO$_3$ aqueous solution and water and dried over magnesium sulfate. The solvent was evaporated. The residue was crystallized rrcm isopropylether to give the desired compound 52 in crystal (410 mg, yield, 90%). m.p., IR, and NMR spectra of the product fully agreed with those of the one obtained in Example 19.

EXAMPLE 34

Preparation of 2,2'-phenylethenilidenbis(3,1-benzoxazin-4-on)(Compound 52)

The Compound 11 (500 mg, 1.16 mmol) and 4-dimethylaminopyridine (28 mg, 0.23 mmol) were suspended in dry methylene chloride (10 ml) and dicyclohexylcarbodiimide (605 mg, 2.78 mmol) was added under ice cooling. The mixture was stirred at 40° C. for 3.5 hours. After the reaction, the insoluble matter was filtered off, and methylene chloride was added to the filtrate, which was washed with 1N.HCl, water, 4% aqueous solution of NaHCO$_3$ and water and dried over magnesium sulfate. The solvent was evaporated. The residue was crystallized from isopropyl ether to give the desired ccmpound 52 in crystal (415 mg, yield, 91%). m.p., IR, NMR spectra of the product fully agreed with those of the one obtained in Example 19.

Alternatively, by the reaction as in Example 32 using thionyl chloride in place of oxalyl chloride in benzene at room temperature for 2 hours, or using phosphorus oxychloride in benzene at 80° C. for 2 hours, or as in Example 36 using N,N'-carbonyldiimidazole in place of dicyclohexylcarbodiimide in tetrahydrofuran at room temperature for 2 hours, the desired compound 52 could also be obtained in a high yield.

EXAMPLE 35

Preparation of 2,2'-phenylethenilidenbis(3,1-benzoxazine-4-one)(Compound 52)

Benzaldehyde 259 mg, 2.45 mmol), Compound (2,2'-methylenebis(3,1-benzoxazine-4-one) (500 mg, 1.63 mmol), and BF$_3$.(C$_2$H$_5$)$_2$O (0.045 ml, 0.163 mmol) where heated under reflux in dry toluene (20 ml) for 20 hours. After the reaction, the solvent was removed under reduced pressure from the reaction mixture, the residue was treated with water, extracted with benzene, and the organic layer was separated, washed with water and dried over magnesium sulfate. The solvent was evaporated under reduced pressure. The residue was dissolved in the developing solvent and adsorbed on silica gel, and was purified by column chromatography to give the desired compound 52. The obtained product was crystallized from isopropylether to give the desired compound 52 in white solid in a good yield. m.p., IR, and NMR spectra of the product fully agreed with those of the one obtained in Example 19.

Example 36

Preparation of 2,2'-[1,3-Dioxo-2-phenylmethylene-1,3-propanediyl]diimino]bisbenzoic acid dipotassium salt Potassium carbonate (321 mg, 2.32 mmol) was dissolved in water (5 ml). The solution was heated to 80° C., treated with the Compound 11 (1.0 g, 2.32 mmol), and stirred for 3 hours. After cooling, the reaction mixture was sucked on a filter, and the solvent was removed from the filtrate. The residue was treated with acetone and crystallized to give the desired potassium salt in white solid (1.165 g, yield, 99.1%). m.p., 240°–245° C.

IR (KBr, $cm^{-1}$): 3400 (broad), 1685, 1490

$^1$H-NMR (DMSO-$d_6$,$\delta$): 6.92–8.73 (m, 14H, aromatic hydrogen, vinyl hydrogen), 14.77 (brs, 1H, —CON$\underline{H}$—), 15.22 (brs, 1H, —CON$\underline{H}$—)

EXAMPLE 37

Preparation of 2,2'-[[1,3-dioxo-2-phenylmethylene-1,3-propanediyl]-diimino]bisbenzoic acid calcium salt The Compound 11 (430 mg 1 mmol) was treated with THF (20 ml) and water (10 ml), and further with calcium carbonate (100 mg, 1 mmol), and the mixture was stirred at room temperature for 24 hours. The reaction mixture was filtered by suction, and the solvent was removed from the filtrate. The residue was washed with acetone to give the desired calcium salt in pale yellow solid (420 mg, yield, 89.6%). m.p., 300° C. or higher.

IR (KBr, $cm^{-1}$); 3400 (broad), 1650, 1585, 1490

$^1$H-NMR (DMSO-$d_6$,$\delta$): 6.80–8.78 (m, 14H, aromatic hydrogen, vinyl hydrogen), 13.72 (brs, 1H, —CON$\underline{H}$—), 14.37 (brs, 1H, —CON$\underline{H}$)

EXAMPLE 38

Preparation of 2,2'-[[1,3-dioxo-2-phenylmethylene1,3-propanediyl]-diimino]bisbenzoic acid di(L-lysine) salt The Compound 11 (500 mg, 1.20 mmol) was dissolved in THF (5 ml), and L-lysine (351 mg, 2.40 mmol) dissolved in water (3 ml) was added.

The mixture was stirred at room temperature for 1 hour, after which the solvent was removed under reduced pressure. The residue was treated with THF and stirred for 1 hour to crystallize. The crystals were filtered and dried to give a pale yellow solid (780 mg.) The resulting solid was dissolved in water, and after filtering off the insoluble matter, water was removed under reduced pressure. The residue was crystallized from ether to give the desired compound as pale yellow solid (630 mg, yield, 74%). m.p., 176°–181° C.

IR (KBr, $cm^{-1}$); 3700–2200, 1580

$^1$H-NMR (DMSO-$d_6$,$\delta$): 14.45 (s, 1H, —CON$\underline{H}$—), 14.05 (s, 1H, —CON$\underline{H}$—), 8.03–6.87 (m, aromatic hydrogen, vinyl hydrogen), 3.35 (br), 2.67 (br), 1.47 (br)

EXAMPLE 39

Preparation of 2,2'-[[1,3-dioxo-2-phenylmethylene-1,3-propanediyl]-diimino]bisbenzoic acid di(L-arcinine) salt The Compound 11 (500 mg, 1.20 mmol) was dissolved in THF (5 ml), and L-arginine (418 mg, 2.40 mmol) dissolved in water (3 ml) was added. After stirring the mixture at room tempertrure for 1 hour, solvent was removed under reduced pressure. The residue was treated with THF and stirred for 1 hour to crystallize.

The crystals were filtered and dried to give a pale yellow solid (828 mg). The resulting solid was dissolved in water, and after filtering off the insoluble matter, water was removed under reduced pressure. The residue was crystallized from ether to give the desired compound as pale yellow solid (650 mg, yield, 71%). m.p., 191°–195° C.

IR (KBr, $cm^{-1}$): 3700–2200, 1580, 1620 (br)

$^1$H-NMR (DMSO-$d_6$,$\delta$): 14.38 (s, 1H, —CON$\underline{H}$—), 13.93 (s, 1H, —CON$\underline{H}$—), 8.67–6.87 (m, aromatic hydrogen, vinyl hydrogen), 3.35 (br), 3.07 (br), 1.68 (br)

EXAMPLE 40

| (1) | Active ingredient | 25.00 mg |
|---|---|---|
| (2) | Lactose | 49.00 mg |
|  | Crystalline cellulose | 36.00 mg |
|  | Corn starch | 5.00 mg |
| (3) | Hydroxypropyl cellulose | 1.00 mg |
| (4) | ECG505 (carboxymethyl cellulose calcium) | 2.00 mg |
| (5) | Magnesium stearate | 1.00 mg |
| (6) | Talc | 1.00 mg |
|  | Total | 120 mg |

(1)+(2) were kneaded with 5% aqueous solution of (3), dried, and granulated, to which (4), (5), and (6) were added to mix together. The mixture was pressed into tablets of 120 mg each, 7 mm in diameter.

EXAMPLE 41

| (1) | Active ingredient | 50.00 mg |
|---|---|---|
| (2) | Lactose | 124.50 mg |
| (3) | Corn starch | 20.00 mg |
| (4) | Hydroxypropyl cellulose | 2.00 mg |
| (5) | Light anhydrous silicic acid | 1.50 mg |
| (6) | Magnesium stearate | 2.00 mg |
|  | Total | 200 mg |

(1)+(2)+(3) were kneaded with 5% aqueous solution of (4), dried, and granulated, to which (5) and (6) were added to mix together, and the mixture was filled in No. 3 hard capsules at the rate of 200 mg per capsule.

(In the above Examples 40 and 41, the term active ingredient means optional one of the compounds of the formula (I').

TEST EXAMPLE 1

Anti-hyaluronidase activity

It is known that, from the fact that disodium cromoglicate (DSCG), tranilast, etc. which are the anti-allergic agents inhibit hyaluronidase activity and the compound 48/80 and polymixin B which release histamine from the mast cell activate hyaluronidase, the hyaluronidase inhibiting activity can be made the index of the anti-allergic action. [The 5th Medicinal Chemistry Svmposium (Dec. 9 & 10, 1983, in Kyoto) Synopsis of Lectures, page 68]. As a result of the tests for the anti-hyaluronidase activity on the compounds according to the present invention, they have been found to have the excellent activities.

(Test Method)

A buffer solution of hyaluronidase (0.1 ml) was taken in a test tube and 0.2 ml each of the buffer solution of various compounds in various concentrations was added, and the mixture was preincubated at 37° C. for 20 minutes. Then, an activating agent (Compound 48/80 or $CaCl_2$) (0.2 ml) was added to make the total amount 0.5 ml, which was incubated at 37° C. for 20 minutes. Then, potassium hyaluronate buffer solution (0.5 ml) was added, and the mixture was incubated at 37° C. for 40 minutes. After cooling, the mixture was treated with aqueous solution of 0.4N NaOH (0.2 ml) and neutralized to stop the reaction. The resulting product was subjecred to measurement of $OD_{585}$ by the modified Morgan-Elson Method. As the control, buffer solution or water (0.2 ml) instead of various compounds was subjected to the similar operations and $OD_{585}$ was determined. (The final concentration of hyaluronidase was 340NF unit/ml.)

$$\text{Inhibition rate} = \frac{(\text{Control } OD_{585} - \text{Sample } OD_{585}) \times 100}{\text{Control } OD_{585}}$$

| Compound | $IC_{50}$ (mM) | Compound | $IC_{50}$ (mM) |
|---|---|---|---|
| 01 | 0.077 | 31 | 0.025 |
| 02 | 0.900 ($IC_{20}$) | 32 | 0.025 |
| 04 | 0.015 ($IC_{10}$) | 33 | 0.015 |
| 05 | 1.320 ($IC_{10}$) | 34 | 0.025 |
| 06 | 0.013 | 35 | 0.015 |
| 07 | 0.660 ($IC_{10}$), 0.720 ($IC_{20}$) | 36 | 0.025 |
| 08 | 0.220 ($IC_{10}$) | 37 | 0.017 |
| 09 | 0.134 | 38 | 0.023 |
| 11 | 0.022 | 39 | 0.040 |
| 12 | 0.065 | 40 | 0.035 |
| 13 | 0.055 | 41 | 0.060 |
| 15 | 0.055 | 42 | 0.025 |
| 16 | 0.010 | 43 | 0.040 |
| 17 | 0.142 | 44 | 0.073 |
| 18 | 0.290 ($IC_{10}$) | 45 | 0.010 |
| 19 | 0.013 | 46 | 0.030 |
| 20 | 0.040 | 49 | 0.035 |
| 21 | 0.015 | 50 | 0.050 |
| 22 | 0.008 | | |
| 23 | 0.030 | | |
| 24 | 0.020 | | |
| 25 | 0.013 | | |
| 26 | 0.020 | | |
| 27 | 0.030 | | |
| 28 | 0.110 | | |
| 29 | 0.020 | | |
| 30 | 0.010 | | |

As shown in the table, all the tested compounds were found to have strong hyaluronidase activity inhibiting actions.

TEST EXAMPLE 2

Anti-passive cutaneous anaohylaxis (PCA) activity in rats (Test method)

Wistar strain rats were sensitized with ovalbumin using aluminium hydroxide gel and Bordetella Pertussis vaccine as adjuvants. Dilutions of antiserum (16-fold and 32-fold) obtained by collecting blood samples 14 days later were administered subcutaneously in the dorsal skin of the rats of the same strain at the rate of 0.1 ml per spot, and the rats were grown for 48 hours. One hour after peroral administration of the sample solution, a mixture of antigen ovalbumin and Evans-blue dye was administered to the tail venous of the animal according to the ordinary procedure. Thirty minutes later, the animals were sacrificed by exsanguination, and the areas of blue spots (long diameter × short diameter) eliciting on the portion of the antiserum injection at the dorsal skin were measured to obtain the rate of inhibition based on the average value shown by the control animals.

(Results)

| | | | | Anti-PCA activity | |
|---|---|---|---|---|---|
| | Dose mg/kg | | | Average Inhibition Rate (%) | |
| Com-pound | Route of admin. | | (N) | Antiserum Dilution: × 16 | Antiserum Dilution: × 32 |
| Control | — | PO | 10 | 0 | 0 |
| Tranilast | 200 | PO | 10 | 1.8 | 15.8 |
| DSCG | 100 | PO | 10 | 0.1 | 0.3 |
| 11 | 10 | PO | 10 | 23.2 | 33.1 |
| | 50 | PO | 10 | 41.4 | 39.1 |
| | 100 | PO | 10 | 52.9 | 53.5 |
| 06 | 10 | PO | 10 | 8.5 | 11.2 |
| | 50 | PO | 10 | 14.9 | 13.3 |
| | 100 | PO | 10 | 18.6 | 18.8 |
| 16 | 50 | PO | 10 | 3.2 | 9.0 |
| | 100 | PO | 10 | 11.8 | 12.2 |
| 22 | 50 | PO | 10 | 19.7 | 22.6 |
| | 100 | PO | 10 | 34.6 | 40.0 |
| 26 | 50 | PO | 10 | 8.3 | 10.0 |
| | 100 | PO | 10 | 16.4 | 19.1 |
| 29 | 100 | PO | 10 | 3.4 | 3.9 |
| 30 | 10 | PO | 10 | 18.8 | 23.2 |
| | 50 | PO | 10 | 23.4 | 33.3 |
| | 100 | PO | 10 | 36.5 | 42.5 |
| 14 | 10 | PO | 10 | 38.6 | 38.7 |
| | 50 | PO | 10 | 41.9 | 72.2 |
| | 100 | PO | 10 | 59.3 | 85.1 |
| 52 | 10 | PO | 10 | 20.6 | 29.4 |
| | 50 | PO | 10 | 37.9 | 38.3 |
| | 100 | PO | 10 | 45.0 | 47.1 |

As shown in the above table, all the compounds were found tc shcw anti-PCA activity by peroral administration. The control discdium cromoglicate showed no activity by peroral administration.

TEST EXAMPLE 3

Effect on reaction of oassive sensitized guinea pig to inhalated antigen (Test method)

The compound 11 was compared with Tranilast and disodium cromoglicate in the experimental asthma models.

(1) Preparation of sample solution:

The test compound and Tranilast were respectively suspended at the time of use in 5% gum arabic solution containing 0.1% Tween 80 at the rate of 40 mg/ml, and were perorally administered at the rate of 0.5 ml per 100 g body weight of the animal.

DSCG was dissolved at the time of use in physiological saline solution for injection at the rate of 5.0 mg/ml, and was intravenously injected at the rate of 0.1 ml per 100 g body weight of the animal.

(2) Antigen inhalation test on passive sensitized guinea pig:

Anti-ovalbumin rabbit serum diluted with physiological saline solution for injection so as to contain anti-ovalbumin rabbit antibody at the rate of 0.187 mg N/ml was intravenously administered to guinea pig at the rate of 0.1 ml per 100 g of body weight and it was passively sensitized.

Twenty-four hours later, the suspension of the compound prepared in (1) above was perorally or intravenously administered to the animal. The animal was put in the inhalation chamber one hour after the administration in case of the peroral administration and five minutes after the administration in case of the intravenous administration, and 2% physiological saline solution of antigen ovalbumin was inhaled by spraying. Over 10 minutes' period from the time immediately after the forced inhalation, the time until its fall attributed to anaphylaxis reaction was recorded, and the numbers of alive and dead animals after lapse of 10 minutes were also counted.

(Results)

| Compound | Dose mg/kg | N | Required time (sec.) for falling and Number of death (#) | | | | | Average time for falling Mean ± S.E. | Extended rate (%) |
|---|---|---|---|---|---|---|---|---|---|
| Control | — | po | 5 | #123 #139 #152 #160 | | | 203 | 155.4 ± 13.4 | |
| 11 | 200 | po | 5 | #194 227 248 600< | | | 600< | 223.0 ± 15.7* | 43.5 |
| tranilast | 200 | po | 5 | #116 #126 #141 #181 | | | #190 | 150.8 ± 14.8 NS | −3.0 |
| DSCG | 5 | iv | 5 | #142 188 #199 241 | | | 600< | 192.5 ± 20.3 NS | 23.9 |

(Note)
NS shows no significant difference, *shows 0.01 < P < 0.05, # shows death.

As shown in Table, Compound 11 showed a strong preventive effect on anaphylaxis reaction to the experimental asthma models, well surpassing the action of 5 mg/kg sodium cromoglicate for venous injection, while Tranilast showed no activity in the present test method.

TEST EXAMPLE 4

Study on Anti-ulcer activity in experimental ulcer model (Shay)

Study was made on the anti-ulcer activity of the test compound.

(Animals used)

Using 5 eight-week old Wistar strain male rats of 1 group, the rats were previously fasted for 4.8 hours. The compound of an amount proportionate to the body weight based on the body weight after fasting was administered intraduodenally or intraperitoneally.

(Preparation of sample solution)

Each test compound was evenly suspended or dissolved in an aqueous solution of 0.5% CMC containing 0.1% Tween 80, and administered at the rate of 0.5 ml per 100 g of body weight of the animal. To the controls, only the solvent was administered.

(Test method)

Test was carried out in accordance with Shay's method. After 48 hours' fasting, 5 animals per group were subjected to laparotomy under ether anesthesia, the tract between pylorus of stomach and duodenum was ligated, and the solution of the compound was administered intraduodenally (id) or intraperitoneally (ip), followed by suturing the laparotomy part. Eight hours after administration of the compound liquid, each animal was sacrificed by ether anesthesia and stomach was removed. Then, evaluation on the ulcer condition on the inner surface of stomach, and determination of the amount of gastric juice, of acidity by alkali titration, and of pepsin titer based on substrate of hemoglovin were made on the stored gastric juice. With regard to the acidity, gastric juice amount, and pepsin titer, the results were shown in inhibition rate (%) based on the average value of the control groups.

(Results)

As shown in the Table, the compound used showed excellent results in ulcer index and inhibition of gastric acid, of secretion amount of gastric juice, and of total pepsin titer.

| Anti-ulcer activity in experimental ulcer model (Shav) | | | | | | | | | | | |
|---|---|---|---|---|---|---|---|---|---|---|---|
| | | | | | | | | | | | (n = 5) |
| | | | | | | | | | | Inhibition % | |
| | | | | | | | | | | | |
| | | | | | | | | | Gastric Acidity | secretion amount of gastric juice | total pepsin titer |
| Compound | Route | Dose (mg/kg) | Ulcer Index *1 | | | | | | | | |
| | | | 0 | 1 | 2 | 3 | 4 | 5 | | | |
| Control | id | — | 0 | 0 | 1 | 3 | 1 | 0 | 0 | 0 | 0 |
| Ranitidine | id | 30 | 1 | 4 | 0 | 0 | 0 | 0 | 63.0 | 25.2 | 20.6 |
| 11 | id | 100 | 0 | 0 | 3 | 2 | 0 | 0 | 4.7 | 0 | 0 |
| | id | 200 | 0 | 1 | 2 | 2 | 0 | 0 | 16.5 | 20.1 | 9.1 |
| 20 | id | 100 | 1 | 3 | 1 | 0 | 0 | 0 | 64.5 | 28.1 | 42.5 |
| | id | 200 | 2 | 2 | 1 | 0 | 0 | 0 | 99.5 | 59.0 | 69.3 |
| | ip | 10 | 1 | 3 | 1 | 0 | 0 | 0 | 52.3 | 26.3 | 31.4 |
| | ip | 50 | 4 | 1 | 0 | 0 | 0 | 0 | 88.0 | 70.9 | 60.7 |
| 23 | id | 100 | 0 | 0 | 2 | 2 | 1 | 0 | 32.5 | 8.5 | 31.1 |
| | id | 200 | 0 | 2 | 3 | 0 | 0 | 0 | 40.2 | 11.2 | 41.2 |
| 25 | id | 100 | 0 | 0 | 1 | 3 | 1 | 0 | 45.2 | 25.5 | 32.1 |
| | id | 200 | 0 | 1 | 2 | 2 | 0 | 0 | 80.0 | 50.7 | 40.5 |
| | ip | 50 | 2 | 1 | 2 | 0 | 0 | 0 | 67.4 | 53.4 | 82.2 |
| 29 | id | 100 | 0 | 0 | 0 | 4 | 1 | 0 | 0 | 0 | 0 |

-continued

Anti-ulcer activity in experimental ulcer model (Shav)

| Compound | Route | Dose (mg/kg) | Ulcer Index *1 | | | | | | Inhibition % | | |
|---|---|---|---|---|---|---|---|---|---|---|---|
| | | | 0 | 1 | 2 | 3 | 4 | 5 | Gastric Acidity | secretion amount of gastric juice | total pepsin titer |
| 22 | id | 200 | 0 | 0 | 0 | 3 | 2 | 0 | 0.7 | 0.5 | 0 |
| | id | 100 | 0 | 0 | 1 | 3 | 1 | 0 | 9.1 | 11.1 | 7.2 |
| | id | 200 | 0 | 0 | 1 | 3 | 1 | 0 | 13.2 | 11.6 | 10.1 |
| | id | 300 | 0 | 0 | 0 | 4 | 1 | 0 | 15.7 | 24.9 | 8.3 |
| | ip | 50 | 0 | 2 | 2 | 1 | 0 | 0 | 38.2 | 29.0 | 37.2 |

(n = 5)

*1: Ulcer index of Adami

TEST EXAMPLE 5

Anti-SRS-A activity (Method of preparing crude SRS-A solution)

A piece of lungs of guinea pig sensitized with ovalbumin was incubated with antigen ovalbumin at 37° C. for 20 minutes to obtain a supernatant solution, which was used as a crude SRS-A solution.

(Determination of anti-SRS-A reaction)

A piece of ileum of normal guinea pig was suspended in Magnus tube filled with Tyrode's solution and incubated with the solution of drug to be examined for a certain duration, and the contraction of the piece of ileum induced by adding the above crude SRS-A solution was determined on the basis of the contraction rate attributed to hystamine dihydrochloride $10^{-6}$M. The rate of inhibition against the contraction amount was taken as anti-SRS-A activity.

(Result)

| Compound | Anti-SRS-A activity | | | | |
|---|---|---|---|---|---|
| | $10^{-6}$ | $10^{-5}$ | $10^{-4}$ | $10^{-3}$ | (M) |
| Tranilast | 0 | 0 | 0 | 0 | |
| 11 | 0 | 0 | 0 | 31.8 | |

The test compound 11 showed a moderate anti-SRS-A activity at a concentration of $10^{-3}$M. To the contrary, no activity was noticed with Tranilast which was used as control.

TEST EXAMPLE 6

Activity of inhibition of histamine release from mast cell in abdominal cavity in rat Examination was made on the activity of inhibition of histamine release from mast cell by antigen-antibody reaction.

(Preparing of DNP-Ascaris anti-serum)

Swine ascaris extract solution was dinitrophenylated according to Aisen's method, dialysed, and lyophilized. The product was administered as antigen together with Bordetella Pertussis vaccine subcutaneously into the foot pad of rat. Eight days later, blood was taken to obtain antiserum. The PCA titer for this antiserum in rat was 32 to 64.

(Method of collecting mast cell in abdominal cavity and sensitizing cell)

Heparin-containing PBS was injected intraperitoneally to rat which was sacrificed by exsanguination, after which the abdomen was well massaged to collect the injected PBS, which was purified by washing several times by centrifugation. The number of the mast cells contained in the solution was determined and adjusted to the designed concentration. As to method of sensitizing the cell, the above cell suspension (6 ml, $2 \times 10^6$ cells/ml) was treated with anti-DNP-Ascaris rat serum (PCA titer 32) (6 ml) and the mixture was incubated in the presence of hepain at 37° C. for 2 hours.

(Quantitative determination of released histamine)

To the sensitized mast cell suspension the solution of the drug to be tested was added, and the mixture was preliminarily incubated at 37° C. for 12 minutes. After addition of the solution of antigen DNP-Ascaris (final concentration, 20 microgramms/ml), the mixture was further incubated for 20 minutes. After completion of the reaction, the solution was centrifuged (500 G, 10 min.) under a low temperature to obtain a supernatant solution. Histamine contained in the supernatant solution was subjected to fluorometry by crthophthalaldehyde method.

(Results)

| Amount of histamine released from peritoneal mast cell (Control = 100): | | | | | |
|---|---|---|---|---|---|
| Compound | $10^{-6}$ | $10^{-5}$ | $10^{-4}$ | $10^{-3}$ | (M) |
| Tranilast | 95 | 95 | 67 | 29 | |
| 11 | 55 | 51 | 59 | 13 | |
| 52 | 70 | 68 | 60 | 21 | |

Final concentration of DNP-Ascaris (antigen): 20 microgramms/ml

The compcund 11 and 52 showed the action cf inhibiting release of histamine from the mast cell even at the low concentration of $10^{-6}$M. It showed the stronger inhibitory activity than the conrrol Tranilast in the range of $10^{-6}$ M to $10^{-3}$ M.

TEST EXAMPLE 7

Preventive activity against passive systemic anaphylaxis (PSA) in guinea pig

Effect of the compound on prevention of death by passive systemic anaphylaxis was examined in guinea pig.

(Method)

Normal Hartley strain female guinea pig (body weight, 240-260 g) was sensitized by intravenous administraticn of anti-ovalbumin rabbit serum. It was perorally administered with the compound 11 in the amount of 200 mg/kg. One hour later, it was intravenously administered with 2% physiological saline solution of antigen ovalbumin at the rate of 0.05 ml. Thereafter, the state was observed, and the time (seconds) until death was measured. Similar treatments were given to the control group animals, to which physiological saline instead of the Compound 11 was perorally administered in the same procedure.

(Results)

As shown in Table, the average living time of the group of animals administered with Compound 11 was 441.7 seconds while that of the control group was 294.9 seconds. Thus, the Compound 11 was found to have statistically significant anti-PSA activity.

| Compound | Dose mg/kg | N | Required time (sec.) to death | | | | | Ave. time to death Mean ± S.E. | Extended rate (%) |
|---|---|---|---|---|---|---|---|---|---|
| Control | — po | 10 | 236 | 245 | 302 | 237 | 312 | 294.90 ± 16.2 | — |
|  |  |  | 311 | 251 | 315 | 374 | 366 |  |  |
| 11 | 200 po | 10 | 431 | 548 | 488 | 475 | 367 | 441.70 ± 21.5* | 49.8 |
|  |  |  | 492 | 431 | 485 | 352 | 348 |  |  |

Note:
*shows that p is less than 0.01.

TEST EXAMPLE 8

Acute Toxicity ddy-Strain-mice (male) and Wistar strain rats were used to obtain $LD_{50}$ values.

(Test method)

According to the ordinary procedure, suspension or solution of test sample was administered to the animals. From the number of the died animals until one week after the administration, $LD_{50}$ values were obtained by Probit method.

(Results)

| | $LD_{50}$ value (mg/kg body weight) | | |
|---|---|---|---|
| | Mouse | | Rat |
| Compound | p.o. | i.v. | p.o. |
| 11 | 10000< | 343.8 | 10000< |
| 20 | 10000< | 224.9 | 10000< |
| 24 | 10000< | 274.8 | — |
| 30 | 8381 | 257.7 | — |
| 14 | 10000< | 299.1 | — |

As shown in Table, the $LD_{50}$ values of the compounds were more than 10,000 mg/kg in peroral administration, and more than 200 mg/kg in intravenous administration in mouse. Accordingly, these compounds were found to be the substances having extremely low toxicity.

TEST EXAMPLE 9

Anti-passive cutaneous anaphylaxis activity (PCA) in rats

This test was conducted in a manner similar to that in Test Example 2, except that the dilutions of antiserum were 12- and 24-folds.

(Results)

| Compound | Dose (mg/kg) | Number of example | Anti-serum Dilution: × 12 | Anti-serum Dilution: × 24 |
|---|---|---|---|---|
| Control | | 10 | 0(%) | 0(%) |
| Tranilast | 200 | 10 | 2.1 | 10.7 |
| DSCG | 100 | 10 | 0 | 0 |
| Compound 11 | 50 | 10 | 20.8 | 23.0 |
| 51 | 10 | 10 | 28.1 | 30.3 |
|  | 50 | 10 | 34.2 | 37.5 |
| 14 | 10 | 10 | 29.8 | 31.3 |
|  | 50 | 10 | 36.7 | 40.5 |
| 53 | 50 | 10 | 26.1 | 23.9 |
| 54 | 10 | 10 | 33.0 | 34.3 |
|  | 50 | 10 | 38.8 | 42.6 |
| 57 | 10 | 10 | 37.0 | 30.9 |
|  | 50 | 10 | 45.0 | 50.1 |
| 59 | 10 | 10 | 22.0 | 25.1 |
|  | 50 | 10 | 65.7 | 62.0 |
| 56 | 10 | 10 | 44.7 | 43.6 |
|  | 50 | 10 | 49.7 | 58.4 |
| 58 | 10 | 10 | 40.2 | 43.1 |
|  | 50 | 10 | 50.8 | 57.6 |

From the above results it was found that the compounds according to the present invention had the extremely stronger anti-PCA activity than Tranilast and DSCG, and their anti-PCA activity were stronger than that of the compound 11.

TEST EXAMPLE 10

Activity of inhibition of release of histamine from mast cell in abdominal cavity of rat Examination was made on the activity of inhibition of histamine release from mast cell by antigen-antibody reaction.

Preparation of DNP-Ascaris antiserum was conducted in a manner similar to that in Test Example 6.

(Methods of collecting mast cell in abdominal cavity and thoracic cavity and of sensitizing cell)

Heparin-containing PBS was injected into the abdominal cavity of rat which was sacrificed by bleeding, after which the abdomen was well massaged, and then peritoneal exudate was sampled. The same liquid was also injected into the thoracic cavity, and after shaking the breast for several minutes, the thoracic cavity liquid was sampled, which was purified by washing several times by centrifugation. The number of the mast cells contained in this liquid was measured and adjusted to a designated concentration. (Mast cells, $8.0 \times 10^4$ cells/ml).

To the cell suspension (4 ml, $9 \times 10^5$ cells/ml), anti-DNP-Ascaris rat serum (PCA titer, 32) (4 ml) was added, and the mixture was incubated in the presence of heparin at 37° C. for 2.5 hours. To the solution, 70 microgramms/ml phosphatidylserin PBS solution (0.5 ml) was added and the mixture was incubated at 37° C. for 12 minutes, after which 140 microgramms/ml antigen DNP-Ascaris PBS solution (0.5 ml) was added and the mixture was incubated further for 20 minutes.

(Method of histamin assay)

After completion of the reaction, the reaction liquid was centrifuged (500 G, 10 min.) to obtain supernatant solution, and histamin in the supernatant solution was subjected to fluorometry by orthophthalal aldehyde method. The released amount of histamin in the control was shown as 100.

(Result)

|  | Mast cell in abdominal cavity $10^{-3}M$ | Mast cell in thoracic cavity $10^{-3}M$ |
|---|---|---|
| Compound 51 | 50.4 | 75.1 |
| DSCG | 76.8 | 104.8 |

From the above results it was found that the compound 51 showed an action of inhibiting release of histamine from the mast cells in abdominal acvity and thoracic cavity at a concentration of $10^{-3}M$, this activity having been stronger than DSCG.

TEST EXAMPLE 11

Acute Toxicity (Test method)

As test animals, ICR-strain mice (male) were used. According to the conventional procedure, suspension or solution of test sample was administered to the animals. From the number of the died animals until one week after the administration, $LD_{50}$ values were obtained by Provit method.

(Results)

| Compound | $LD_{50}$ Value (mg/kg of body weight) | |
|---|---|---|
| | Peroral administration | Intravenous administration |
| Compound 51 | 8000 & above | 238 |
| 14 |  | 347 |
| 54 |  | 312 |
| 52 | >10000 | 319 |

From the above results it was known that the esters other than methyl ester had the lower toxicity than the methyl ester (known compound).

TEST EXAMPLE 12

Actvity of inhibiting release of histamine from the mast cells in abdominal cavity and thoracic cavity of rat Collection of mast cells in abdominal cavity and thoracic cavity and sensitizing of cells were conducted in similar manners to those in Test Example 10, respectively.

(Histamine releasing substance)

(1) In the case of dextran (T-500)

The sample solution was treated with 105 microgramms/ml phosphatidylserin PBS solution (0.5 ml) and incubated at 37° C. for 30 minutes, followed by addition of 25 mg/ml dextran (T-500) PBS solution (0.5 ml) and further incubation for 15 minutes.

(2) In the case of antigen DNP-Ascaris (1) Preparation of DNP-Ascaris antiserum was conducted in manner similar to that in Test Example 6.

(2) Method of sensitizing cells and release of histamine:

This is conducted in amanner similar to that in Test Example 10.

(Quantitative determination method on histamin)

This is conducted in a manner similar to that in Test Example 10.

(Results)

| (1) Effect on release of histamine by dextran (T-500) | | | | |
|---|---|---|---|---|
| | Mast cell in abdominal cavity | | Mast cell in thoracic cavity | |
| | $10^{-4}M$ | $10^{-3}M$ | $10^{-4}$ | $10^{-3}M$ |
| Compound 14 | 94.5 | 40.2 | 55.6 | 42.2 |
| DSCG | 52.9 | 60.0 | 42.2 | 42.2 |
| (2) Effect on release of histamine by antigen DNP-Ascaris | | | | |
| | | Mast cell in abdominal cavity $10^{-3}M$ | Mast cell in thoracic cavity $10^{-3}M$ | |
| Compound 21 | | 48.3 | 73.0 | |
| DSCG | | 76.8 | 104.8 | |

From the above results it was seen that (1) the compound of the compound 14 showed the histamine release inhibiting activities at $10^{-4}$ and $10^{-3}$ M and its activity was almost the same as that of DSCG, and (2) the compound 14 showed a histamine release inhibiting activity at $10^{-3}M$, with the stronger inhibiting activity than DSCG.

From the above, it was shown that the compounds of the present invention had the anti-allergy action and immunomodulating action.

What is claimed is:

1. A compound of the general formula:

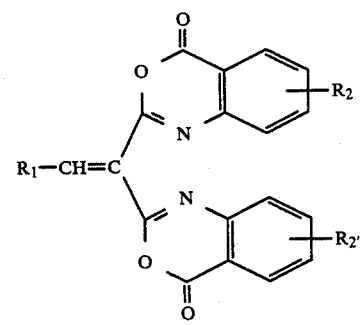

wherein $R^1$ is an aryl group or a substituted aryl group wherein the substituent is halogen, hydroxy, $C_{(1-6)}$ lower alkoxy, $C_{(1-6)}$ lower alkylenedioxy, halo $C_{(1-6)}$ lower alkyl, cyano, nitro, mono- or di-$C_{(1-6)}$ alkylamino or $C_{(1-6)}$ lower alkanoylamino; or a 5-membered or 6-membered $C_{(1-6)}$ alkyl substituted or unsubstituted heterocyclic group containing a heteroatom selected from oxygen, nitrogen and sulfur, or a condensed heterocyclic group consisting of a heterocycle as defined above and a benzene nucleus and $R^2$ and $R^{2'}$ are independently hydrogen, halogen, nitro, $C_{(1-6)}$ lower alkyl or $C_{(1-6)}$ lower alkoxy.

2. A pharmaceutical composition comprising a therapeutically effective amount of a compound of the general formula:

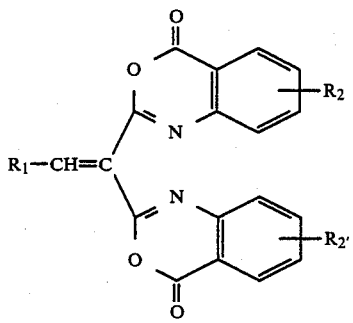

wherein $R^1$ is an aryl group or a substituted aryl group wherein the substituent is halogen, hydroxy, $C_{(1-6)}$ lower alkoxy, $C_{(1-6)}$ lower alkylenedioxy, halo $C_{(1-6)}$ lower alkyl, cyano, nitro, mono- or di-$C_{(1-6)}$ alkylamino or $C_{(1-6)}$ lower alkanoylamino; or a 5-membered or 6-membered $C_{(1-6)}$ alkyl substituted or unsubstituted heterocyclic group containing a heteroatom selected from oxygen, nitrogen and sulfur, or a condensed heterocyclic group consisting of a heterocycle as defined above and a benzene nucleus and $R^2$ and $R^{2'}$ are independently hydrogen, halogen, nitro, $C_{(1-6)}$ lower alkyl or $C_{(1-6)}$ lower alkoxy in association with a pharmaceutically acceptable carrier, diluent or excipient.

3. A method of treating allergic diseases in mammals comprising the administration, to a subject in need of such treatment, a therapeutically effective amount of the composition of claim 2.

* * * * *

UNITED STATES PATENT AND TRADEMARK OFFICE
CERTIFICATE OF CORRECTION

PATENT NO. : 4,822,791
DATED : April 18, 1989
INVENTOR(S) : Toshio Satoh, et al.

It is certified that error appears in the above-identified patent and that said Letters Patent is hereby corrected as shown below:

On the title page, Section [54], line 3: "ONE)9" should read as --ONE)]--.

Column 1, line 2: "ONE)9" should read as --ONE)]--.
Column 1, line 37: "a" should read as --an--.
Column 1, line 41: "a" should read as --an--.
Column 2, line 29: "$R^{2'1}$" should read as --$R^{2'}$--.
Column 8, line 66: "singl" should read as --single--.
Column 9, line 50: "methylendioxy" should read as --methylenedioxy--.
Column 9, line 57: "heteroxyclic" should read as --heterocyclic--.
Column 9, line 60: "s" should read as --as--.
Column 9, line 62: "monocylic" should read as --monocyclic--.
Column 10, line 49: "lky-" should read as --alky- --.
Column 10, line 63: "esrer" should read as --ester--.
Column 11, line 2: before "attached" insert --be--.
Column 11, line 7: "aroms" should read as --atoms--.
Column 11, line 7: after "one" insert --or--.

UNITED STATES PATENT AND TRADEMARK OFFICE
CERTIFICATE OF CORRECTION

PATENT NO. : 4,822,791

DATED : April 18, 1989

INVENTOR(S) : Toshio Satoh, et al.

It is certified that error appears in the above-identified patent and that said Letters Patent is hereby corrected as shown below:

Column 11, line 24, insert --(-- before "e.g.".

Column 11, line 24: "cf" should read as --of--.

Column 11, line 25: "ncn-alkyl" should read as --non-alkyl--.

Column 11, line 45: "froms" should read as --forms--.

Column 12, line 44: "Tne" should read as --The--.

Column 12, line 45: "duczion" should read as --duction--.

Column 12, line 58: "carbcxy" should read as --carboxy--.

Column 13, line 60: "grcup" should read as --group--.

Column 13, line 63: "carbcxy" should read as --carboxy--.

Column 14, line 54: "wirh" should read as --with--.

Column 14, line 67: "mceity" should read as --moiety--.

Column 15, line 28: "salzs" should read as --salts--.

Column 15, line 64: "halogene" should read as --halogen--.

UNITED STATES PATENT AND TRADEMARK OFFICE
CERTIFICATE OF CORRECTION

PATENT NO. : 4,822,791

DATED : April 18, 1989

INVENTOR(S) : Toshio Satoh, et al.

It is certified that error appears in the above-identified patent and that said Letters Patent is hereby corrected as shown below:

Column 16, line 34: "prccess" should read as --process--.

Column 16, line 37: "ccmpound" should read as --compound--.

Column 16, line 49: "acivated" should read as --activated--.

Column 16, line 53: "moeity" should read as --moiety--.

Column 17, line 42: "cf" should read as --of--.

Column 18, line 3: "ccmpound" should read as --compound--.

Column 18, line 24: "ccmpound" should read as --compound--.

Column 19, line 21: "slability" should read as --stability--.

Column 19, line 34: "porcelein" should read as --porcelain--.

Column 19, line 41: "formulatins" should read as --formulations--.

Column 19, line 53: "-CONH-" should read as -- -CON$\underline{H}$- --.

UNITED STATES PATENT AND TRADEMARK OFFICE
CERTIFICATE OF CORRECTION

PATENT NO. : 4,822,791
DATED : April 18, 1989
INVENTOR(S) : Toshio Satoh, et al.

It is certified that error appears in the above-identified patent and that said Letters Patent is hereby corrected as shown below:

Column 19, line 62: "-CONH-" should read as -- -CON$\underline{H}$- --.

Column 20, line 11: "($I_o^d$d)" should read as --($I_o^d$)--.

Column 20, line 20: "-CONH-" should read as -- -CON$\underline{H}$- --.

Column 21, line 17: "cf" should read as --of--.

Column 21, line 19: "calucium" should read as --calcium--.

Column 21, line 35: "compound" should read as --compounds--.

Column 21, line 68: "conventicnal" should read as --conventional--.

Column 23, line 18: "(8 1)" should read as --(8 ml)--.

Column 23, line 66: "s, 1H" should read as --s, 1$\underline{H}$--.

Column 24, line 28: "CONH)" should read as --CON$\underline{H}$)--.

Column 24, line 30: "6.9014 8.90" should read as --6.90 - 8.90--.

UNITED STATES PATENT AND TRADEMARK OFFICE
CERTIFICATE OF CORRECTION

PATENT NO. : 4,822,791
DATED : April 18, 1989
INVENTOR(S) : Toshio Satoh, et al.

It is certified that error appears in the above-identified patent and that said Letters Patent is hereby corrected as shown below:

Column 25, line 23: "(CONH)" should read as --(CO$\underline{N}$H)--.

Column 25, line 24: "(CONH)" should read as --(CO$\underline{N}$H)--.

Column 26, line 4: "{2-thienyl)" should read as --(2-thienyl)--.

Column 26, line 36: "diimimo" should read as --diimino--.

Column 26, line 41: "Afrer" should read as --After--.

Column 26, line 58: "ro" should read as --to--.

Column 27, line 41: "-CH2-" should read as -- -C$\underline{H}_2$- --.

Column 29, line 10: "nmol)" should read as --mmol)--.

Column 30, line 20: "(-COOCH$_3$)" should read as --(-$\underline{C}$OOC$\underline{H}_3$)--.

Column 30, line 21: "(-O/NH-)" should read as --(-$\underline{C}$ONH-)--.

Column 30, line 24: "N-CHhd 3)" should read as --N-C$\underline{H}_3$)--.

UNITED STATES PATENT AND TRADEMARK OFFICE
CERTIFICATE OF CORRECTION

PATENT NO. : 4,822,791

DATED : April 18, 1989

INVENTOR(S) : Toshio Satoh, et al.

It is certified that error appears in the above-identified patent and that said Letters Patent is hereby corrected as shown below:

Column 30, line 35: "-CON$\underline{N}$Htaken" should read as -- -CONH- taken--.

Column 31, compound 33: "4-Br-$C_6H_4$-" should read as

Column 31, compound 49: "$C_6H_5$-" should read as

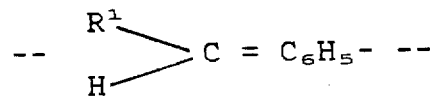

Column 33, line 1: "cf" should read as --of--.

Column 33, line 26: "-CON/-)" should read as -- -CON$\underline{H}$-)--.

Column 34, line 62: "-CH(C$\underline{H}$3)2)" should read as -- -CH(C$\underline{H}_3$)$_2$)--.

Column 34, line 64: after "was" insert --suspended in dry benzene (100 ml) and (COCl)$_2$ (3.2 ml, 37.2--.

Column 35, line 62: "aquecus" should read as --aqueous--.

Column 36, line 41: "-CH2CH" should read as -- -C$\underline{H}_2$CH--.

UNITED STATES PATENT AND TRADEMARK OFFICE
CERTIFICATE OF CORRECTION

PATENT NO. : 4,822,791
DATED : April 18, 1989
INVENTOR(S) : Toshio Satoh, et al.

It is certified that error appears in the above-identified patent and that said Letters Patent is hereby corrected as shown below:

Column 36, line 45: "(1,3-" should read as --[(1,3- --.

Column 37, line 15: "mmcl" should read as --mmol--.

Column 37, lines 34 and 35 (both instances): "-C(CH3)3)" should read as -- -C($\underline{CH}_3$)$_3$)--.

Column 37, line 38: "cf" should read as --of--.

Column 37, line 50: "frcm" should read as --from--.

Column 38, line 1: "-CH(CH3)x2" should read as -- -CH($\underline{CH}_3$)x2--.

Column 38, line 21: after "area" insert --under the peak which was presumed to be 4-bromomethyl- --.

Column 38, line 52: ":S" should read as --(S--.

Column 38, line 54: "-CH-" should read as -- -CH$_2$- --.

Column 39, line 59: "cf" should read as --of--.

Column 39, line 66: "chlcroform" should read as --chloroform--.

Column 39, line 67: "(benzene ethyl" should read as --benzene:ethyl--.

Column 40, line 2: "pectra" should read as --spectra--.

UNITED STATES PATENT AND TRADEMARK OFFICE
CERTIFICATE OF CORRECTION

PATENT NO. : 4,822,791

DATED : April 18, 1989

INVENTOR(S) : Toshio Satoh, et al.

It is certified that error appears in the above-identified patent and that said Letters Patent is hereby corrected as shown below:

Column 40, line 11: "suspensed" should read as --suspended--.

Column 40, line 20: "rrcm" should read as --from--.

Column 40, line 60: "where" should read as --were--.

Column 42, line 5: "di(L-arcinine)" should read as --di(L-arginine)--.

Column 42, line 62: "Anti-hvaluronidase" should read as --Anti-hyaluronidase--.

Column 43, line 2: "Svmposium" should read as --Symposium--.

Column 43, line 9: "soluticn" should read as --solution--.

Column 43, line 21: "subjecred" should read as --subjected--.

Column 43, line 62: "anaohylaxis" should read as --anaphylaxis--.

Column 44, line 45: "tc shcw" should read as --to show--.

Column 44, line 46: "discdium" should read as --disodium--.

Column 44, line 50: "oassive" should read as --passive--.

UNITED STATES PATENT AND TRADEMARK OFFICE
CERTIFICATE OF CORRECTION

PATENT NO. : 4,822,791

DATED : April 18, 1989

INVENTOR(S) : Toshio Satoh, et al.

It is certified that error appears in the above-identified patent and that said Letters Patent is hereby corrected as shown below:

Column 44, line 64: "solultion" should read as --solution--.

Column 48, line 21: "106" should read as --$10^6$--.

Column 48, line 37: "crthophthalalde-" should read as --orthophthalalde- --.

Column 48, line 51: "compcund" should read as --compound--.

Column 48, line 51: "cf" should read as --of--.

Column 48, line 54: "conrrol" should read as --control--.

Column 48, line 67: "ministraticn" should read as --ministration--.

Column 49, line 41: "died" should read as --dead--.

Column 50, line 43: "cn" should read as --on--.

Column 51, line 22: "acvity" should read as --activity--.

Column 51, line 33: "died" should read as --dead--.

UNITED STATES PATENT AND TRADEMARK OFFICE
CERTIFICATE OF CORRECTION

PATENT NO. : 4,822,791

DATED : April 18, 1989

INVENTOR(S) : Toshio Satoh, et al.

It is certified that error appears in the above-identified patent and that said Letters Patent is hereby corrected as shown below:

Column 51, line 53: "Actvity" should read as --Activity--.

Signed and Sealed this

Twenty-fifth Day of June, 1991

*Attest:*

HARRY F. MANBECK, JR.

*Attesting Officer*     *Commissioner of Patents and Trademarks*